US007897583B2

(12) United States Patent
McKay et al.

(10) Patent No.: US 7,897,583 B2
(45) Date of Patent: Mar. 1, 2011

(54) COMPOSITIONS AND THEIR USES DIRECTED TO PTPRU

(75) Inventors: Robert McKay, Poway, CA (US); Ravi Jain, Carlsbad, CA (US); Kenneth W. Dobie, Del Mar, CA (US); Sanjay K. Pandey, Encinitas, CA (US); Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 76 days.

(21) Appl. No.: 11/915,309

(22) PCT Filed: May 24, 2006

(86) PCT No.: PCT/US2006/020388

§ 371 (c)(1), (2), (4) Date: Jun. 23, 2008

(87) PCT Pub. No.: WO2006/127976

PCT Pub. Date: Nov. 30, 2006

(65) Prior Publication Data

US 2008/0280845 A1 Nov. 13, 2008

Related U.S. Application Data

(60) Provisional application No. 60/684,398, filed on May 24, 2005.

(51) Int. Cl.
*A61K 48/00* (2006.01)
*C07H 21/02* (2006.01)
*C07H 21/04* (2006.01)

(52) U.S. Cl. ....................... 514/44; 536/23.1; 536/24.5; 536/24.31; 536/24.33

(58) Field of Classification Search ....................... None
See application file for complete search history.

(56) References Cited

U.S. PATENT DOCUMENTS

| | | | |
|---|---|---|---|
| 5,705,623 A * | 1/1998 | Wiggins et al. | 536/23.2 |
| 5,801,154 A | 9/1998 | Baracchini et al. | |
| 6,277,640 B1 | 8/2001 | Bennett et al. | |
| 6,582,908 B2 | 6/2003 | Fodor et al. | |
| 2001/0053519 A1 | 12/2001 | Fodor et al. | |
| 2003/0228597 A1 | 12/2003 | Cowsert et al. | |
| 2005/0019915 A1 | 1/2005 | Bennett et al. | |
| 2009/0042827 A1* | 2/2009 | Vaillant et al. | 514/44 |

FOREIGN PATENT DOCUMENTS

| | | | |
|---|---|---|---|
| WO | WO 93/24510 | 12/1993 | |
| WO | WO 94/26764 | 11/1994 | |
| WO | WO 2004/094636 | 11/2004 | |
| WO | WO 2005/026735 | 3/2005 | |
| WO | WO 2005/026735 A2 * | 3/2005 | 514/44 |

OTHER PUBLICATIONS

Avraham et al., Characterization and chromosomal localization of PTPRO, a novel receptor protein tyrosine phosphatase, expressed in hematopoietic stem cells, 1997, Gene, 204, pp. 5-16.*

Zellweger et al., Antitumor Activity of Antisense Clusterin Oligonucleotides is Improved in Vitro and in Vivo by Incorporation of 2'-O-(2-Methoxy)Ethyl Chemistry, 2001, J. Pharmacol Exp Ther, 298(3), pp. 934-940.*

Hershman et al., RPTP{micro} and protein tyrosine phosphorylation regulate K+ channel mRNA expression in adult cardiac myocytes, 2000, Am J Physiol, 278, pp. 397-403.*

Taniguchi et al., The Receptor Protein Kinase Phosphatase, PTP-RO, Is Upregulated During Megakaryocyte Differentiation and Is Associated With the c-Kit Receptor, 1999, Blood, vol. 94, No. 2, pp. 539-549.*

Ostenson et al., Overexpression of Protein-Tyrosinase Phosphatase Is Linked to Impaired Glucose-Induced Insulin Secretion in Hereditary Diabetic Goto-Kakizaki Rats, 2002, Biochemical and Biophysical Research Communications, 291, pp. 945-950.*

Aguiar et al., "PTPROt: An Alternatively Spliced and Developmentally Regulated B-Lymphoid Phosphatase That Promoted G0/G1 Arrest" Blood (1999) 94:2403-2413.

Amoui et al., "Expression of a Structurally Unique Osteoclastic Protein-tyrosine Phosphatase Is Driven by an Alternative Intronic Cell Type-specific Promoter" J. Biol. Chem. (2003) 278:44273-44280.

Avraham et al., "Characterization and chromosomal localization of PTPRO, a novel receptor protein tyrosine phosphatase, expressed in hematopoietic stem cells" Gene (1997) 204:5-16.

Beltran et al., "Expression of PTPRO during mouse development suggests involvement in axonogenesis and differentiation of NT-3 and NGF-dependent neurons" J. Comp. Neurol. (2003) 456:384-395.

Branch et al., "A good antisense molecule is hard to fin" *TIBS* (1998) 23:45-50.

Chin, "On the preparation and Utilization of Isolated and Purified Oligonucleotides" Document purportedly located on a CD-ROM and contributed to the public collection of the Katherine R. Everett Law Library of the University of North Carolina on Mar. 14, 2002.

(Continued)

*Primary Examiner*—Amy Bowman
(74) *Attorney, Agent, or Firm*—Knobbe, Martens, Olson & Bear

(57) ABSTRACT

Disclosed herein are compounds, compositions and methods for modulating the expression of PTPRU in a cell, tissue or animal. Also provided are methods of active target segment validation. Also provided are uses of disclosed compounds and compositions in the manufacture of a medicament for treatment of diseases and disorders. Also provided are methods for the prevention, amelioration and/or treatment of diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease by administration of antisense compounds targeted to PTPRU.

36 Claims, No Drawings

OTHER PUBLICATIONS

Crooke et al., "Basic Principles of Antisense Therapeutics" Antisense Research and Application (1998) Chapter 1:1-50.
Crossland et al., "Molecular cloning and characterization of PTPπ, a novel receptor-like protein-tyrosine phosphatase" Biochem. J. (1996) 319(Pt 1):249-254.
Gait et al., "Applications of Chemically Synthesized RNA" RNA: Protein Interactions, Ed. Smith (1998) 1-36.
Gallo et al., "2'-C-Methyluridine phosphopramidite: a new building block for the preparation of RNA analogues in" Tetrahedron (2001) 57:5707-5713.
Mcardle et al., "Protein Tyrosine Phosphatase Genes Downregulated in Melanoma" J. Invest. Dermatol. (2001) 177:1255-1260.
Mori et al., "Identification of Genes Uniquely Involved in Frequent Microsatellite Instability Colon Carcinogenesis by Expression Profiling Combined with Epigenetic Scanning" Cancer Res. (2004) 64:2434-2438.
Motiwala et al., "Suppression of the protein tyrosine phosphatase receptor type O gene (PTPRO) by methylation in hepatocellular carcinomas" Oncogene (2003) 22:6319-6331.
New England Biolabs 1998/1999 Catalog, cover page, pp. 121 and 284.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Scaringe, "RNA Oligonucleotide Synthesis via 5'-Silyl-2'-Orthoester Chemistry" Methods (2001) 23:206-217.
Stepanek et al., "CRYP-2/cPTPRO is a neurite inhibitory repulsive guidance cue for retinal neurons in vitro" J. Cell. Biol. (2001) 154:867-878.
Taniguchi et al., "The Receptor Protein Tyrosine Phosphatase, PTP-RO, Is Upregulated During Megakaryocyte Differentiation and Is Associated With the c-Kit Receptor" Blood (1999) 94:539-549.
Thomas et al., "GLEPP1, a Renal Glomerular Epithelial Cell (Podocyte) Membrane Protein-tyrosine Phosphatase" J. Biol. Chem. (1994) 269:19953-19962.
Wang et al., "Molecular Cloning and Characterization of a Novel Human Receptor Protein Tyrosine Phosphatase Gene, hPTP-K: Down-Regulation of Gene Expression by PMA and Calcium Ionophore in Jukrat T Lymphoma Cells" Biochem. Biophys. Res. Commun. (1997) 231:77-81.
Wang et al., "Transcriptional regulation of a receptor protein tyrosine phosphatase gene hPTP-J by PKC-mediated signaling pathways in Jurkat and Molt-4 T lymphoma cells" Biochem. Biophys. Acta. (1999) 1450:331-340.
Wang et al., "Characterization of PCP-2, a novel receptor protein tyrosine phosphatase of the MAM domain family." Oncogene (1996) 12:2555-2562.
Wharram et al., "Altered podocyte structure in GLEPP1 (Ptpro)-deficient mice aswsociated with hypertension and low glomerular filtration rate" J. Clin. Invest. (2000) 106:1281-1290.
Yan et al., "Physical and Functional Interaction between Receptor-like Protein Tyrosine Phosphatase PCP-2 and B-Catenin" Biochemistry (2002) 41:15854-15860.
Zhang, "Protein-Tyrosine Phosphatases: Biological Function, Structural Characteristics, and Mechanism of Catalysis" Crit. Rev. Biochem. Mol. (1998) 33:1-52.
International Search Report from PCT/US06/20388 dated Jan. 3, 2007.
Czauderna et al., "Structural variations and stabilising modifications of synthetic siRNAs in mammalian cells" Nucleic Acids Research (2003) 31(11):2705-2716.
Suhr et al., "Antisense oligodeoxynucleotide evidence that a unique osteoclastic protein-tyrosine phosphatase is essential for osteoclastic resorption" Journal of Bone and Mineral Research (2001) 16(10):1795-1803.
European Search Report for application EP 06771266.1 dated Oct. 6, 2010.

* cited by examiner

SEQUENCE LISTING

```
<160> NUMBER OF SEQ ID NOS: 258

<210> SEQ ID NO 1
<211> LENGTH: 5637
<212> TYPE: DNA
<213> ORGANISM: H. Sapiens

<400> SEQUENCE: 1

aattccgggc gccagtcccg ctccgcgccg cgccgctccg ctccggctcg ggctccggct     60

cgcctcgggc tgggctcggg ctccgggggc ggcgtccccg ccgccgggcc ccgggacggg    120

cggcgacgct ccaaccatgg cccgtgccca ggcgctcgtg ctggcactca ccttccagct    180

ctgcgcgccg gagaccgaga ctccggcagc tggctgcacc ttcgaggagg caagtgaccc    240

agcagtgccc tgcgagtaca gccaggccca gtacgatgac ttccagtggg agcaagtgcg    300

aatccaccct ggcacccggg cacctgcgga cctgccccac ggctcctact tgatggtcaa    360

cacttcccag catgccccag gccagcgagc ccatgtcatc ttccagagcc tgagcgagaa    420

tgatacccac tgtgtgcagt tcagctactt cctgtacagc cgggacgggc acaggccggg    480

caccctgggc gtctacgtgc gcgttaatgg gggccccctg ggcagtgctg tgtggaatat    540

gactggatcc cacggccgtc agtggcacca ggctgagctg gctgtcagca ctttctggcc    600

caatgaatat caggtgctgt ttgaggccct catctcccca gaccgcaggg gctacatggg    660

cctagatgac atcctgcttc tcagctaccc ctgcgcaaag gccccacact tctcccgcct    720

gggcgacgtg gaggtcaacg cgggccagaa cgcgtcgttc cagtgcatgg ccgcgggcag    780

agcggccatg cgccaacgct tcctcttgca acggcagagc ggggccctgg tgccggcggc    840

gggcgttcgg cacatcagcc accggcgctt cctggccact ttcccgctgg ctgccgtgag    900

ccgcgccgag caggacctgt accgctgtgt gtcccaggcc ccgcgcggcg cgggcgtctc    960
```

-continued

```
taacttcgcg gagctcatcg tcaaggagcc cccaactccc atcgcgcccc cacagctgct   1020
gcgtgctggc cccacctacc tcatcatcca gctcaacacc aactccatca ttggcgacgg   1080
gccgatcgtg cgcaaggaga ttgagtaccg catggcgcgc gggccctggg ctgaggtgca   1140
cgccgtcagc ctgcagacct acaagctgtg gcacctcgac cccgacacag agtatgagat   1200
cagcgtgctg ctcacgcgtc ccggagacgg cggcactggc cgccctgggc cacccctcat   1260
cagccgcacc aaatgcgcag agcccatgag ggcccccaaa ggcctggctt ttgctgagat   1320
ccaggcccgt cagctgaccc tgcagtggga accactgggc tacaacgtga cgcgttgcca   1380
cacctatact gtgtcgctgt gctatcacta caccctgggc agcagccaca accagaccat   1440
ccgagagtgt gtgaagacag agcaaggtgt cagccgctac accatcaaga acctgctgcc   1500
ctatcggaac gttcacgtga ggcttgtcct cactaaccct gaggggcgca aagagggcaa   1560
ggaggtcact ttccagacgg atgaggatgt gcccagtggg attgcagccg agtccctgac   1620
cttcactcca ctggaggaca tgatcttcct caagtgggag gagccccagg agcccaatgg   1680
tctcatcacc cagtatgaga tcagctacca gagcatcgag tcatcagacc cggcagtgaa   1740
cgtgccaggc ccacgacgta ccatctccaa gctccgcaat gagacctacc atgtcttctc   1800
caacctgcac ccaggcacca cctacctgtt ctccgtgcgg gcccgcacag gcaaaggctt   1860
cggccaggcg gcactcactg agataaccac taacatctct gctcccagct ttgattatgc   1920
cgacatgccg tcacccctgg gcgagtctga gaacaccatc accgtgctgc tgaggccggc   1980
acagggccgc ggtgcgccca tcagtgtgta ccaggtgatt gtggaggagg agcgggcgcg   2040
gaggctgcgg cgggagcgag gtggacagga ctgcttccca gtgccattga ccttcgaggc   2100
ggcgctggcc cgaggcctgg tgcactactt cggggccgaa ctggcggcca gcagtctacc   2160
tgaggccatg ccctttaccg tgggtgacaa ccagacctac cgaggcttct ggaacccacc   2220
acttgagcct aggaaggcct atctcatcta cttccaggca gcaagccacc tgaaggggga   2280
gacccggctg aattgcatcc gcattgccag gaaagctgcc tgcaaggaaa gcaagcggcc   2340
cctggaggtg tcccagagat cggaggagat ggggcttatc ctgggcatct gtgcaggggg   2400
gcttgctgtc ctcatccttc tcctgggtgc catcattgtc atcatccgca aagggagaga   2460
ccactatgcc tactcctact acccgaagcc ggtgaacatg accaaggcca ccgtcaacta   2520
ccgccaggag aagacacaca tgatgagcgc cgtggaccgc agcttcacag accagagcac   2580
cctgcaggag gacgagcggc tgggcctgtc cttcatggac acccatggct acagcacccg   2640
gggagaccag cgcagcggtg gggtcactga ggccagcagc ctcctggggg gctccccgag   2700
gcgtccctgt ggccggaagg gctccccata ccacacgggg cagctgcacc ctgcggtgcg   2760
tgtcgcagac cttctgcagc acatcaacca gatgaagacg gccgagggtt acggcttcaa   2820
gcaggagtat gagagcttct ttgaaggctg ggacgccaca aagaagaaag acaaggtcaa   2880
gggcagccgg caggagccaa tgcctgccta tgatcggcac cgagtgaaac tgcacccgat   2940
gctgggagac cccaatgccg actacattaa tgccaactac atagatggtt accacaggtc   3000
aaaccacttc atagccactc aagggccgaa gcctgagatg gtctatgact tctggcgtat   3060
ggtgtggcag gagcactgtt ccagcatcgt catgatcacc aagctggtcg aggtgggcag   3120
ggtgaaatgc tcacggtact ggccggagga ctcagacacc tacggggaca tcaagattat   3180
gctggtgaag acagagaccc tggctgagta tgtcgtgcgc acttttgccc tggagcggag   3240
aggctactct gcccggcacg aggtccgcca gttccacttc acagcgtggc cagagcatgg   3300
```

-continued

```
cgtcccctac catgccacgg ggctgctggc tttcatccgg cgcgtgaagg cctccacccc   3360
acctgatgcc gggcccattg tcatccactg cagcgcgggc accggccgca caggttgcta   3420
tatcgtcctg gatgtgatgc tggacatggc agagtgtgag ggcgtcgtgg acatttacaa   3480
ctgtgtgaag actctctgct cccggcgtgt caacatgatc cagactgagg agcagtacat   3540
cttcattcat gatgcaatcc tggaggcctg cctgtgtggg gagaccacca tccctgtcag   3600
tgagttcaag gccacctaca aggagatgat ccgcattgat cctcagagta attcctccca   3660
gctgcgggaa gagttccaga cgctgaactc ggtcaccccg ccgctggacg tggaggagtg   3720
cagcatcgcc ctgttgcccc ggaaccgcga caagaaccgc agcatggacg tcctgccgcc   3780
cgaccgctgc ctgcccttcc tcatctccac tgatggggac tccaacaact acattaatgc   3840
agccctgact gacagctaca cacggagtgc ggccttcatc gtgaccctgc acccgctgca   3900
gagcaccacg cccgacttct ggcggctggt ctacgattac gggtgcacct ccatcgtcat   3960
gctcaaccag ctgaaccagt ccaactccgc ctggccctgc ctgcagtact ggccagagcc   4020
aggccggcag caatatggcc tcatggaggt ggagtttatg tcgggcacag ctgatgaaga   4080
cttagtggct cgagtcttcc gggtgcagaa catctctcgg ttgcaggagg ggcacctgct   4140
ggtgcggcac ttccagttcc tgcgctggtc tgcataccgg gacacacctg actccaagaa   4200
ggccttcttg cacctgctgg ctgaggtgga caagtggcag gccgagagtg gggatgggcg   4260
caccatcgtg cactgcctaa acgggggagg acgcagcggc accttctgcg cctgcgccac   4320
ggtcctggag atgatccgct gccacaactt ggtggacgtt ttctttgctg ccaaaaccct   4380
ccggaactac aaacccaaca tggtggagac catggatcag taccactttt gctacgatgt   4440
ggccctggag tacttggagg ggctggagtc aagatagcgg ggccctggcc tggggcaccc   4500
actgcacact cagggccaga cccaccatcc tggactggcg aggaagatca gtgcctcctg   4560
ctctgcccaa acacactccc atggggcaag cactggagtg gatgctgggc tatcttgctc   4620
cccttccac tgtgggcagg gcctttcgct tgtcccatgg gcgggtggtg ggccaaggag   4680
gagcttagca agtctgcagc ccagccccac ctccataggg tcctgcaggc ctgtgctgag   4740
aggcctggtg ctgcctggca gagtgacaaa ggctcaggac ggctggctct gggggactca   4800
ggccaagccc cttggcacca tcctggcttt tggcagggat gagtgaggcc ctgcagagag   4860
catcccaggc caaggttccc actcagcctg ccccctctgc atgtgggtag aggatgtact   4920
gggacttggc atttaggatt ccatctggcc cagcccctga aggtcctggg gaagcaggtc   4980
tcaattctga atagccagtg gggcacactg actgtcctcc ccaggggaac tgcagcgccc   5040
tcctccccac tgccccctgc agcccctgag atattttgct cactatccct ccccacttgc   5100
ttccctgata tgtgctctga gcttccctga accaggatct gcctattact gctgtgcccc   5160
atggggggct ccttccctgc ctgacccact gttgcagaat gaagtcacct cgccccccctc   5220
ttcctttaat cttcaggcct cactggcctg tcctgctcag cttgggccag tgacaatctg   5280
caaggctgaa caacagcccc tggggttgag gcccctgtgg ctcctggtca ggctgcccgt   5340
tgtggggagg ggcagtgtta gagcagggct ggtcataccc tctggagttc agaggaagag   5400
gtaggaccag tgcttttttg tttcttttgt tatttttggt tgggtgggtg ggaaggtctc   5460
tttaaaatgg ggcaggccac acccccattc cgtgcctcaa tttccccatc tgtaaactgt   5520
agatatgact actgacctac ctcgcagggg gctgtgggga ggcataagct gatgtttgta   5580
aagcgctttg taaataaacg tgctctctga atgccaaaaa aaaaaaaaaa aaaaaaa      5637
```

<210> SEQ ID NO 2
<211> LENGTH: 5618
<212> TYPE: DNA
<213> ORGANISM: H. Sapiens

<400> SEQUENCE: 2

```
aattccgggc gccagtcccg ctccgcgccg cgccgctccg ctccggctcg ggctccggct     60

cgcctcgggc tgggctcggg ctccgggggc ggcgtccccg ccgccgggcc ccgggacggg    120

cggcgacgct ccaaccatgg cccgtgccca ggcgctcgtg ctggcactca ccttccagct    180

ctgcgcgccg gagaccgaga ctccggcagc tggctgcacc ttcgaggagg caagtgaccc    240

agcagtgccc tgcgagtaca gccaggccca gtacgatgac ttccagtggg agcaagtgcg    300

aatccaccct ggcacccggg cacctgcgga cctgccccac ggctcctact tgatggtcaa    360

cacttcccag catgccccag gccagcgagc ccatgtcatc ttccagagcc tgagcgagaa    420

tgatacccac tgtgtgcagt tcagctactt cctgtacagc cgggacgggc acagcccggg    480

caccctgggc gtctacgtgc gcgttaatgg gggccccctg ggcagtgctg tgtggaatat    540

gactggatcc cacggccgtc agtggcacca ggctgagctg gctgtcagca ctttctggcc    600

caatgaatat caggtgctgt ttgaggccct catctcccca gaccgcaggg gctacatggg    660

cctagatgac atcctgcttc tcagctaccc ctgcgcaaag gccccacact tctcccgcct    720

gggcgacgtg gaggtcaacg cgggccagaa cgcgtcgttc cagtgcatgg ccgcgggcag    780

agcggccgag gccgaacgct tcctcttgca acggcagagc ggggcgctgg tgccggcggc    840

gggcgtgcgg cacatcagcc accggcgctt cctggccact ttcccgctgg ctgccgtgag    900

ccgcgccgag caggacctgt accgctgtgt gtcccaggcc ccgcgcggcg cgggcgtctc    960

taacttcgcg gagctcatcg tcaaggagcc ccccaactcc atcgcgcccc cacagctgct   1020

gcgtgctggc cccacctacc tcatcatcca gctcaacacc aactccatca ttggcgacgg   1080

gccgatcgtg cgcaaggaga ttgagtaccg catggcgcgc gggccctggg ctgaggtgca   1140

cgccgtcagc ctgcagacct acaagctgtg gcacctcgac cccgacacag agtatgagat   1200

cagcgtgctg ctcacgcgtc ccggagacgg cggcactggc cgccctgggc cacccctcat   1260

cagccgcacc aaatgcgcag agcccatgag ggccccccaaa ggcctggctt ttgctgagat   1320

ccaggcccgt cagctgaccc tgcagtggga accactgggc tacaacgtga cgcgttgcca   1380

cacctatact gtgtcgctgt gctatcacta caccctgggc agcagccaca accagaccat   1440

ccgagagtgt gtgaagacag agcaaggtgt cagccgctac accatcaaga acctgctgcc   1500

ctatcggaac gttcacgtga ggcttgtcct cactaaccct gaggggcgca aagagggcaa   1560

ggaggtcact ttccagacgg atgaggatgt gcccagtggg attgcagccg agtccctgac   1620

cttcactcca ctggaggaca tgatcttcct caagtgggag gagccccagg agcccaatgg   1680

tctcatcacc cagtatgaga tcagctacca gagcatcgag tcatcagacc cggcagtgaa   1740

cgtgccaggc ccacgacgta ccatctccaa gctccgcaat gagacctacc atgtcttctc   1800

caacctgcac ccaggcacca cctacctgtt ctccgtgcgg gcccgcacag gcaaaggctt   1860

cggccaggcg gcactcactg agataaccac taacatctct gctcccagct ttgattatgc   1920

cgacatgccg tcacccctgg gcgagtctga gaacaccatc accgtgctgc tgaggccggc   1980

acagggccgc ggtgcgccca tcagtgtgta ccaggtgatt gtggaggagg agcgggcgcg   2040

gaggctgcgg cgggagccag gtggacagga ctgcttccca gtgccattga ccttcgaggc   2100

ggcgctggcc cgaggcctgg tgcactactt cggggccgaa ctggcggcca gcagtctacc   2160
```

-continued

```
tgaggccatg ccctttaccg tgggtgacaa ccagacctac cgaggcttct ggaacccacc   2220

acttgagcct aggaaggcct atctcatcta cttccaggca gcaagccacc tgaaggggga   2280

gacccggctg aattgcatcc gcattgccag gaaagctgcc tgcaaggaaa gcaagcggcc   2340

cctggaggtg tcccagagat cggaggagat ggggcttatc ctgggcatct gtgcaggggg   2400

gcttgctgtc ctcatccttc tcctgggtgc catcattgtc atcatccgca aagggaagcc   2460

ggtgaacatg accaaggcca ccgtcaacta ccgccaggag aagacacaca tgatgagcgc   2520

cgtggaccgc agcttcacag accagagcac cctgcaggag gacgagcggc tgggcctgtc   2580

cttcatggac acccatggct acagcacccg gggagaccag cgcagcggtg gggtcactga   2640

ggccagcagc ctcctggggg gctccccgag gcgtccctgt ggccggaagg gctccccata   2700

ccacacgggg cagctgcacc ctgcggtgcg tgtcgcagac cttctgcagc acatcaacca   2760

gatgaagacg gccgagggtt acggcttcaa gcaggagtac gagagcttct ttgaaggctg   2820

ggacgccaca aagaagaaag acaaggtcaa gggcagccgg caggagccaa tgcctgccta   2880

tgatcggcac cgagtgaaac tgcacccgat gctgggagac cccaatgccg actacattaa   2940

tgccaactac atagatattc ggataaaccg agaaggttac cacaggtcaa accacttcat   3000

agccactcaa gggccgaagc ctgagatggt ctatgacttc tggcgtatgg tgtggcagga   3060

gcactgttcc agcatcgtca tgatcaccaa gctggtcgag gtgggcaggg tgaaatgctc   3120

acggtactgg ccggaggact cagacaccta cggggacatc aagattatgc tggtgaagac   3180

agagaccctg gctgagtatg tcgtgcgcac ttttgccctg gagcggagag gctactctgc   3240

ccggcacgag gtccgccagt tccacttcac agcgtggcca gagcatggcg tcccctacca   3300

tgccacgggg ctgctggctt tcatccggcg cgtgaaggcc tccaccccac ctgatgccgg   3360

gcccattgtc atccactgca gcgcgggcac cggccgcaca ggttgctata tcgtcctgga   3420

tgtgatgctg gacatggcag agtgtgaggg cgtcgtggac atttacaact gtgtgaagac   3480

tctctgctcc cggcgtgtca acatgatcca gactgaggag cagtacatct tcattcatga   3540

tgcaatcctg gaggcctgcc tgtgtgggga gaccaccatc cctgtcagtg agttcaaggc   3600

cacctacaag gagatgatcc gcattgatcc tcagagtaat tcctcccagc tgcgggaaga   3660

gttccagacg ctgaactcgg tcaccccgcc gctggacgtg gaggagtgca gcatcgccct   3720

gttgccccgg aaccgcgaca agaaccgcag catggacgtc ctgccgcccg accgctgcct   3780

gcccttcctc atctccactg atggggactc caacaactac attaatgcag ccctgactga   3840

cagctacaca cggagtgcgg ccttcatcgt gaccctgcac ccgctgcaga gcaccacgcc   3900

cgacttctgg cggctggtct acgattacgg gtgcacctcc atcgtcatgc tcaaccagct   3960

gaaccagtcc aactccgcct ggccctgcct gcagtactgg ccagagccag gccggcagca   4020

atatggcctc atggaggtgg agtttatgtc gggcacagct gatgaagact tagtggctcg   4080

agtcttccgg gtgcagaaca tctctcggga ggggcacctg ctggtgcggc acttccagtt   4140

cctgcgctgg tctgcatacc gggacacacc tgactccaag aaggccttct tgcacctgct   4200

ggctgaggtg gacaagtggc aggccgagag tggggatggg cgcaccatcg tgcactgcct   4260

aaacggggga ggacgcagcg gcaccttctg cgcctgcgcc acggtcctgg agatgatccg   4320

ctgccacaac ttggtggacg ttttctttgc tgccaaaacc ctccggaact acaaacccaa   4380

catggtggag accatggatc agtaccactt ttgctacgat gtggccctgg agtacttgga   4440

ggggctggag tcaagatagc ggggccctgg cctggggcac ccactgcaca ctcagggcca   4500

gacccaccat cctggactgg cgaggaagat cagtgcctcc tgctctgccc aaacacactc   4560
```

-continued

```
ccatggggca agcactggag tggatgctgg gctatcttgc tccccttcc actgtgggca   4620

gggcctttcg cttgtcccat gggcgggtgg tgggccaagg aggagcttag caagtctgca   4680

gcccagcccc acctccatag ggtcctgcag gcctgtgctg agaggcctgg tgctgcctgg   4740

cagagtgaca aaggctcagg acggctggct ctgggggact caggccaagc cccttggcac   4800

catcctggct tttggcaggg atgagtgagg ccctgcagag agcatcccag gccaaggttc   4860

ccactcagcc tgccccctct gcatgtgggt agaggatgta ctgggacttg gcatttagga   4920

ttccatctgg cccagcccct gaaggtcctg ggaagcaggg tctcaattct gaatagccag   4980

tggggcacac tgactgtcct ccccagggga actgcagcgc cctcctcccc actgcccccct   5040

gcagcccctg agatattttg ctcactatcc ctccccactt gcttccctga tatgtgctct   5100

gagcttccct gaaccaggat ctgcctatta ctgctgtgcc ccatgggggg ctccttccct   5160

gcctgaccca ctgttgcaga atgaagtcac ctcgcccccc tcttccttta atcttcaggc   5220

ctcactggcc tgtcctgctc agcttgggcc agtgacaatc tgcaaggctg aacaacagcc   5280

cctggggttg aggcccctgt gctcctggtc aggctgcccg ttgtggggag gggcagtgtt   5340

agagcagggc tggtcatacc ctctggagtt cagaggaaga ggtaggacca gtgctttttt   5400

gtttcttttg ttatttttgg gtgggtgggt gggaaggtct ctttaaaatg gggcaggcca   5460

cacccccatt ccgtgcctca atttccccat ctgtaaactg tagatatgac tactgaccta   5520

cctcgcaggg ggctgtgggg aggcataagc tgatgtttgt aaagcgcttt gtaaataaac   5580

gtgctctctg aatgccaaaa aaaaaaaaaa aaaaaaaa                           5618
```

<210> SEQ ID NO 3
<211> LENGTH: 5607
<212> TYPE: DNA
<213> ORGANISM: H. Sapiens

<400> SEQUENCE: 3

```
aattccgggc gccagtcccg ctccgcgccg cgccgctccg ctccggctcg ggctccggct     60

cgcctcgggc tgggctcggg ctccgggggc ggcgtccccg ccgccgggcc ccgggacggg    120

cggcgacgct ccaaccatgg cccgtgccca ggcgctcgtg ctggcactca ccttccagct    180

ctgcgcgccg gagaccgaga ctccggcagc tggctgcacc ttcgaggagg caagtgaccc    240

agcagtgccc tgcgagtaca gccaggccca gtacgatgac ttccagtggg agcaagtgcg    300

aatccaccct ggcacccggg cacctgcgga cctgccccac ggctcctact tgatggtcaa    360

cacttcccag catgccccag gccagcgagc ccatgtcatc ttccagagcc tgagcgagaa    420

tgatacccac tgtgtgcagt tcagctactt cctgtacagc cgggacgggc acaggccggg    480

caccctgggc gtctacgtgc gcgttaatgg gggcccccctg ggcagtgctg tgtggaatat    540

gactggatcc cacggccgtc agtggcacca ggctgagctg gctgtcagca ctttctggcc    600

caatgaatat caggtgctgt ttgaggccct catctcccca gaccgcaggg gctacatggg    660

cctagatgac atcctgcttc tcagctaccc ctgcgcaaag gccccacact tctcccgcct    720

gggcgacgtg gaggtcaacg cgggccagaa cgcgtcgttc cagtgcatgg ccgcgggcag    780

agcggccatg cgccaacgct tcctcttgca acggcagagc ggggccctgg tgccggcggc    840

gggcgttcgg cacatcagcc accggcgctt cctggccact ttcccgctgg ctgccgtgag    900

ccgcgccgag caggacctgt accgctgtgt gtcccaggcc ccgcgcggcg cgggcgtctc    960

taacttcgcg gagctcatcg tcaaggagcc cccaactccc atcgcgcccc cacagctgct   1020
```

-continued

```
gcgtgctggc cccacctacc tcatcatcca gctcaacacc aactccatca ttggcgacgg   1080
gccgatcgtg cgcaaggaga ttgagtaccg catggcgcgc gggccctggg ctgaggtgca   1140
cgccgtcagc ctgcagacct acaagctgtg gcacctcgac cccgacacag agtatgagat   1200
cagcgtgctg ctcacgcgtc ccggagacgg cggcactggc cgccctgggc caccctcat    1260
cagccgcacc aaatgcgcag agcccatgag ggcccccaaa ggcctggctt ttgctgagat   1320
ccaggcccgt cagctgaccc tgcagtggga accactgggc tacaacgtga cgcgttgcca   1380
cacctatact gtgtcgctgt gctatcacta caccctgggc agcagccaca accagaccat   1440
ccgagagtgt gtgaagacag agcaaggtgt cagccgctac accatcaaga acctgctgcc   1500
ctatcggaac gttcacgtga ggcttgtcct cactaaccct gaggggcgca aagagggcaa   1560
ggaggtcact ttccagacgg atgaggatgt gcccagtggg attgcagccg agtccctgac   1620
cttcactcca ctggaggaca tgatcttcct caagtgggag gagccccagg agcccaatgg   1680
tctcatcacc cagtatgaga tcagctacca gagcatcgag tcatcagacc cggcagtgaa   1740
cgtgccaggc ccacgacgta ccatctccaa gctccgcaat gagacctacc atgtcttctc   1800
caacctgcac ccaggcacca cctacctgtt ctccgtgcgg gcccgcacag gcaaaggctt   1860
cggccaggcg gcactcactg agataaccac taacatctct gctcccagct ttgattatgc   1920
cgacatgccg tcacccctgg gcgagtctga gaacaccatc accgtgctgc tgaggccggc   1980
acagggccgc ggtgcgccca tcagtgtgta ccaggtgatt gtggaggagg agcgggcgcg   2040
gaggctgcgg cgggagcgag gtggacagga ctgcttccca gtgccattga ccttcgaggc   2100
ggcgctggcc cgaggcctgg tgcactactt cggggccgaa ctggcggcca gcagtctacc   2160
tgaggccatg ccctttaccg tgggtgacaa ccagacctac cgaggcttct ggaacccacc   2220
acttgagcct aggaaggcct atctcatcta cttccaggca gcaagccacc tgaaggggga   2280
gacccggctg aattgcatcc gcattgccag gaaagctgcc tgcaaggaaa gcaagcggcc   2340
cctggaggtg tcccagagat cggaggagat ggggcttatc ctgggcatct gtgcaggggg   2400
gcttgctgtc ctcatccttc tcctgggtgc catcattgtc atcatccgca aagggaagcc   2460
ggtgaacatg accaaggcca ccgtcaacta ccgccaggag aagacacaca tgatgagcgc   2520
cgtggaccgc agcttcacag accagagcac cctgcaggag gacgagcggc tgggcctgtc   2580
cttcatggac acccatggct acagcacccg gggagaccag cgcagcggtg gggtcactga   2640
ggccagcagc ctcctggggg gctccccgag gcgtccctgt ggccggaagg gctccccata   2700
ccacacgggg cagctgcacc ctgcggtgcg tgtcgcagac cttctgcagc acatcaacca   2760
gatgaagacg gccgagggtt acggcttcaa gcaggagtat gagagcttct ttgaaggctg   2820
ggacgccaca aagaagaaag acaaggtcaa gggcagccgg caggagccaa tgcctgccta   2880
tgatcggcac cgagtgaaac tgcacccgat gctgggagac cccaatgccg actacattaa   2940
tgccaactac atagatggtt accacaggtc aaaccacttc atagccactc aagggccgaa   3000
gcctgagatg gtctatgact tctggcgtat ggtgtggcag gagcactgtt ccagcatcgt   3060
catgatcacc aagctggtcg aggtgggcag ggtgaaatgc tcacggtact ggccggagga   3120
ctcagacacc tacggggaca tcaagattat gctggtgaag acagagaccc tggctgagta   3180
tgtcgtgcgc acttttgccc tggagcggag aggctactct gcccggcacg aggtccgcca   3240
gttccacttc acagcgtggc cagagcatgg cgtcccctac catgccacgg ggctgctggc   3300
tttcatccgg cgcgtgaagg cctccacccc acctgatgcc gggcccattg tcatccactg   3360
cagcgcgggc accggccgca caggttgcta tatcgtcctg gatgtgatgc tggacatggc   3420
```

-continued

```
agagtgtgag ggcgtcgtgg acatttacaa ctgtgtgaag actctctgct cccggcgtgt   3480

caacatgatc cagactgagg agcagtacat cttcattcat gatgcaatcc tggaggcctg   3540

cctgtgtggg gagaccacca tccctgtcag tgagttcaag gccacctaca aggagatgat   3600

ccgcattgat cctcagagta attcctccca gctgcgggaa gagttccaga cgctgaactc   3660

ggtcaccccg ccgctggacg tggaggagtg cagcatcgcc ctgttgcccc ggaaccgcga   3720

caagaaccgc agcatggacg tcctgccgcc cgaccgctgc ctgcccttcc tcatctccac   3780

tgatggggac tccaacaact acattaatgc agccctgact gacagctaca cacggagtgc   3840

ggccttcatc gtgaccctgc acccgctgca gagcaccacg cccgacttct ggcggctggt   3900

ctacgattac gggtgcacct ccatcgtcat gctcaaccag ctgaaccagt ccaactccgc   3960

ctggccctgc ctgcagtact ggccagagcc aggccggcag caatatggcc tcatggaggt   4020

ggagtttatg tcgggcacag ctgatgaaga cttagtggct cgagtcttcc gggtgcagaa   4080

catctctcgg ttgcaggagg ggcacctgct ggtgcggcac ttccagttcc tgcgctggtc   4140

tgcataccgg gacacacctg actccaagaa ggccttcttg cacctgctgg ctgaggtgga   4200

caagtggcag gccgagagtg gggatgggcg caccatcgtg cactgcctaa acggggggagg   4260

acgcagcggc accttctgcg cctgcgccac ggtcctggag atgatccgct gccacaactt   4320

ggtggacgtt ttctttgctg ccaaaaccct ccggaactac aaacccaaca tggtggagac   4380

catggatcag taccactttt gctacgatgt ggccctggag tacttggagg ggctggagtc   4440

aagatagcgg ggccctggcc tggggcaccc actgcacact cagggccaga cccaccatcc   4500

tggactggcg aggaagatca gtgcctcctg ctctgcccaa acacactccc atggggcaag   4560

cactggagtg gatgctgggc tatcttgctc ccccttccac tgtgggcagg gcctttcgct   4620

tgtcccatgg gcgggtggtg ggccaaggag gagcttagca agtctgcagc ccagccccac   4680

ctccataggg tcctgcaggc ctgtgctgag aggcctggtg ctgcctggca gagtgacaaa   4740

ggctcaggac ggctggctct gggggactca ggccaagccc cttggcacca tcctggcttt   4800

tggcagggat gagtgaggcc ctgcagagag catcccaggc caaggttccc actcagcctg   4860

ccccctctgc atgtgggtag aggatgtact gggacttggc atttaggatt ccatctggcc   4920

cagcccctga aggtcctggg gaagcaggtc tcaattctga atagccagtg gggcacactg   4980

actgtcctcc ccaggggaac tgcagcgccc tcctccccac tgccccctgc agcccctgag   5040

atattttgct cactatccct ccccacttgc ttccctgata tgtgctctga gcttccctga   5100

accaggatct gcctattact gctgtgcccc atggggggct ccttccctgc ctgacccact   5160

gttgcagaat gaagtcacct cgccccccctc ttcctttaat cttcaggcct cactggcctg   5220

tcctgctcag cttgggccag tgacaatctg caaggctgaa caacagcccc tggggttgag   5280

gcccctgtgg ctcctggtca ggctgcccgt tgtggggagg ggcagtgtta gagcagggct   5340

ggtcataccc tctggagttc agaggaagag gtaggaccag tgcttttttg tttcttttgt   5400

tatttttggt tgggtgggtg ggaaggtctc tttaaaatgg ggcaggccac acccccattc   5460

cgtgcctcaa tttccccatc tgtaaactgt agatatgact actgacctac ctcgcagggg   5520

gctgtgggga ggcataagct gatgtttgta aagcgctttg taaataaacg tgctctctga   5580

atgccaaaaa aaaaaaaaaa aaaaaaa                                       5607
```

<210> SEQ ID NO 4
<211> LENGTH: 91089
<212> TYPE: DNA

<213> ORGANISM: H. Sapiens

<400> SEQUENCE: 4

```
ccgctcttgg ccaggtgatg agcgccctgt tcctggaggt atgtagaaca cgcatttgaa     60
ggcgccaagg tacaagggat tcaggcatcg gatgggacag aggccgggtg tccctgggtc    120
accgtccctg agagcgctgt acgggagcta ggcgtgggcc atgagcgtgc tcgcctggca    180
gtgttggtgc ccggtccgtg gagacgtccg tgggcgtcca gacccagccg cggggcctca    240
tggcggggag gatgcgggag cgggggaggg gcgcgccagg gctagcgggc ggccggaccc    300
gctgcagcac ccgccgtggc cagcagggag cgccgcgaga ccgccgaacc cgcggccggg    360
cctgacgtca gcgccccgct tgctccggct cgcgctctgg actcggcgcc agtcccgctc    420
cgcgccgcgc cgctccgctc cggctcgggc tccggctcgc ctcgggctgg gctcgggctc    480
cgggggcggc gtcccccgcg ccgggccccg ggacgggcgg cgacgctcca accatggccc    540
gtgcccaggc gctcgtgctg gcactcacct tccagctctg cgcgccggag accgagactc    600
cggcaggtaa gcgcgcggcg gccggaccga gcctgccccg ccgagcctcg gggcccgtgg    660
cgtagctcgg aagaaagtgt gagtgttgag tgaccgggcg ttacgagcgt gctccctgtg    720
tgtgtctgag cgtaggatgg gcgattgtgt gcccggggtg ttgcgtgact gcgaatgttg    780
tgtgtccgtg agttctgtgc gcaagaaaag gtgatgtgtg tcggcgagta tgttggggggt    840
gaatgttgtg tgcatcgagg cattgggtgt gcgctgagtg tcttgtgggt ctgccagtgt    900
gtagtgtttg tgtggccaag tgggttgtgt gtgcatctga gtttggttgt gttgcgggag    960
ttgtatctgc taatgtgttg catttgtttg cattttgtat gcctggccgg gagtgctgtt   1020
tgttttgtgt ctgcgagtgg gttgtgtgtt tgtgttatgc ctgtggccaa gggtgctctc   1080
tggatcccgc ctgagtgtgg atccgggaac gcgtgtgtgg cgtgtgtgct tttgagatcc   1140
gtgtacatgt gtgaaggcgt gggaacgggt ccggaacgtg tgtgtccgtg cgctgtgtac   1200
gtgtggggag tgtctagggt atgtggtgtg tgctgccggg ggccgcgtgg gtccgagtga   1260
atgccaagtg tgccgggaat gcgtgtgtgg gagcgagtct ggaacggatg tgagtgtgtg   1320
cgaatgtgtc cgtgtgtgct ggctgcgcgt ccaggaatgt tgcgagtgtg gagcgcgcct   1380
gggccgcggc tgcgagtgtg ccctggtccc ggggccgccc gagggggcgg tggcaggacg   1440
tgtgtgcgcg cgtgtgcgtg tgcgcgtgtg tggcgcgctg ggccggaaca agttgtcgcg   1500
gcggcgcccc ctgggctgcc cgggtcgggc agggcccgag gctcagggga ggaccgggcc   1560
ccgcggccgc cgcctcgggc atgtcggact gtttgttgtt tcgcaagttc cgcgcggcgc   1620
tggcgggcgg ctgatccgag gcggcgccgg ggctgcgggg cgcccgggcc agcgggcccc   1680
agcgagggc cggcgggcgg gcaggggagg gccggaccgg cgggcgctcc tgcggtggcc   1740
gggccgcggc tgcgccccgg gcggccgggc gggggctgtc cccgggctgg gctgcgacgt   1800
ccgggcgcgg gcagggcctg gctcgccgcc gggggacggc gccccctccc ttggcgcgca   1860
ggacgcgcgg gggacgcccg ggcctcccgg gacactccct tggtggagcc tgcaactttg   1920
tgcggcctcc cggccggccg ggaccgccag gtgtgtgctt gagtgtgagc gtgagtgtga   1980
gcgtgtggct ccgcgcttgt ctgctgtgtg gtcgcgttct ccgggtgtgt ttcggagtct   2040
ggtgtctttg gtgtgcgtgc gcgtgtgtgt gtgcgcgcag ctgaatgtat gtatacggag   2100
cctgtgtttg tgtgtccgtg tgctcgtcgg agtgtggacg gtgtgtcgga tgtgtgtgcg   2160
tgcgcgtgtt ccacatccca ccctgaggcc tgggatccta gaccgcggcc ccttcccgcg   2220
gagtttcggg gccctgctcc gggtgacctc ccccgccctc gccaccggcg gggctgctcc   2280
```

```
gcgggctccg ggtagccggg agacgcccgg ggcgggatcc gagccgagac acgtgctgga   2340
gcggagccgc ttcctcacgg tcgccagccg cagacaactg acctccccgg catcgcgttc   2400
gcggccctgc tgctggctcc ggtgtctcgg gccggaactc ctgtggctcc agcgttcgcg   2460
ccggccactg gccagcgctt gggcctcgcc ctgcagctcc ggggccatag ggcacagctt   2520
tagctttgac ctccccgttc ccgaaaggac gcccaaggcg acctcccacc ccatcctccc   2580
caacttctcc cccatgtcct gcggcaactt tgcctccctc tcccaccgtg aaatcaaacc   2640
cgcggggttc tgtatgcgcc ccatccccgc tcctaccacc atcgctttga tttcaagaac   2700
actcacaagc cccaagccct gccagcagga ggactgtcag gaactgaagt ttgggagtga   2760
ggcctagagc aggttactcc cattcttgat gcctcagttt cctcttctgc ctcatagcca   2820
tcatgataat ggtgtatggc acttttggta gataccaagt accttgtaaa gtaaggctct   2880
gtctgtgagt gccagggaac aaaaaatgga tttgagagtt gttgcaaagc cccagacaga   2940
ggctgtgatt taaagctggg gtattaggtg tcaaattctg cctctgctac ttgctattca   3000
tgtgatgtct ggcaaatcac ctcacttgta aagttcctgg ccccctttgt tattcttaga   3060
gatgaactca gaagcccaag tagaatagat gtgatacccc ttgtccccag tctggacaga   3120
gtcagcccag ctccctgaat ggctccggag cttccgggta ggggcggtgt gtgatgcctt   3180
ctcagccttg caaacctggt agttatttat tctgctgtgt tcttgctatt ttgtcctttt   3240
ggtcgcagga gttgtggacg gcaggaatga gggagtggct gcccagtggt ttcaggttgg   3300
gcaataaagg cttgtctggg catccctccc ttttccctgg ggctagggga ggggacttag   3360
caggaagcag tgacagtggc cgaggtgggg acgctgagct cctggacagc ctgctgccca   3420
gctctggtgt cagaaaaaac ctagggcaag catcgtgctt gatggagaca ggccaccatc   3480
cttccatgat tttcatcagc tcagctgggc atatggggtg gcctttccat gcaggactgg   3540
gttggccaga gttgcagggg gtaccttgtg ctcctccttc ctccccctcc cccctttcc   3600
tagttgccct cctgcatcct ggaacgtcct gtctgccctc tcagagactc tttcatctgt   3660
ctccttctgt ccgtcctcag ctatctttca cctgcaggaa gactccagcc tcctccttcc   3720
ctctttccct catggtgcca gggatctttg taaagtacat tttaactcaa agggtttaaa   3780
accctttgaa ggctccccat tgccttcagg gtgaagtcct tatcccttgg ccctgttgct   3840
ggctctagct cctgcctgcc tgtccagctg catcttgttt tgtgtcactg cccctttgcat   3900
cctatgatct ggccagcctg accttcttac caaagaccca aatgcccaca gcctgctgtc   3960
tcctctctgg gcctttgggc aagccgtgct ttctctgcag aactttctaa ctccagcttt   4020
ttgctggtga actcctgcaa cttgatgggc tctcagctgt aagcatcatc cagtccctga   4080
agccttcctc ggtgatgccc tgtcctagcc taggaagtcg gggggtgggg gtcaattgga   4140
tttttacata gcattgtaat tattgtaatt acagtttatt agtgctgtct cccttaccag   4200
actgagagct gaggacagag actgggtttt tagtttactt ctgaatctta gtgccaggta   4260
caaggcctgg cccaccgggt ctgaataaat atatatggcc tgaaagaata aagtttaagg   4320
gggccaggtt cagaggtgga gatgccagat gggggtgcac tgattccact gaaggtagag   4380
attgaagaac caggtttccc tccaggaatc tggaaaattc ctggagggtg ggggatggtg   4440
ttatgttgtg aaaaggccat gttgagagtg tcatctggga gctttgagtt ggggaggttg   4500
agtccctggc aagagactga agggaacggg cctcctgcct gccagcccct cccccaggct   4560
ctggccccac ccctagcagc tggcagggcc cttccagccc ccagtctcag gcttttgtga   4620
```

-continued

```
tggggcctgg cagttggtga gacgttgagt ctcaacggtc tgtgtgagtg gctggggagg   4680
agggagggag cccgcagggc cctgtgttag gagagggagg gaagcttcct ggaagaccct   4740
cccttagtcc tcagtcctag atcctagggt gggcgggtgg ggtcacagcc tctgttctca   4800
ccgcttgtgc accggaggga agggaggaga actgcatccc gtggtggccc tggcagatgg   4860
ggttggggag gctggctgag gtgtgtgcag atgtgactct agcatctggg cagtcagagt   4920
ggggggtgtg tagggattgt aactaggggc atggacacat gtgacctgtt agggtgtcta   4980
gccatctggt tatcgtgtgg tgtggcagga tctgagtttg gagtagggag gtaaccagct   5040
gctttgaccc ctggggagcc tggtgctaag ggtgtctggc tatccaagta tcacattcct   5100
ggagttgggt gcagagctat ttggatgggt ggtgtctcgc tatctaggtg tggacaaccc   5160
agtaccagca tgtgggagga tcagggtgtg cagacagagg ctatcccagc atccctgggg   5220
ctggaggtgg gtgtatccat gtgtctggga gtcctcaggt tagtgggtat ttataagtgg   5280
ggagtgtctc tgtgttgtgt ccaggtatgg ggctggccag gtgcctgagt gtctggttgt   5340
aggggtcccc aagtgtccgg gtatctgagg gtgggggtat ctgtgtatga aacaacaggg   5400
acccagtcat tgaagtatcc agttgttagt gagtctgggt gtggggtgcc atgtgtctat   5460
ttttttttt tcttcttctt cttcttcttc ttcttttttt tgagatggag tctcactctg   5520
tcacccaggc tggagtgcag tggcgtgatc ttggctcatt gcaacctccg cctcccgggt   5580
tcaagtgatt ctcctgcctc agcctcctaa gtagctggga ttacaggcgc acgccaccat   5640
gcctggctaa tttttgtatt tttagtagag actgggtttc gtcatgttgg tcaggctggt   5700
cttgaactcc tgacattgtg atctgcctgc cttggccttc caaagtgctg agattacagg   5760
cgtgaaccac agcgcacggc cttttcttct tttttattca gatggagtct cgctttgtca   5820
cccaggctgg agtgcaatgg catgatctcg gctcactgca acctttgcct cctgggttca   5880
agcgattctc ctgcctcagc ctcccgaata gctgggatta caggcacccg ccaccatgcc   5940
tggctaattt ttgtattttt agtagagatg gggtttcacc atgttggcca ggctggtctt   6000
gaactcctga cctcaggtga tccacctgct tcggcctccc aaagtgttgg gattacaggt   6060
gtgagccact gtgcctggcc tcatgtgtct atttgtatgt ttagatgtgg aggtgccctt   6120
gtgacctatg gtggtgtcca tgtatccagg atgtgtccac aaggggtgtg gacgtgttgg   6180
gtgggaatgt cctggtggct gtacccaact caacctctgg tagccccttc cctgggactt   6240
gcctcctgat cgctcttcag actccaaagc cagaagcctt ggaaggggcc ccgatagttc   6300
tgtttttcaa cggtcagcct agagctgtgt tatctaatag aaccttctgt ggtgatggaa   6360
attgtcctct acctgcattc tccaatacgg tggctcctga gtcatgtatg ggtattacat   6420
ttaaattaat taaaataaaa attcaatccc tcagttgcac tagtcagatt tcaagtcctc   6480
aagagtcata tgttgctagt ggctctcatt gtactggtta atgcaggcag agaacatttc   6540
catcctctca gaaagttctg cagacagcac tggtctagag gcatgaggcg gcctgcagca   6600
ccttcagtga gtcctgggca tctctgggag gggaattggt ctggatggac catgactcag   6660
tggctcttga caaaaggttt tgttcaatcc aggccccttc tctgcagcct tattagatct   6720
tgcctggact attgcagtag cctggtagcc ttcttggcct ctactctgcc tgccatcacg   6780
ctctcggttt cttttttttt ttttgagatg gagtctcact ctgtcaccca ggctggagtg   6840
caggggcacc atcttggctc actgcaacct ctgcctcctg ggttcaagca attcttcagc   6900
ctcagcctcc caagtagctg ggactacagg cgcgtgccac cacgctcggc taattttttg   6960
tatttttaat aaagacgggg tttcactgtg ttagccagga tggtctccat ctcctgacct   7020
```

-continued

```
catgacctgc ctgactcggc ctcccaaagt actgggatta gaggcatgag cccccgggcc   7080
cggcccaggc ttttggtttc taatgcttcc accaccctgt ggctggaata agcttctaag   7140
gcagacatag gatgctgcca ctcctttgtc ccaagctgaa ggctccccag aactcagggg   7200
acaaaaccca aaccctagca tagcacatga ggccctgcat gaccagccct ttctttctga   7260
agcagcttca catgatgcct ttcttccctg atcccactcc tgcctatccg ctgtctgctc   7320
caaatcacca ggcaaattgc tgatccagga gcctgccatg ccagttcaca cctctctacc   7380
tttgcacaca ctgtgcccct ccctacttct cacctcgtgg tgggggtggg ggatctacct   7440
acttgttcag ccttcacagt tcagctccat tgtcactgat gcagcgaagc cttcccagcc   7500
ctctcccggt gcagttggtg aaatttctcc catagtggac gtctgacaat gtgctgcggt   7560
tttccatctc ctttttccac taggctggga gcccccaggg gctgagctgt gtctttgtca   7620
tctgtggtcc ccagggccta tacgtgggag atgcccacta agtggctgca tctcgatgcc   7680
tctgggtgca cagggaaggc ttggaggggt gaatgcagga gctggggttc tgcagcacag   7740
tcatgggtgg gctggctatg cctcctcctc tggctctggg ttgggggctg ccatttcctg   7800
cagaatgact gtgggaggac ccctgagggg gacagctcag aagatgctgc ttccagatga   7860
cgcaggaggt cttgggcaga ttcccaagat gcaaaccaca agaccttgtg atgactcaga   7920
agggacaagg agaaaggggg cttggagggc cgctgaggct tgggagtttg agggcagaag   7980
ctggggagaa agattgagat ggggctgtta ggaaggggag atgctgagga tatttgacag   8040
ggcaagatta aagctagggg tggggtgaca gctcagcccc cgggggctcc cagactagtg   8100
gaaaaaggag acggaaaacc gcagcacact gtcagatgtc cactgtggtg ggtgacagct   8160
gaggcctggg ggaccactgg cggatagaag atagctggtg ggaaagatat acctggggga   8220
tgggacagct gacagtgaag ggacaggcgg tattggggga acaactgagg gttgggggac   8280
aggtggatga tagaacaagg agatgtgggt gataagataa gaggtggaga taagaggtga   8340
caactgggag ctatcagaaa cctagtggat aggacaggtg agtctcagct gagagtggga   8400
aatacattgc ttagaatgtg tatgtatgtg tgtttacagg agcgtgcatg tggacttgtg   8460
gctgggcatg cctgtcaata tgtgtttgtc tagcgtgtgg tggttaagag catgggttca   8520
gggcccagac catctgggtt ctaatcctaa gcccaccact tctagctgtg tgatactttg   8580
gtaagttact gacctctctg ggcccttaga gttctcattt gtggaatggg gataataata   8640
ggacacactg catgcgtttg tcatgaggat atgttttatg gttatgatta tgtaggttag   8700
aacaggtcct gcacatagta agcactgtgt aagtgatcac tgttatgatg tgtgtatttg   8760
catgcgtgcg gtcatcctgt gtgcccagaa aagtttgttc ttggtttctg atgaagtcca   8820
ggcctgggag ggagtaatag tggtggggac gggggtggtg gttggggagt gcctagccag   8880
gttgattgag tctggctctt ctctgacatc ctaacctctt gttcatccta cttcctgctc   8940
accctgtccc agggccttat ccaataatag gtctttctct ctatctctcc tctgtcctgc   9000
cctgggctgg gggccagggg ctgtacttta attgtctgag agctttacca gcagaatttg   9060
aattcattgt tttcctgcca gcatgctggg attctgctca gttataatac ctggacaatg   9120
tgctcgattc tagatggcct atcctgtggg tggcagtggc ttcagccttt gcccttggag   9180
agtcactggg gtggaagatg ttggagggag ggagacaagc cagatgagat ttcggccccc   9240
aacttgtggg gtgagccagc gtggccgggc agagctgtag gtagagagtt ttccagggat   9300
ctgagctccc ctctcctcca gtgcatcaca gggaggcatc atgaccctcc cagcaacact   9360
```

-continued

```
gttgcagcgt gccaggctct ggactgctct ggatgtgcac tgtctgggat tcctgggtcc   9420
agcctccttg cacagccctg tgtctcagcc ctctacttca ctgggattgc tgcattgcat   9480
tgagggtgtg cgttctcctg agtttctgca tgctctgcct ctgcattgtc ccattggacc   9540
gtgcctccat cctgccatga tcctgccatg gtcctgccat gtgtgtgtct ttgctgctct   9600
cttgtatact gtgtcactct gctggatgtc agtgttgcat tgggaaggtg aattctcctg   9660
ggtttctggg cggagctgct cacactgcac cactgtctga gatcaacaca tggttttctg   9720
tggccacatt gcatgtttgt gtcatagagc atttatattc tgcaccccat tgcctcacca   9780
ggcagtctac attgcattgg gcacatggac tcttttgggg tttgggcata gctcctcgca   9840
ttgcagcact gcaccgtgcc aacagatggc atgctaccac aacattgcat cttggcatca   9900
cacagcatct ctgtactgca ctgcactatt gcatggacgt cagtattgca tcaggactgt   9960
gaacttttcc tgagtttctg ggcatggccc ctctgcattc cacagttgca ttgtaccaac  10020
agtgcacttt gccccatata gcacttctgt gcatgtgcac tgctttgctg cactggatat  10080
gtgcctcatg gcccagccct tgcactgcac cactgctgct gaaacgctgc ccctatggtg  10140
tcctggcctt tcacgctcct accaccatgg tatctgtagg ctggcgtcct tttccaggtt  10200
tttgttgtca gccctacgtg aacaacatct ttgcattgag tgtcctcact gccccacgtt  10260
gcacatgact cagggagtct atatctatag tacagcttgg gaccactttc ttgggcttca  10320
ggactggctt aggtttgcaa aggcagcacc actgcacagt atctgacatt gcattcgtgc  10380
actgcacagg attactgccc agggcctcta ccctgcaacg aacctgttca ctgttgggtt  10440
gtgtgcactc taccggattg cgggacccag agcccttgcg ttgaatccac tggttccaca  10500
cagcatctat tttttttttt ttaagatgga atctcactct gttggccagg ctggagtgca  10560
atggagcggt ctgggctcac tgccacctcc gccccctggg ttcaagtgat tctcctgcct  10620
ccgcctcctg agtagctggg attacaggca tgtgccacca aacccagcta atttttgtat  10680
ttttactgga gacgaggttt caccatgttg gccaggctgg tctcaaacct ctgacctcaa  10740
atgatccacc tgcctcggcc tctcaaagtg ctgggattac gggcatgagc tactgcgccc  10800
agctccacac agcatcttaa ttgtactcca ttttgtgcca cttcctaccc atgcctcgag  10860
tctgcacata ctctgttcct caggactgta tttattgggc ttatatgcta ggctgggttg  10920
ccgcaccctg cagtttcttc ttcactcact gccccttttcc catcccctta tctctctgtt  10980
gttctgtgtg cctgtgctgc atgtctatgc agggcacaca cccttcccct gagaatgcat  11040
gaagcttgaa ctagtaaggc ttaaacttac catcttggca ttcctccata cacctatcac  11100
gtagcactgg gtgccagccc agtgtaccac taaatgcact gcagtggcgc ggtgtgcctt  11160
gtgcagctct gggtcatgcc catgatggat gtggcacttc catggtgcat catggccctg  11220
gccagttctg ccatgctgta ccagatgtct gtaatgaggc ctgtgcacac tgtgggctct  11280
gctccctgca ttgtataaca gtattctgtc tctacactgc aaagctgctg tactgcaccc  11340
tccacacact gcactgtggc acagcagagg cctctctcca tggaccttta tgaagtacag  11400
atcgtcacac tgctcgggtt tgtgcacagc cccatgcccc tctactctat actctgtctt  11460
cgtatgtcgc agggtgtctg tggggcagat ctgtgaactc tttgcaccac tgcaccactg  11520
cacaacatag tcctccattc ggcccttttc ctctgtctgg catccagccc tggcctgtgc  11580
cttcccctca tactgccagt gtggcagctc tactgctaac tctgggattt gcagcacata  11640
ttgatcaggg agatggggag tgggcctggc ataaggtccc ctgctgtact tggtttcctt  11700
ccattctccg tggagatggc aagatgttgg cattgtcagg ctgtgtgttg gctctgtggg  11760
```

-continued

```
tggtgctagc tcaactttcc ctgtggccca gccctgggcg atctttctgg ttgcagctat  11820
ggtgactcct gggtgattag aaaatgggca tactgctccc agccctgact acaattaatg  11880
acccatcagt ttgtcagggc tcttcgggca gctctgggag cctcagctta ggtctagatg  11940
agttgacttg ggcaaggaga gtagcaaggt gggctgggcc gggcctctgg gctggagtca  12000
tggtcctaga gctgggtgtg gttggtgagg gtcagactag ctgggatcat ggggtcaata  12060
agtccaggca ctgttggcta tacacagggc ttgggatggg gttcaaatgc atgagacgtg  12120
gtccttgacc tcaggcaggg aggaggtagg gattagacag gcctgagatg gagctgtagc  12180
tggggtggag aacccaggat ggggctgggt taggcaagaa agtcaggggt gagtccagtg  12240
ttggttccag gcttgggctg ggctgctgag aataggggta caaccttgga tgatgaaata  12300
gtccagtatt gttgttgggg ttgtatttga attcccccac ccacaactgg gcatgtacct  12360
gggcttgggt gaaatcccag cccctaaatg tgcaacctgt tgggaaaagt tttgcttctc  12420
ctgggaccac tcttgggaat tggatgttct attgacaaac caaagggcag aaaagtctca  12480
ttgcaaacag gctctgtttg ccaggtgtct tcagaaaata ctggttgcag ctgcagccgc  12540
attgggcatg gagtgctgtt ccctgtctgg tgtgaggaaa gtctggtgca cagtgcttgt  12600
gttcacactg acacatacac gtatgcacaa ctcccatcta ccttactgca cacacccacc  12660
tccccettag gtgcaggctt accactaaat atgccctgta cctttgcttg taaatgcacg  12720
tctatacacc cacggcttca cagcgcctgc ccgggagacc tcccctttcc gacacccatg  12780
cccaccctca tgcacctctg ccccaagatg actcttgctc acgtgcacac tcacgcaact  12840
gcaaccggtc atctgacctt agcggtcccc actctcattt tacaggtgag gaggtaagga  12900
ttcagagagg gcaagtcacc tgcccaaagt cacaaaggga cttagaggct cagtgggaaa  12960
aagatcccgg tcttccgcct cccatttgaa tacttgaaac tcagtaccag gctgtcctgt  13020
catcttagag ccatgagtgc acgtgtgcac acacacacac gcacacctgc acacactcac  13080
acgcacacct gcatgtggac acatgcatgg ggaggtgtgg agcccctccc accagggaga  13140
cccctcccac actcctccag aggcagctct gccccttaca tcaccccatc ctgagcccag  13200
ccggatgtgg ctaaaccatc cccctgcctt cccaaattgt ggctgacggt tgctcaggca  13260
accgcctgcc agactgggga gattagctga ggaatgtagc tgggccagtt tgaactgagg  13320
ctgggggagc ccttgggggt cttgggttga ttcaattcac cctctcaggg aggcctctgt  13380
agagatgggg tgcccaaggg caggcattct ccctgttccc agtctgaggc tgcatcccca  13440
ggcttggccc aggctgcaga aagggagtgt gtgtgaacac tgagcgcggg gctcagggca  13500
tatgtgtgtt gtgtgctgtg cacctctctg agtgtgattg gagggtgtgc cgtttacatc  13560
ctggaagggg acttgaggcc cctgtcctca ccagtttctg acatctgact ctggacccct  13620
tggtggcttg gtcccaagat ccctctggat cctgctgtgc tctctggaga caccacctgc  13680
cctactcatg gcttatagga tatatcattt atctcatctg aatccaggat gagataaact  13740
ttcctactca aacacctact gtggcttctc aattcaaaat gaggcccagc tcctcaccct  13800
ggcgttcagg gtcctccatg attggcctca acctcccttc cctccagtca tagctcccat  13860
ggctttagcc aacctgggct cctttctgtg ccctggacaa actgtgttta ttgaccacct  13920
tgctttgctc ccctgggtct tttgccacaa atccttccac ccatctctac ctatccttct  13980
tggctctgct tagatgccgc ctcttccagg aggcctttcc cctctacctg gccccctccc  14040
ctggaccccc tcttgtggcc ttgactcttc ccttattccc tcattccctc ttcctcaccc  14100
```

```
tcactgggac taggaggtcc ctgagggcag ggcagagtct tcatcatcct tgtacctcta  14160

atagtgccag cctgggacct gctttgtact ggcagggaaa aatcccctgt gaatgaagct  14220

gaattaacac ttatggccag cagaagggca ggctttgttt tgtttgtgcc cagtctcctg  14280

gaataaagat aggaggttta agtctgagct tctgcacatt gtagctgcat ggccttgagt  14340

aagcagctgt atctctctga gcctgtttta atctgtaaat taggaataat aatagtacct  14400

aataaactaa caataagaca aaaataatac tacctacctt ctgagttgct gaggattcac  14460

cggctcaggt ggtcatggtg gtaattcaca gccccttcat agaggtattg atgtgtatat  14520

gtgcatgtct gtgcccatgt ctgtgttgat ggagtcaaga aggattcctt gctaccattc  14580

ttgctctgaa ctcaaagtcg gatttagtgg cctccagcag gagttgagtc tctagcagag  14640

ctgggacttg gctttggggc ttttggctcc tagctgacca ttcccatctc aagggaccag  14700

gggaaggggt gagggtgggg ctctccttag ggagcctgtc cccagagatg ttacccacta  14760

tgagctggag ctagaactgg gtctggccca gagacacagg tctagagacg gacatgggtc  14820

agggagaggg agtgaatctg gttaaggaat cactctgagg ctgggtacag tggctcatgc  14880

ctgtaatccc agcactttgg gaggccaagg tggaggcacc acttgaggcc agaagtttga  14940

gaccagcctg gccagcatgg tgacatcccc atctctacta aaaatacaaa aacaagctgg  15000

gtatggtggc acgtgcctat aattccagct actttgcagg ctgaggcacg agaatagctt  15060

gaacctggga gctggaggtt gcagtgagcg agatcatgct actgcacttc agcctgggca  15120

acagaatgag actctatctc aaaagaaaaa aaaaaaagga atcactctgg atgcggtcag  15180

tcagtcagcc catccagagt gactccttgg aggtcacctt ggccggggtc agttgtaggg  15240

gtcatttggc agaggtcagg ggtcactgtg gctggggtgt gcaggtctgg ggtcagtcag  15300

tctgatggtt attctggccg aagtgagata gtctgggggt catctgtatg aggcagaggc  15360

cactttcaac agggacagtc agctgggagc caggctggct gaggtcggcc tatttggggg  15420

tcaccaactt ggatcagtct ggctggggat cataggactg ttgtcagtct atctgggggc  15480

tcctgtgact gaggtcaggt ggtctgggtg tcactctgac caggttagtc agtctgggag  15540

tcctggccgt tcgtgtggcc tggctcagga tgaacaagag gaagccaagg ggctggcact  15600

cccaggctct ccccagggtg gtgagtgaga catcagggca gcggctttgt tacttgtgaa  15660

ggaacaggaa aggcctgaac cccatccagg gctttagatc ctgggcttcc ctttctggca  15720

acccctctac ctcaaggagg ccttggctaa gagccttagg gcaggcccag ctcaagctga  15780

agtcagctgg cctcctcctc caggaagtcc tccctgacca ccatgctctc tctctgtact  15840

tgccatgttc tttctctctg ctgcactgtg ggtctttttc tacaggggaa gctgaggccc  15900

tccaggtaca gatggggtta atacccacct cctacaggca atagggtatg atgctgacca  15960

gggattttca aacaaagagc caaagagctc agccaaggtc ctgcctcagc tctggaaaga  16020

gtcttctgtt acttcatccc aactgcttgg tgccatcctc acacccacat ctcaccattt  16080

caggagaaga ccgggagccc ccagcagtga ggagcccctt tgtgcctggc tcttctgggt  16140

gtgtttttct tttttctttc ttttttttt ttttgagaca gagtcacact ctgtcaccct  16200

ggctggagtg caggggtacc atctcagctc actgcaacct ctgcctgctg ggttcaagtg  16260

attcttctat ttctgcctcc caagtagctg ggactatagg catgcgccac cacacccagc  16320

taatttttta atttttagta gagatggggt ttcatcatgt tggccaggct ggtcttgaac  16380

tcctgacctc aggcgatctg cctgcctcgg cctcccaaag tgttgggatt acaggtgtga  16440

gccaccgcgc ctggcctggg tgtgtttttc atgtgctact tcacatcatc cgcatcaccg  16500
```

-continued

```
cctagaggag ttgcagctgc agatgaaaca gtagagcctc ctaaaagtga agtcgcttgc  16560
tgcgtgtgaa gatgcctagc actgggcctg tgacatagca ctcactcccc aggtgctgtt  16620
gtttgggaaa agctctctca aacggtgttt ttcctctgcc ctcccaccac cacagcagca  16680
gtcatcaaca caggaggcct ctgtgaccaa atgtgtgggg gcttctcccc accaccaagc  16740
aagcaattaa ttctgtagca gacaccaggt gggtgtcctc caattcagtt ctagcacaag  16800
agtcagatcc catgggttga gggctcagtc cccatgactg cctcctcctc cagacaccag  16860
tcgcaagtct gggcctccag aacttctggc cgacccgctg caggttgggg ttcccacgac  16920
cccctctttg agtttgatta atttgctgga gcagctcaca gaactcaggg aaacacatta  16980
actggttaat tataaaggat attgcaaagg atacagatga agagatgcat agggtgaggt  17040
atgggagaag ggacatggag cttccttgcc ctttctggac ccaccatcct ccaagaagct  17100
ccatgtgttc agctgtctgg aagctctccg aaccctgtcc ttttgggtat ttacggaggt  17160
ttccttacat aagcatgatg gacaaatgtg attgcacata aaacacctga tctaaaccca  17220
gcaaggcctg tctgcttaga ctttacttgg cctttccgtg gcattccttc ctctagggta  17280
tggggcagga ccctctctgg aatgacccat gattagatta gagccctgcc ttggacaggt  17340
gaaaggagga caggaatagg tcagagagaa attttgtttc ctgaggcctg tttctgaggc  17400
ctaaagtgtc caacattata acataagact gtacaaaggg ttttatatat ataaataaat  17460
atgtattatg ttgtgcaaaa gtaattgctg tttttgccat tactttaaaa aaatggcaaa  17520
aactgcaatt acttttgcac taaccaaata tatgtaaata tcacaactat ctatacctct  17580
ccctcttctt cttgagattg ggaagcagct caggtctgct ccttctggta tcgaaacctc  17640
ttttggtggg aagcttggac ttcatcatct gacccacatg gattcaaatc ccacctctgt  17700
tccctagtag acttgcatgg tacacataag agctgctatt tcctgagtgc ttaagtatgc  17760
taggcgttgt gctaagtggg ctactacatc aaatcctcaa caagcctatg tgcagatagg  17820
gaaacagagg ctcagaaaga gaagccacct gcccctggtc acaaggtttg gcaaattgca  17880
gtcaagattt gatcccaagt ctgtgatgcc aaagcccact cattgatcca ccacgtggtg  17940
ctgtggacaa atcccttcac tcctcagatc ctcagtcaca tcatctgtca aatcgggagg  18000
agtaccagtg gctggcaggt acccaggaca gggtctggca tggtttgcgc ttgcttcctc  18060
gccacttgct tgggcatttt cctgggtttc tgatgcctca ggctcctgat ggggctccaa  18120
acactaaggt ttgggagtga gtgccaggga gaagcttgca attcctttct gaaccaatag  18180
tgttctcagg tttatcaggc aaccagctca ggcctttgat gaactcacta agatatatgg  18240
acctcattac caaccaaagg actcacatgt atttcaatcc tcacttcctc ccctctttct  18300
catttcaact gttagtactg gttgcaaatc atgggaagtt gcttcatcta gtcagtcata  18360
catgtgccta gtccacacat gactgtgctt ttgcatgtca cattcctgca ggcagagacc  18420
taatttggcc gactttgggc aatgactgaa ttccattgac atctgtcaag taggaaaaat  18480
agtggtgcct gactcagaac gcgtggcctg aacgaggctc tgtacttacg ccatttagca  18540
ttgtgcccgg cttgagtgga ttggcggcaa ctgttgtttt taaaggagat ctcattgggc  18600
tggattatgg catgcatggt cctgccaggc ccagggccca ctgtctgtcc tctatgggaa  18660
gatagagggg caggtgacag aacactgagt aacaatccgg agatctcagt tcaaacccca  18720
cctccatcac cagtgacctg cgtgacccta atgaagtcac tcagcctttt ggggtctcag  18780
tttccttatc cacaaagtgg agatgattct attcctgatc ttatgggttg ttgtgaagtt  18840
```

-continued

```
ccaataatat agcaatcctg ataactagtt tttgaggagg gtctttgatg gatgactgag  18900
ccagtggtgg ttggggggtc ctgggaagta ctgggggagt tggcagtgta gggacatctt  18960
ggtattggga ggggaccttg gtagagggag agggtggagg agggagaatt tcactagagg  19020
gagggagcag tgtggggaag ggcctgaaga gagggaggag ggcaggtggg cctgggtaga  19080
agggagagtg gggctaccct ccaggagccc tcctggccag cagccctgcc ttagcctggg  19140
ctaaccaggc cctgctctca cagctggctg caccttcgag gaggcaagtg acccagcagt  19200
gccctgcgag tacagccagg cccagtacga tgacttccag tgggagcaag tgcgaatcca  19260
ccctggcacc cgggcacctg cggacctgcc ccacggtaag tctactctcc atcgccatta  19320
ccccttcttc tccttccaga ggcacttcta cccacctgct gtgtgacctt gggcacatta  19380
cttaacctct ctgggcccca tctacatttg catctttaat gacatacgtg acactgaatg  19440
tggctttctc tggacactgt ctaattgtgc atgtcagcta gtttcgtgtg taaaatgagt  19500
gcaggccctc atggctgtga gctaaaactc acttccaatt actccccttg ctgcctagct  19560
caggatccaa accactccca ctctcagttc ttcctaaatc ctccatcttt gagaggctct  19620
cttcagagat tcttttctcc caaagagccc ctgaatcctg gtctctccag gacttgaaga  19680
tgctgaaaga gcagtaacac tgggactaga tgtgtataaa accttccttc ctctgccctc  19740
ttcctcctgg aagtcccaga ttcttctcga cttctacctt gctgtgttcc tatttcaaga  19800
tggggcacct ttgtcatcct gagctctgga ctgggagtca ggagactaat aatatggatt  19860
ctagtactga cttcctgctt tcatcatggc ccctagaaca ctcattccag agtcacgaag  19920
acctgggctc aaaccctgtc tccagtcact ttaccagcag tgtcacttaa cgtatctgag  19980
cctccattgt cttcactgta aaatgaggca aacaggactc catttcagag ggtcatgaga  20040
tgatgcatat aaagtacaga gcacaggggt ggcatgcagg ggtcagttat ttaattgcta  20100
tggttgaggg tctttggggg ccctgattac tagtactgct cttcactgga tgcaggatca  20160
actgggaatt aaaaaagaat gagacaaata aaggccaaat tgtcaacttt attactgata  20220
agggctgtgt cagaggacaa atcaaatggg ctttccgagt gaatcctgaa attccacagc  20280
ctgaagccca ctccctttgc cccatcacac tagtgcccag ggtgtttact gcctagctca  20340
cgtcatggct gagattgcat ctgttgtcag ggaggggcag caaagattct cagtggtggg  20400
gccaggactt gaagccacta ggagagaaga ccttcatgac ctggcacagg cgcctcctgc  20460
ggactctcat ggcttgcccc gcctcccctt ctgtgcattt gctcacactg tgcccttcct  20520
ggggcactta tctctgcctc tgcaggtgtt agtgggtatc acagtttgcc ttctctgaaa  20580
ataatctgta aaggtaccca ccatggcagg gacctcgtgt gggcctctcc atattcccag  20640
ggcccagcct cagtctgata catggttggc agtcaggtac aaggcagctg attggaattc  20700
acctcttata gtactgacca ccctgagtgc acactgcctc tcttgtcacg tgcaagcaga  20760
gacataccca gtgagaaagg ggagagggga atttagcaat tagtgtgagc cttgtgctag  20820
gtcttgagga tgtggtggtg agccagatgg acagtctttg tcctcctggt tctcacattc  20880
taggaatggg agctggtggt ggagggagaa gaaaggaggg agattcacac tcagagatgg  20940
agagaggaga aggaagagcg acagggacaa agggagtaaa tgaaagagaa ggggagggat  21000
gtagtgagcc gaggaggagg cagagggagc aggaggagga ggaaagaaca aagtgtcaga  21060
ttggaagagg gagaaagatg cacacagctg ctcgcaggga gaggagagag aagtagcatg  21120
agtgggccaa gagggagtgt gttgggggtt gagaagtgcc ccttcctggg tggggatggg  21180
gacttgagtt tagtttacta ctgccctgct gggactgatc caggagccgc ctccataggg  21240
```

-continued

```
cttctagctt acagagatga atgagatcgc ctccagcaga gtccctgggg agccctcctg  21300
gagcggggat ctgagtgagc ttgtgttggc tggcagccaa gcccgggagg aggcagcgct  21360
gggtggtttc gggtgccctt tgggaagccc aaatccccccc gccaggtcct gagccagcct  21420
agtccacttc tactccacca gtacccagcc tgggtctctg ggaagggac aggctgcctt  21480
tctccaggtt ggaagtcaag gggatttgta ttccaggaat ttagactcag ggatgggggc  21540
tggaagggaa gttggaatcc tttcattcaa tctctgttct acatattcat tcagcttgcg  21600
tcctgaggcc tcacagcctg gtgggagaca cacaggcact ttagtaatga cccagggggc  21660
aggagagaag cccagggtgg gaggcagagg gagggctttg gaaggggtgg cctttgaggg  21720
actgttgtgt gccaagctct tgactccagg gatgaatgac ctagtccctg tctccaggga  21780
tagctcagaa catggggaaa gctgtggtta ggctgggcat gggcattgtg acctgtagat  21840
tgtaaggagc cataattttt tttttctttt tgagaccgag tcttgctctg tcacccaggc  21900
tggagtgcag tggcgtgatc ttggctcact gcaacctctg cctcccaggt tcaagcaatt  21960
ctcctgtttc agcctcccga gtagctggga ctacaggcac atgctaccac accctgctaa  22020
tttttgtttt tttagtagag acagggtttt accatattgg tcaggctggt ctcgaactgc  22080
tgacctcagg tgattcaccc acctcagcct ctcaaagtgt tgggattata ggcgtgagcc  22140
accgcgccca gcctttaaat ggttttgaca aagtcaggtt tgtgtgtttt ttactgctcc  22200
aggtctcctg tgggaaacag atgctaggaa gtgaagggac tcacccaggg aggtggagct  22260
ggggccagaa ctcagaatcc ctgactcctg gtgggtcccg ttgcctggag tcctcctcag  22320
tgctcccctt gccctggccc tgtccctccc ctgaggtctc ctcatctcct gcctcttcct  22380
cctctctttc caggctccta cttgatggtc aacacttccc agcatgcccc aggccagcga  22440
gcccatgtca tcttccagag cctgagcgag aatgataccc actgtgtgca gttcagctac  22500
ttcctgtaca gccgggacgg gcacagcccg ggcaccctgg gcgtctacgt gcgcgttaat  22560
gggggccccc tgggcagtgc tgtgtggaat atgactggat cccacggccg tcagtggcac  22620
caggctgagc tggctgtcag cactttctgg cccaatgaat atcaggtggg ctgggttcag  22680
tcagcggtca gcctgtgcct ggaggtgggg cagatggatg tcaaattgag gttggagtag  22740
atgagtggct gaagttagaa tgtgtctgca ttcagtatca gaggcaacct gtggtcaagg  22800
ccaggggtca gtctggggcc agtctgggtt cagcatctga ggtcattgtt cctaggaata  22860
gcctctggcc caggtcaagg gtgagttgga acagtgctga cctggaaact ctgtctggct  22920
gcttgagggt aactgtccag gatttgggtg gaaactggcc tccaccttgt tcactatggg  22980
cgctgggacc ccaccccaa ctagctggct tgggagggag ggtcagtgtg agctgggctg  23040
acctctgcta gttgaggcag aggaggctga ggccgagctg aaagtgggca cctccccagg  23100
caaggctgga ggaatatcag tatgataggg gccctcccgc ctcccccagg tgctgtttga  23160
ggccctcatc tccccagacc gcaggggcta catgggccta gatgacatcc tgcttctcag  23220
ctacccctgc ggtgagtccc agcccactgg gggcgcaggg gtaaggggtg tgggcggccg  23280
cggctcctgc ctgcaggggg tgcaggccca gctcacgatg cagctctaac cccgcagcaa  23340
aggccccaca cttctcccgc ctgggcgacg tggaggtcaa cgcgggccag aacgcgtcgt  23400
tccagtgcat ggccgcgggc agagcggccg aggccgaacg cttcctcttg caagtgagcg  23460
ggagcggtga tcttggctgg gggcggggtg ggaggggggtt ggtggctgct tctggccctg  23520
actccccca gattgctgag tccctgcttc atactccagc actgcgcaca gcgtcccggc  23580
```

-continued

```
cctcccctag ctctgctctg cgctttcttg ggtcccccat tcccccaggt tagagcgcgg  23640
ctccaggaac ctatgtccgc gcggtgtagt agggacggct aaatggggcc cgggtcagag  23700
cgagatcggg accccctcgct ccgaggcgcc cctgaccccc tcactctctt ccctgcagcg  23760
gcagagcggg gcgctggtgc cggcggcggg cgtgcggcac atcagccacc ggcgcttcct  23820
ggccactttc ccgctggctg ccgtgagccg cgccgagcag gacctgtacc gctgtgtgtc  23880
ccaggccccg cgcggcgcgg gcgtctctaa cttcgcggag ctcatcgtca agggtcagct  23940
ggtggacgcc ggggagcgcc gggacctcac cctcgagggg cggggccggc gacgggggcg  24000
ggctctgccc gggggcgtgg ccgtgggggg tggggccggc agggtgtcgc tggggcgcta  24060
tctgaagatg ggcctgtgga aatggcagtg gcccagccgg gatgagatct gatctagggg  24120
tcggggctgg cttcgagggg gacggacagg gtcaaggtga gagcctaaag aggggtgggg  24180
ttctggctgt gtgacttctg tgttgatcct agctggcctg cggtccgctc caggaggcga  24240
ggatgtgggg gattaggagg ggcctgagag aggggttgtg ggctgatggg cgagggcggg  24300
gtcagccttt ggagccaggt gccccttagg gcccgggatt tagtgggggt aggagagcgg  24360
gtctggttga gggcttggta gcagcgtgag aggccctagg aggacggaga gggatttggg  24420
tgtggtggaa ctcagagttg ggtgctgggg tctcacagca gcatcggtcc gcctcgcctc  24480
tcccccatct cctcgcagag cccccaactc ccatcgcgcc cccacagctg ctgcgtgctg  24540
gccccaccta cctcatcatc cagctcaaca ccaactccat cattggcgac gggccgatcg  24600
tgcgcaagga gattgagtac cgcatggcgc gcgggccctg ggctgaggtg cacgccgtca  24660
gcctgcagac ctacaagctg tggcacctcg accccgacac agagtatgag atcagcgtgc  24720
tgctcacgcg tcccggagac ggcggcactg gccgccctgg gccacccctc atcagccgca  24780
ccaaatgcgc aggtgggtgc agcagctacc cctggcctca gtctctggtg ggcccagggc  24840
tatggagggg cgcattcgag aggtagcgtg gcctgtgctt gtaaaccttt ctaaaacatt  24900
gtgatttttc ctcaaccctt gttatggtaa agataatgat agctaatact ttactttgtg  24960
tcaggcactt aaacatatct gtgtgtagac acacacacaa acccatattt atagatttaa  25020
aacttacaac actaccacga tgtaggtgct cttgtcgtac ccattttaga tgtgactgag  25080
gtacagagat gttaagtgac tggcccaaga gcacacagct agtaagtggc agagatggga  25140
ttggaactct tgactggctg actccagaat ctgtgttctt aattctacat ctagataaaa  25200
taagcaacta aataccatca aatacaagta tattatacat tctagctggt ttctcttgtc  25260
tgggtgttga gcctgaggtc tgctcttcct tgttaaaaag ggcaaagcag ctgttggagg  25320
atggtacacc tgtgccagat gagggtcttt tttgtttaat cagaagagaa attgagaaca  25380
caataggttt ttctttttgt gactttagta ttgttgttgt tattattttt cctttgaga  25440
cagagttttg ctctgtcacc caggctggag cacagtggcg cgatcttggt tcactgcaac  25500
ctccgcctcc tgggttcaag tgattcttct cctgcctcag cctcccgagt agctgggatt  25560
acaggcatgc tccaccatgc ctggctaatt tttgtatttt tactggagac agagtttcac  25620
caggttggcc aggctggtca caaactcctg acctcaggtg atccacccgc ctcggccttc  25680
caaagtgcta agattatagg cgtgagccac cgtgcctggc ttagtgtgtt tttttaatgg  25740
acttactaag ataaatgtag agtcacatgc agttgtaaaa aaaatacaga aagattctct  25800
gtgcaagtca ccctattttc tgcagtggta acatgttgca aaactatagc ataatatcac  25860
agtcaagata ttcacattga tacaaaccac agatcttatt cagacttttc tggttttgct  25920
tgtacttgtt tgtgtgtgtg tatatgtgta tgtagttctg cacaatttat cacatgtgta  25980
```

-continued

```
ggtttgtgta ttcaccacta cagtcaaaat actgaatagt tcaatcccct taaggactct  26040
tttataacca cattcacctc cctttcttcc tctactcccc aacttttggt agtcactgat  26100
ctgtcctttc taaaatttg ttgtttcaaa aatattatat gaatgaaatc agagtatata  26160
acctctagaa ttggcttttt ttggataaca gctttattgc aatataatcc acatctcata  26220
caattcaatc cttaaaatgt acagttcagt ggtttttagt atacggtagt ccccgtgtat  26280
ctgaagtttc tccttctatg gttttagtta cctgtggtca acttgaggct tgaaaaggtg  26340
agtacaatac aataagatat tttgagagag agagacagac cacatttgta taacttttat  26400
tatagtgtgg tgttgtaatt gttctatttt attattagtt attgttgtga gcctcttact  26460
gtgcctaatg tagaaattaa actttatcat aggtgtgtat gtataggaaa aacatagttt  26520
atctagggtt cggaactctc tgtggtttaa ggcatccact aggggtcttg gaatgtgtcc  26580
cctgcagata tggggggact actgtattga cagagttaca caaccattaa ctcaattaat  26640
taattgagtc aaccattaac cattaatcaa ttttggaaca ttttcatcac ctcagaagga  26700
aattttgtac tctttagcag tcatccccat ttcactcgca cacctctagc cctaggcaac  26760
cactaatttc ctttctgtcc ctatggattt gcctctctgt ggacatttca cataaatgga  26820
atcatataat atataatctt ttgtgactgg cttcttccat ttatttttatt atttatttat  26880
ttatttatta ttaagacgga gtttcactct gtcgccaggc tggagtgcag tggcgtgatc  26940
tcggctcact gcaacctcca cctcctggga tcaagggatt ctcctgcctc agcctcctga  27000
gtagctgaga ctacaggcac ccaccaccat gcctggctaa ttttcgtatt tttagtagag  27060
atggggtttg gccatgttgg ccaggctggt ctcgaattcc tgacatgagg tgatccgcct  27120
gccttagcct cccaaagtgc tgggattaca ggcgtgagcc actgcacctg acccttcttc  27180
catttaacat gatgttttca aggtttatcc tcattgtagc atgtatcaat actccattct  27240
tttttattgc ttaataatat tccattatac aaatatatca cattttattt gtcattcatc  27300
agttgatgga aattggggtt gtttacactt ttcagctatt atgaacagta ttgctatatt  27360
tgtgtacagg tttttatatt gatatatgtt ttcatttttc ttatgtacca tatatatcat  27420
aagatatctc tgtgtttatt cattgaggaa ctgctggact gttttccaaa gcagctgtac  27480
cactttaaat ttccactact tgtctatgag ggttctagtt tctctgcatc cttgtcacca  27540
cttgttatta tctgtcttct tataagcact ctagtatata tgaaatggta tctcattgtg  27600
attttgattt gcattaccct gatggctaat gatatatcga gcattttttc atgtgcttat  27660
tgaccatttc tatatcttct ttgtagaaat gtcttcagag tgttaaaaat gaccaatttt  27720
taagttgggt tatttgtctt tttattattg agttgtaaga ttatttatat attctgagta  27780
ggccgggcat ggtggtggct catgcctgta atcccagcac tttgggggc cgaggagggc  27840
agatcatttg aggccaggag tttgagacca gcctagctaa catgatgaaa cccagcctct  27900
accaaaaata caaaaattag ccaggtgtgg tggtgggctg ttgtcccagc tactcaggag  27960
gctgaggcac aagaatcgct tgaacccggg aggtggaggt tgcagtgagc tgagatggtg  28020
ccactgcact ccagcctggg tgacagactg agattctgtc tcaaaaaaaa aaaaggagta  28080
tttatatatt ctggacacta gatgcttatc agatgtttat gtttgcaaat actttctccc  28140
attctgtgga ttatatttc tttttcttga tagttttttt ttgaagcacg aaagttttca  28200
atttatctat ttttttcttt tgttgtttgt gcttttgatg tcatccctaa gaaaccattg  28260
cctaatccac agtcatgaag atttactcct gtgttttttt ctaatagttt tatagtgtca  28320
```

-continued

```
gctattacat tcaggtcttt gatccacttt gagttaattt ttcaaatgtg gtgtgaggta  28380
gggatccaac ctcattcttt tttttttttt tgagacagag tttcaccctt gtcgcccagg  28440
ctggagtgca atggcgcaat ctcggctcac tgcaacctcc gcctcccagg ttcaagcgat  28500
tctcatgcct cagcctcctg agtagctggg attacaggcg cgtgccacca tgcccagcta  28560
atttttatat ttttggtaga gacagggttt caccatgttg gccgggctgg tctcaaactc  28620
ctgatgtcag gtgatccacc tggctcagcc tcccaaagtg ctaggattat aggcatgcgt  28680
ggccaacttc gttcttttgt atgtagatct ttattaccat ttgttgaaaa gtctattctt  28740
attgaattat cttggcactg gaattggttt ctttcattca gcatagtttc cttcatccaa  28800
gttgtgtata tcagtagttt attccttttt attacttttt attacttttt attccatgct  28860
gtggaaatgc cagtttgttt aaacattcac ctgttgaatg acatctgggc tggttccact  28920
ttttcattat tacaagtaaa gcttctgtga gcattcatac agaggttttt gcatgaacat  28980
aacttttcat ttttctggga taaatgctca agagtacaat caatgagtca tatggtgatt  29040
gcatgtttag ttttatcaga aactgccaga gtggctgtgt tgttttatac tctcaccaac  29100
aacgtatgag tgatccagtt ttctgcatcc ttgccagcat ttagtgttgt cactattttt  29160
tattttggac ttcctgagag gtgtgtagtg atatctcatc atggtcttaa tttgcatttc  29220
ttcagtgtct agtgatgtcg aacatctttt cttttcctct tttttttttg agatggaatc  29280
tcactctgtt gcccaggctg gagtgcagca gcatgatctc agctcactgc aacctccacc  29340
tcccaggtac aagcaattct tgtgcctcag cctcccgagt agctgggatt acaggcacac  29400
accaccacgc ctggctaatt tttgtatttt taggacagat ggggtttcag catgttggcc  29460
aggctggtct tgaactcctg acctcaagtg ttctgcccgc ctcagcctcc caaaatgctg  29520
ggattacaaa catgagccac ggcacctgga caaacatctt ttcatgtgct gtttgccatc  29580
tgtatatcct ctttggtgca tcatctgttc atgtctttga acattttcta attggattat  29640
tctttttgtt gttgttgttg ttgttaagta ttgagagttt tttgtacatt ctaggtacca  29700
gtcctttgtt aaatgtggag tttgtaaata tttcctccca gtagcttgtc ctttcaccct  29760
ctttatatgg actttcacag aactattttc aattttgatg aggttcaatt tgtaaaattt  29820
cccttttatg aattgtggtt ttggtatcaa gtctaagaac tccttgccta tccctgtctc  29880
ccaaagattt tctcctgggt tttttttttt tttttttttt tttttgata cggagtttca  29940
ctcttgttgc ccaggctgga gtgcaatggc atgatctcag cttaccacaa tctctgcctc  30000
ctgggctcaa gtgattctcc tgcttcagcc tcctgagtag ctgggattac aggcatatac  30060
caccatgcct ggctaatttt gtatttttag tagaggtggt tggtcaggct ggtcttgaac  30120
tcctgacctt aggtgatccg gcctcccaaa gtgctgggat tacaggcatg agccaccgcg  30180
cctggcctcc tgtttttttt ctaaaagtgt tatagtttta cattttacat ttaagtttat  30240
gatctatttt gggtaaagtg tgaggtttag gtcaatgtta tttgttgcta atcaatattc  30300
gtaagtgttt taaaaagcca atctgtgaat tatctaaaat ccagtttaaa gccacacttt  30360
gggaactcct tggatggtag gtctaaaatc tggtttaatg tcacactttg ggagaccctt  30420
gagtggtggg tcagaatgtt ccagtgggaa ttgctttcta gtgaaggggt ctgggtcagg  30480
ttacttaacc tttctgagct tcagtccccc tgttttacaa catgggaata ataacattta  30540
ccatataggg ttagtttgaa gatttattca acgaatgctt attgagtgtc tattacgtgc  30600
gaggtgctat tgtggttggt agggatatat gactataacc aggacagaca aaggccacca  30660
acatgtgagt tcttcctgga actcacattt tggcaagagg agatagataa tagatgagta  30720
```

-continued

```
aacaagtgaa gtatacagtt ggcctttgaa catcacaggt ttgaattggg cagatccact  30780
tacatagatt ttttttcac tcacacgtgc atcaaaaata cggtatttgc gggctgggca  30840
tggtgggtta taccttttat cccagtgctt tgggaggctg agatgggagg aatgcttgag  30900
gcaaggagtt tgagaccagc ctggacaaca tagcaaaacc ctgtctctac aacacaacag  30960
caacaataat tagctgaatg tggtggcatg tgcctgtagt cacagctatt caggaggctg  31020
aggcaggagg attgctggag cccaggagat caaggctgca gtgagctaag atttcacact  31080
gcactccagc ctggatgaca gatcaagatc ttatctagag acaaacaaac cagcaataca  31140
aaaaactcca gtgtttctag ggcctgtata tatgaagggc caactatggg acttgaatat  31200
gtgtgaattc ggttatatgt aggggtccta gaaccaatcc ctggcatata ccgagggagg  31260
actttatggc ctgtcagatg gtgataagtg ccgtgaagaa gaaaagcagg gagtggggcc  31320
tggagggttg ttatttttaa aagtctcaag ggaaggtgac atttgagcag agatctgaag  31380
gaggtgaggg actgagccgt gcagagagct gggggcttgc tgggggaagc aagcaccagc  31440
ccgactgagc agccagcaca aaggcctgga ggctggagaa tgcttggcac gtgcaagggg  31500
catccaggag accagtgtca ctgtgttagt gactgagtgg gagatggcag gagaagaggc  31560
tgaagttgag ctgcagatgt gggacttaga gccgttgtac acagagagag ctggggagcc  31620
actgaagagt ttagagagca ggagtgagca tcatctactt ttgtttaaaa ggatcactct  31680
ggccctttttg tggagaatgt tctccaggag ggcaaaggtg ccgcagagac cagggaggag  31740
gctactgcaa tgatctgctt aagaggtggt gatggctggg agccgagtgg aagtggtggt  31800
ggtggggaga agtggtcaga ttctgggttt attttaaagg cagagctaac tgcatttgct  31860
gatggattga atatgggatg agagaaaggg aaatagaagt caaggatggc tccaaggtgt  31920
tttgctagag cagcaggaat gatggagctg tcatttcctg gagcggactg tggtggcagc  31980
tgatttgacg tgggtgtcat agatcaggag ttctgtgttg gaaatgttga cttcgagatc  32040
cctattagac attcaagtgg agatattcat cagcagatgg atacatgagt gtggagttca  32100
gggaaggggt tcgggctgca gatagaaatt tgaaagtcat cagtgtggag atggtataga  32160
tggcatttaa agccctgagg ttggatgaga tcttttacgc taatggttct caactagggg  32220
caattttgtc tcctaggaga catttgacag tgactgagga cataaccgtt gtcacaactg  32280
ggtggcggca atggggtgtt actggcatct aaagggatag aggccaggga agctgctaaa  32340
catcctacaa tgcacagaca gccacataag aaagaattat ctagtctaaa atgttcatag  32400
tgctgaggtt gagaatcccc gattcagtcc ttagattttt agggaataaa tgtagatgga  32460
agaaagagga gttggaaagc ctgaaccttg gagcctccag tgttttgggt taaatgcaga  32520
caattgcagg gaaatgcatt aaatgcatgt gaagtatagc gcttaacaca cagtaagcac  32580
ccagtaaatg atggtgtttt taatctttca aaggcagttc tggtttgcca cttaggataa  32640
aaggaatcat agcacagggt tccgcagagg atctctattg cactcccctt agtgtacaga  32700
tggggaagct gaaacccaga gaggggaaga gacttggctg tgatcagaca gtgggtcaag  32760
aacccaggtt tcatgatgac ggctgttgat tattcccatt ttacagatga ataaactcag  32820
atttagagat ttagccactt gtacaaatct acacagtgag tccatggcag agcttgaatc  32880
aaaatttgaa tctcttgatt tctcatccag tgttttgttt tagttttttg ttttattttg  32940
tttttagaga cagggtctca ctctgtcacc tgggctggag tgcagtggca cgatcatagc  33000
tcactgcgtg cagccttgaa ctcctgggct caagtgatcc tcttgcttca gcctcctaag  33060
```

-continued

```
cagctggggc tacaggcttg caccaccatg cccagctaat ttatatacat atatatatat 33120
atatatatat atatattttt tttttttttt tttttttttt ttttgtagag acagggtttc 33180
actctgttgc tcaggctgat cttaaactcc tggcttcaag ggatcctcct gtttcagcct 33240
cccaaagtgc tgggattaca gacaggagcc agtgcatcca gcctaatcca gtgtttttaa 33300
cagcagcagc agcagctgct gctgccacca tcatgggctg aatgcccact ttgtgctggg 33360
cactgtgaaa cagttttcat aggctggcca ggacggaagc tggggcaggg gcctggcaga 33420
cagggtgcaa acacctcccc ctgcccttct gaattacacg gttctctttg ttgacatcat 33480
ggcccctccc tgcttaggcg cgttggccgg cagttgtttt gctgttggcc agctgtgttg 33540
tcatctcctc catccccatg aaactcccct cgcactatat tatttactgt aaaaacaata 33600
atatagcatc aggcgaaggc attttttaaa ataagcactc cgaagctcat catcctagcc 33660
caacagctgt tttaattttt ctgacttctt cacatctctg cccatatgcc tgcagtagac 33720
atttttacac ccttgcattg ggatgtagaa agcatttcgt atgctgcttc atttgcttgg 33780
tgttgttacg tgtgttatgt tgtttataat tatgtttact gactctagaa gtccattgaa 33840
tgtccccatt tagctggact gtttgcctcc agacttctat aatgataaat aatactatat 33900
tgagaaacct agcgcttgta gttcttccct tctcccccca ccctgagtta tttctttagg 33960
ataaagtgtc aggagtggtt gaagaaaggg cttttaaata tattgcttta aaaaatggtt 34020
gtgccaattt atactgctac tggcatctca tgttaatgca cacatgttta ttaattacta 34080
tagactggta atgactgtag gctggtaatg actgtaggct gggcaatttg actcatatta 34140
tctcatgtaa ctctcacatt tgctctttaa agtaggcatc ataatctcca tttgtttgtt 34200
tttgtttctt tttttgacag agcctcactc tgtcacccag gctggagtgc agtggcatga 34260
tcttggctca ccgcttcctc tacctcccgg gctgaagcta ttcacccacc tcagcctccc 34320
aagtagctgg gactacaggc gcgcaccacc atgcctggct aatttttata tttttgtaga 34380
gatgaggtct cactactatg ttgcccatga aggtctcgaa cccctgagcg atcctgcctt 34440
ggcttcccaa aatgctgaga ttacaggcat gagctactgc acccagccat aatctccatt 34500
ttttagtgga ggaacctgac atcaacattc aaaggggggtt aagtaacttg cctgaagcca 34560
cagaactatg gccaggtgca gtggctcatg cctgtaatcc cagaactttg ggaggctgag 34620
gcaggtggat cacttcagct caggagattg agaccagact ggggcaacat ggtgaaaccc 34680
tgtctctaca aaaaacacaa aacaaattaa ccaggtgcat ggtggcacat gcctgtggtc 34740
ccagctactc aggaaggtga ggtgggagga ttgagactgc agtgagccaa tgatagcacc 34800
actgcactcc agcctgggtg acagtgagac tgtgtctcaa aaaaacaaac acaaacaaac 34860
aaagaaaaaa aagaactaat gagaggtgga gataggatgt gaacttgggt gtaccagatc 34920
ccagtccaaa gctcctccca tgagaaaaag ttgaacattt cagggttatt gcatcttgtt 34980
tagccttact aaagtcaaca catggtggcc taattcaaca gctgttaaat gttatcctca 35040
ttgttttaat gtgcattttg acctctgatc tcggagtgac ctgtagccct gtgtaattta 35100
gagggatggg gctttgaggt ccccaagttc tgttttgtca gcgtgtgttg acagttgaag 35160
agagtgtgtc tgggtgccag atggtttta gaaacgtgga gaaactcatg gattcacacc 35220
cctcaatcaa catatcagtc tgtagtcaac aaactatttg agctccctgg atctgtccag 35280
atatgatcag ggtaggcagg aagaaaaaag aaaagtggac cttcttttca aagagctctc 35340
agtctacctg ggtggatggg aggtggcaca gttgtcaaag aatgagatgc ctaagtctga 35400
agttgggagt ttcatcctcc aaagttgcta tcttgggccc tgtaaggtga tttgaagaag 35460
```

-continued

```
cttgagtagg ttgccagtat ttaaaaatct ggagatttca cataaaaatt ggaatttctg  35520
gctcctcttg aaaaatggga ggatctggca actctgaacc tgtagtcctg cctggcaaca  35580
gtcatctaga ggtgagcagt agctgcccct tttggatggg acactactgt cctgtttgcc  35640
gtggtcttta cccagcatac gtcccccgtt tacatggaac ttctcctgcc cttctgtaaa  35700
tgctgcagga ggactaggaa gcagaatgct tctgccaagc cctagaggct ggaaaggaat  35760
gcagggcagc attccagggg gtggggatgg tgtgagctga gctgcaggga acagagagcc  35820
actcccagta gtgcaaataa agcagtggta cctcggctct tgtagactcc caggacagtg  35880
cacacagggc agccacctcg gctcttgtag actcccagga cagtgcacac agggcagcca  35940
ggaccacagc cagagagttg aagaataacg cgaggacctc tgggaaagat ggcaagtgag  36000
cacaccccag atctgcctcc tctggcgcaa acatagaaga atgatggctt aaaacaaaac  36060
tacattaaaa aaattagaaa aatctctatg ggccaggaat gggagagaaa acctaagtgt  36120
ggtgaatggg cttgcagccc acagtaccca ggatacaggg agcagtggca gccagcccct  36180
cagtgtccat atgggatggg atttgggtgg tccctgcttg tggggagaag ggagccagtc  36240
aggaggcagg ctttgttcct agtgagtgct gaaatctctc ttcgatggct ccatgtataa  36300
ctggagacat gctgcttgcc tgcattccag ggaagaaagg aaaccttctg ggtggaaaca  36360
gaatcttgta ttgtgctgta catggggcca gtgttgaaaa ctgtgttact ggtgcactcc  36420
caagatagga gcagcctggg cgaatgcttt cctttgcatc ttcttcataa ggggaattct  36480
gaacaaatta atcacataaa aaatgccact aggggctggg tgcggtggct caagcctgta  36540
atcccagtac tttgggaggt agaggcagga ggatcagttg agcccaggag tttgagatga  36600
gcctgggcaa cacagcaaga ccctgtctct acaaaaaata caaaaattag ctgggcttgg  36660
tggtacgcac ctgtagtgcc agctacttgg gggactgagg caggaggatc acttgagccg  36720
gggagatcaa ggctgcagtg agccgagatc ctgccactgc actccagctt ggatgacaga  36780
gcaagacctt gtctcaaaaa aaaaaaaaaa aaaaaagaaa aaaaaatgct cctaggggtt  36840
gtacttaatc ttcttaagag attgtatagc ggtgctttct cacctgttca ttaagggatg  36900
ctgaggtccc tctagctggg gacactttgc aggcgatcac agaacttgag agtaatgaaa  36960
ctatacttca tggaatcaga gtgtaagaga gaaaaggatc agttgatgca gtcttggtgt  37020
cttccctcat tttactgatc cagaaattga ggcccagaga tttgcccaag atcacacagc  37080
tggtcaatgc agatgcagga ctaagggctg agtcctgggc tccatcttgc ctttgcttca  37140
gaagccttga cttttctttt ctattctttt ttttcgagac agcgtctcac tgtgtcgccc  37200
aggctggagt gcagtggtgc gatcatggct cactgcagcc tcaacctccc aggtttaagc  37260
aatactcctg cttcagctcc ctgagtagct gggaccacag gcatgtgcca ccatgcccgg  37320
cttatttttg cgcttttagt agagatgggt cttctccatg ttggccaggc tggtctcaaa  37380
ctcctgacct caggtgatcc acctgccttg gctttccaaa gtgctgggat tacaggtgtg  37440
agccaccacg cctggccaac tttttatttt ttgtagagat tgtgtcttgt tgtgttgccc  37500
aggctggtct caaactcctg ggctccagcg attctcctgc ctgggcctcc caaagtgttg  37560
ggattacagg catgagccac tgtgcccagc ccagtttctt tatttataag atggggatag  37620
cattctggtc catagagtca tcaagaaacc gtaaaacata acatgcacct cccttctgct  37680
ggggtagctc gctctctcct gaggcatcag tgaattccta ttggggaggt ggggagtggt  37740
ggttaagagc atggatttcg gagccagcct gaccaggttt ggatcccagc ttcaccactt  37800
```

-continued

```
accatctctg tgactgtggg caagttactg aatttctctg tgccattgtt ttcatatctg  37860
tatgataggg ctaataatag cacttgtctc actagattac aaggattaaa tgagataaag  37920
catttttgt ttttttggg acggagtctc gctctgttgc ccaggctaga gtgcagtggc  37980
acaatctcag cttaccgcaa cctctgcctc ccaggttcaa gagactcctc tgcctcagcc  38040
tcccaagcag ctgggaccac aggcttgcgc caccacgcct ggctaatttt tttgtatttt  38100
tcttttttta atagagacgg ggcttcacca tattggccag gctgggcttg aactcctgac  38160
cttgtgatcc gcctgcctcg gcctcccaaa gtgctgggat tataggcatg agccaccacg  38220
cctggtcgag ataaagcatt ttaaagactc gagaacaatg cccagcctat ccaaaacccc  38280
caatacatgt taactgcctt tattatcatt atcattatat aatagattgt gtttcccttt  38340
ttgctttgac agccagggaa cccaccactg aatttgaacc ttatctttag acctccacat  38400
aggacctaat gtcatgtatt tctgtttctg tttccctgtc attctctggc tttatttaac  38460
tatttggctc tcatttccct cattaccctg atttctgtat gttattatat tatatgtatt  38520
actatacatt gtttcagaac aagtttggaa ttaatacctt aagaaaaata tatcaacagt  38580
ttgattcaga ctggcctgtt gtagtccagg gtgatcttga attaggaggt gaactgtgct  38640
attaaaaata aattattggc cgggtgcggt ggctcacacc tgtaacccaa gcactttggg  38700
aggctgaggt gggtggatca cttgaggtca ggagttcaag accagcctgg ccaacatgtg  38760
aaacgctatc tctaccaaaa atacaaaaat tagccaggcg tggtggtgta cgcctgtaat  38820
cccagctact tgggagtctg aggtggaagg attgcttgaa cctgggaggc agaggttgca  38880
gtgagcctag atcatgccat tgcactccct cctgggtgac agagtgagcc tctgtcaaaa  38940
aaaaaaaaaa aaaagctaat atttttgagg gcttattgta tattagccat tgtcatgcat  39000
cctttgtgtg tatttcctta aaccttacaa tgatcctatg aggcagggcc tattatcttt  39060
tcattttgca gttgaggaat ctaaggatca gaggggtgaa gtgattcagc cagcagttgc  39120
cagctgcaag tggcagagcc aggattcaaa tgtagtccgc ctgactccaa agcacatact  39180
tttactccct gtttgatgtt ctaggggtcc cctgagctct tgggggcaat ggagggatga  39240
tttcaggcag ctgactgatg ctttctctcc ctgttcttct tcctcttctc ttcccatttc  39300
ttctaacttc ttctctctgc ttcctgcatt ctccagagcc catgagggcc cccaaaggcc  39360
tggcttttgc tgagatccag gcccgtcagc tgaccctgca gtgggaacca ctgggctaca  39420
acgtgacgcg ttgccacacc tatactgtgt cgctgtgcta tcactacacc ctgggcagca  39480
gccacaacca gaccatccga gagtgtgtga agacagagca aggtgtcagc cgctacacca  39540
tcaagaacct gctgccctat cggaacgttc acgtgaggct tgtcctcact aaccctgagg  39600
ggcgcaaaga gggcaaggag gtcactttcc agacggatga ggatggtaag agtctcagtc  39660
ccaattcccg gggccctgtg tacctcccac agatacgcca tgtctgagac tgaaatttac  39720
tgagggtatt tttttctttt ttttgcttag gattaaacca actgtataac accaaagtag  39780
tgatagctcc tattttttct ctggaagact ttgggttaga ttggtctaat ttctttcctt  39840
aagtgtttga aagaattcag cagtgaagcc atttgggcat agagttttct ttgtggcaag  39900
gtttttagta aattttagtt tttaaaatag atattgggat attcagattt ttttattctt  39960
gtatcagttt agatggactg tattttttaa ggaatttgtt cattacacct aaattgtcaa  40020
atttcttgag ataatgttgt tttataatttt ttttatttat ttagagacag agtcttgctc  40080
tgttgcccag gctggagtac agtggcacca tctcagtttg ctgcagcctc ctcctcccag  40140
gctcaagcga tcctcccacc tcagcctcct gagctgggac tacaggcatg caccaccacg  40200
```

-continued

```
ccaagctagt ttatttattt ttgaggcagg gactcacact tttgtccagg tgggagtgca  40260
gtgtcatgat tatggctcac tgcagcctcg acctcccagg ctcaaatgat cactctacct  40320
cagcctccca agtagctggg actatagacg tgcactgcca tgcctggcta atttttttgt  40380
atttttgta gagacggggt tttgccatgt tgcccaggct ggtctcgaac tcctgggctc  40440
aagtgatcca cccaccttgg cctccaaaag tgctgggatt acaggcatga gccacttcat  40500
ttgccaatat tcttttatta tatttattta atgtccatag gctctatagt gatatcatct  40560
ttttcatttc tgatattggt aatttctgtt ttcttttttc ttgtttaccc ttgtgaagac  40620
tgtataaatt aatctttcca aagaaccaac tgttggctta cttgattttc tttattttct  40680
atttttattt tcctttgtta tactttcttt ggagttgatt tgctgttctg tttgcctttt  40740
gagatagaag tttcttagat cattaatact gagcccttct tcatttctaa tatacgtgtt  40800
taaagctaca cattttcctc taagtcctgc tttagctgtg tcccacaagt tttgatattt  40860
cctatcttca ttatcattca gttcaatttg ttgtctatac aattgaactg ttatttctgt  40920
tataatttct gctttgacct aagagttact tagaattatg ttgcttaatt tctaagcaat  40980
tgggactttt ctttttttgtt tgtttttgag acacagtttc actctgtcac ccaggctgga  41040
gtgcagtggc acaatctcgg ctcactgcaa actccgcctt ctgggttcaa gtgattctca  41100
tgcctcagcc tcctgagtag ctgggatttc aggtgcccgc caccacgcct ggctaatttt  41160
tgtattttta gtagagacag ggtttcatca tgttggccag gctggtctcg aactcctgac  41220
ctcaggtgat ctgcccacct tggccctgca aagtgcggag attataggca tgagccactg  41280
cacctggcca gcaattggga cttttctaat tgtcttttta ttattgattt ctaggttaat  41340
tccactgtag tcagagtata tactctaaat tttattttgt gaaatttcat ctttacttta  41400
tggcccaaca tattgttaaa ttttggtaaa tgttccagtg tatttgaaaa gaacatgtat  41460
tctgttgctg ttgaatgcag tgttctacat atgtcaaact aatatttagc ccttagcaca  41520
ttcaagcacc attctgaatg gttttgatat attactgcat ttaataccca tgacaaccct  41580
atgtggtagg ttactatttc tattcccatt ttatttctat tcccatttta cagaagaagt  41640
cacagaaagc ctggctttct aacctgacca tctggcttca cagttgtcat tctttttttt  41700
ttttttttt ttttttttt tttttgagat ggagtcttgt tctgttgccc aggctggaga  41760
gcagtggtgc aatctcaact cactgcaacc tctgccttcc tggttccagc gattctccca  41820
cctcagcctg tcgagtaact gggattatag gcacctacca ctacgccggc taatttttttg  41880
tatttttggt agagatgggg gtttcaccat gttggccagg ctggtctcga actcctgacc  41940
tcaagtgatc cgcctgcctc ggcctcccaa aggtgctggg attacatgcg tgagccaccg  42000
tgcccagcca gttgtccttc ttaagagcta cactcgaatg ctatcacagg tccaaagcct  42060
ttccctgggt tcctacagat tccagttacc actaagctcc ttggtttatg gctttgtctt  42120
gctgccgcac gtgcacagtt ttctgttctg cacagcattg gcctagattc aaaattcagc  42180
tccttcttta ctttctgctt ttctctgcct taggacttca gcttccccat agtggtttat  42240
caaggtattt tcccaagcaa agatcattct cttcctaaat gacactcctg tgcctgccat  42300
taacagtata catttacaca agaaaaacaa aacaaagcca tgcctgcaag tgttaatgct  42360
aaaatgttaa cagtatctct gggtgataca attgtagatg ccattaattt tctttaagct  42420
cattttgatt ttctacattg aacatgtcat ttatgtaatt agaaattttt agacgagaaa  42480
atatcgccac ccataatccc aataccgcaa tgcaattgct gttttcattt ctctggccca  42540
```

-continued

```
tgtgcatatt ttctgaaaac tacccaactg gaacaaaatt ggagccttca aacgtatttc  42600
tctcctgaat gcaacctaca cagtaatgaa aatgccagct atccattttg agtacttagt  42660
aataggttga accatatgca attgctgatg tttgccttgg ggctttatgt acatcacatc  42720
atttgagtcc tggcttgaga ggggttatat cattccact tcacagctga gttaagtaag  42780
gtgcagagag gctgaatagt ccatgagaac caggtaggaa gcggcaaggc tggaatttaa  42840
acccaggtgt ctggcaccaa agcccacttt cccctggccc ctgctgcctt tcccttgcag  42900
tgcccagtgg gattgcagcc gagtccctga ccttcactcc actggaggac atgatcttcc  42960
tcaagtggga ggagccccag gagcccaatg gtctcatcac ccagtatgag gtgggtttgg  43020
gaccctatta cagtgggga ccctggtgga aggtgagagg tggccctctt tctctctgct  43080
gctacagtag gaggtgcatg ggaggacaga tgtgattgtc atagtttctt caactatggc  43140
caggtctgtg ccctgtgtat tctagaggag ggtcctgaag gcaggaggga gagccgaaga  43200
tgactagaag cctggcttga tggcatccat agtctccttt gcttagcctt atctctcact  43260
tccctgggac atggtgggtg gaggctgctg gtcagggatg ctctgaccat ccagtgccca  43320
cctgcctgcc aatcctgccc ccagatcagc taccagagca tcgagtcatc agacccggca  43380
gtgaacgtgc caggcccacg acgtaccatc tccaagctcc gcaatgagac ctaccatgtc  43440
ttctccaacc tgcacccagg caccacctac ctgttctccg tgcgggcccg cacaggcaaa  43500
ggcttcggcc aggcggcact cactgagata accactaaca tctctggtga gccccacctg  43560
acccggccca gcctcttcgg aggtggccca gaatcccagg gttccatggg cagaagggaa  43620
atggggggca tcctgggggt agttacagag ggcccctgct gagataaata tgccatttag  43680
gagttaaagt caggctcagg gaggatgaag tcagaggagt caggagactg gtcagtggaa  43740
tcagaagatt gaggttgggg ctggtgcctg aggtcagggg ccagggtagc tcaggtcatg  43800
tcagcaggaa caaagaggct aaggctgaag taggggagat ctgaggactg tggtcaagga  43860
ggctggaagc ctggtcttcc tggtccagtg gccaagctcc agcttgtgac cctgtcccct  43920
tctccagctc ccagctttga ttatgccgac atgccgtcac ccctgggcga gtctgagaac  43980
accatcaccg tgctgctgag gccggcacag ggccgcggtg cgcccatcag gtgggaaagc  44040
ggggacggag gggtgggagt ccagggcctt aggaaagagg cccctcctct gacccagagc  44100
cccatcccag gccagctcac ccttttcctc cctcagtctc ccacgcaggg cttggagtgt  44160
ctggaggaga ttgttctgtg atgcttggca ggcaagaagc ctgcagtccc tcccctctga  44220
ggccatgggt ctcagatggt gactgtcagg aggaccctgg ataggtccag cctggagagg  44280
ggactgtcca ggcctgtcca gggggccttt cctcagacac cttggagaag tgaaactctg  44340
ggggccttat atcatcccag ccttttcctg gaagcacaga gatgggcttt ctagaaggct  44400
ggggcagcca gccagatagg gccatctctc tggaatggct aggagcttgg cttctccacc  44460
tcctctcccc agaggaagct gggcttgctg gtgccgtggt ggctgcctct gctggggaga  44520
gggtgctgga gacaagactg tgtgtgtgtg tgtgtgtgtg tgtgtgtgta tgtgggatgt  44580
gaaactgggt gtgtctttgt gataaagaca tgggatgtgt ggtgtgagtg tgtgtgagag  44640
gcgtatatgg gagacataag tgtgcatgtg tgtgagagtg tgagggtgtt tgtgcaactg  44700
tgtgcacgta ctgttagcca gaccccgtgc taggggcttt atctgcatga agccatttat  44760
cctcatggca gccctgtggc atgggtatta ttaccttcat tttacatatc gggaaactga  44820
ctcagagcct gaatcacttg ccctcaaggc cacacagcta gtaagtggtg gagctgggat  44880
ttggaagcca ggtctatctg ctgtgcctgt accttttcta gaagttatag agcctccctg  44940
```

```
cccttctggt ccacccccttc cttccacgaa ggtacatgct ctgggagagg gtgacagcct  45000
ttaggtgggg ggggtgtgag ggtcctagtc agttccctag gaagagagtg ggctgcctgg  45060
gtgaccatgg cagtccctca cctcctcact ccccactgta tcctctcctc ttctgctttg  45120
tcttccctgt atttgccact gcaaatcctg ccctgggctg attcccagac cctcagggaa  45180
gacccaggaa aaagtcacgg ggtctgcagg gccttttgcc tgttgctaga gcctcagggc  45240
ccttatgcca ctgagtctgg gatgggttgg gaaccctttc tttcttgtcc tcttgaggga  45300
tcctgtgagc agcactggtc agggtccctc aggatgatga ttgcaaggct aggtgggggc  45360
aggcttggtg ggaggggagc ggcaagatgg ctgcatgacc ctgggcatgt cccgttacct  45420
tcctgagcct ccgtttcttt atctgcacaa tggggattat tctagattaa gatgcacttt  45480
gttcatggct aatgttaatg attacctcct ggtgggattt agggctagga gaggcctgac  45540
cttagcctgg ggcaatggag gctgaaaggg gcttggactg gtgtttataa tgggctagtg  45600
acaagccatg ggctggtgtc caacactctg ggatgattcc ccacaacttg gatgctccaa  45660
agaaacatct ggtgagcaag gaaaaggcat ttctgcttcc ccaaggagag gctgtcagta  45720
tgggatgtca cacgccaaga cgtgaccgag actgtaactg gaaatattta aatttgtcag  45780
gattcactta tttactctcc actttgttct gcagaggatt tggaggagct catagcagaa  45840
acctatttag taaagagata aaatagaaac acagctggga ccagggagca cgaaccagag  45900
tgggcagtca ggatcctgaa acagcagggc tccgatttgc tgatcagagg ctgccttggc  45960
attgggaggg tgctagagac atagtgttgg gtgtccttgt ttgctaaatc actgtctctc  46020
actagaggtc agttttagga agcccagttg cctagtgtat agcacagggc tcatagtctg  46080
agctcagtca tctctttctg aatgaatgaa tgaatgaatg aatgaatctg gctaaccctg  46140
tcatttactg agtcccagaa gggagctttc agtagctttg gtttcccagg tcttgtgtca  46200
cacacacagg aggactcatg gaggaagcag gctggggcct tatggcttgg ttatattgag  46260
cagggtccac gatcctctta gcctggatta gtaacaggaa taaccgctga caggtgctgg  46320
ctgcttgctt aacttgcctg ttcttcccat ctatcttctg aacagtcttg caattactcc  46380
cattttatgg aggaagaaac cgaggcccag ggaggttagg ggacttgccc agctagtaag  46440
gagcagtgtg tggaagttag tccccaggag ggcttgacca caaagcccat gcctttaact  46500
gccagctggc tctcccagtc ctctggccgc ctgtgatccc ctgtacgctc tcctccctgt  46560
ccagtgtgta ccaggtgatt gtggaggagg agcgggcgcg gaggctgcgg cgggagccag  46620
gtggacagga ctgcttccca gtgccattga ccttcgaggc ggcgctggcc cgaggcctgg  46680
tgcactactt cggggccgaa ctggcggcca gcagtctacc tgaggccatg ccctttaccg  46740
tgggtgacaa ccagacctac cgaggcttct ggaacccacc acttgagcct aggaaggcct  46800
atctcatcta cttccaggca gcaagccacc tgaagggggt gagggaccgg ccagggtcat  46860
ggtgggcgtg gttgggtgtg gggggatggc agacaggaga taccttggag caggcccagc  46920
gcagactcca ggcccggcac ttcccatagc cccacctccc atagccccac ctcccatagc  46980
tcctcctcct acagcccacc cccatagccc tacctcctgt agccccacct cccatagccc  47040
tggccccaca gttcctcccc cataaccttg cccctcccat agccctgcct ccttttgccc  47100
acctcccatt gccccacctc caatagcctt acctcccata gagccacccc cacggccccg  47160
cctcccacag ccccacctcc cagagtccgt cccatagtcc cttctcccat agcccctccc  47220
ccatggtccc acccctccca tagccagccc tcctgacccc aggctccttc ccacagagca  47280
```

-continued

```
ctaccccctt cctgagcctt ctttctcagg ctcctccttt ctatccaggt ccccagtcta  47340
gtctctgccc cttcctgagg ccctgccttc tatcttagat gcttctcttc ccagaggagt  47400
ccatctcaga ttccagcgtt cctgtgttaa ggcctaggac ccgcctcctc cctgaagccc  47460
caccttatcc tccaggctcc tccctcctct gcttcttgcc tggtttcttg cctggtttct  47520
gacttcctag ctggacctct ggccctaggc ctcgccccga tgcccgaggc cccgcccatt  47580
tccccaagac gtttgtttct cttttgcctc cgatctcatc cccctttcct aaggcactgc  47640
aggtgcctcc cctctaggcc ccgctctcaa gggtccccc aggcctgcct tcgggtgggg  47700
tgtcccttga tgccatcagc acaagacaaa gccctgaaca ggcccaagaa acgctgtctg  47760
aggttcccac cctggggagg gagaggtcgg ggcttcagca acgctgagac cccatctgt  47820
gcctccagga gacccggctg aattgcatcc gcattgccag gaaaggtaag tccgctgagt  47880
tcctgcagcc tttcagcggc aggtttctca cctgcccagc gctggggagg tggatcctga  47940
ggacctacgg ctgtgggagt agaggagggt ggttgggcag tcctggggcc aggaggggct  48000
tcctgctggg tttccatgtg ccctacctca agggcgcctt ctcccagggt gacagcaggg  48060
gcctggagca ggcttgtgga gaggagccat tatagttggg ccttgggggt gatgggtaca  48120
gggtgctggt tctgggttac gtatctgtcc ggctttcctg tggtggggga gaaggtgagg  48180
tcagcatggg ccctgtgcta taggtatctt tcctgcttcc agacagggaa tgtggttggt  48240
ttcccatcct gagatggact aaccatgccc taggtacaca attcctaatc cctgttacct  48300
cccaggaggg caagagggtg gggctgaagc ccaggtgtct gctctcccct atccactgag  48360
agctgggagg atctgagaaa gtgggaagcg agggaagcta ttcctggcaa aggagccata  48420
tcagtgagga ctgtggcgtg gaagtgcaga aggtatcagg gatggtgagg aggtagattt  48480
gctcaaaagg caggacacac attgaggatg tagggcggtt tgtgcagccc agtttgttcc  48540
ttgggcacag ccacctacag gaggggctcg atggtccctg tctttcctct gatcccttgt  48600
tctgctttgt tctccccagc tgcctgcaag gaaagcaagc ggcccctgga ggtgtcccag  48660
agatcggagg agatggggct tatcctgggc atctgtgcag gggggcttgc tgtcctcatc  48720
cttctcctgg gtgccatcat tgtcatcatc cgcaaagggt gagtgaggcc ggtgccctgt  48780
cccaccagtg gcttctaccc cttagaggcc tggtggcaca gaggaatagt ggctaagagc  48840
tggtagggca gctgtcctgc aggtgtgtgg agggctgcca gcctgggcat cgcctctaca  48900
gatggatctg agctgggtgg tgggaagcca gagactggga agatggggct gccctggagt  48960
ggcatggctg gagtacagtt ctggctggtg ccaggtgctg ccatccaggg aggggtgctc  49020
agtgcctggt gccaaggagc tatgcctgct gggactgttt caatagggag ggcatagagg  49080
tgacctggct ttgaacccct accctcctgc agaccttcag ccaaggtgtc tgccctgctt  49140
atgggattgt gcagttgacc tgagcagagg atggagctca ctcctcttta aaccaagggc  49200
cctgagccat ggctcttccc gggatccacc ttctctcagg ctcaacttgc cctggaccct  49260
gttcctgtgg atccttgagg agccctcctg ggcctgtgac tgataaaccc ctccccctgc  49320
cgcccctact atccctcgtg tctcaaaggt ccagcctgtg tttgcatgaa atgtgtttcc  49380
tagcggattt gcagagggca gcatatatcc caggacattg tggaatccag aacctagaat  49440
cttgcagttt cagaaatgta ggatttagga ctctaggaat cttaggcttt agaattgtag  49500
aggctcagag ccccagaacg taagagctgc caggtagttc aaggccatct agtctagtgg  49560
ttttcaaatc tttttaaaga aacagaacct gccttcaaaa caccagaaaa cccttccctg  49620
ggagcctagt aaaatggagc agatgaaggc tgagcagcag tgctggtcgg aagctgagtg  49680
```

-continued

```
ggggcttctg ggacttttct gtttgccagc tctgccccac catgttcccc accaggcagc  49740
cgtgggacac tgtggtccaa gcgccttaaa tgagggatgg ggatgttgag gcctagaggg  49800
cacgcagggc tgcccaaggc tacccggaga gccagaggca gagccagctc caccccttccc  49860
cacctgggct ctggcttcta tagcccctac tgctgccagg ctgggcatac atggatgagt  49920
tggttgtatc tctgggctgc caggagcgga taataggatc caggaagatg agagagagag  49980
ctggctgggg ccaccttgcc tgaggccaga caccagcaag agagagagag tctaggggtg  50040
gagtgtgcag cggagtggag gagatggggg ggatggccca gccagggcga tacactctga  50100
tttttcccct cgttgttcct gcacagcttt aagagagact attttaaagt atcatttaat  50160
gagggattac tatgtgccag gagcttcaca cacatcatcc atgagtacat tagttattgg  50220
acatctactg tgtaccaggc actgttctgc actcagcatg cgtcagagaa catttccttc  50280
ttggatcttg actgactccc tttttttgg atgaagaaac tgtaatgaaa gcaccttgcc  50340
caggccactt ggctgatgag cagtagggcc tgacttcaac tcaggctcgc ctacaaatgt  50400
gaaggcctca ctgagtctgg tgcataggca gtgcccccag aatggcaagc ccctgacttt  50460
cccccagcag gggcctgag aagtgacttt aagtagggct ggggctggag agggctatag  50520
tggagggggc agatttcagt ttcaggtggt atttgaggtc ctagaaatct accctcaagg  50580
agaagaggat tggcagagtg aggggtgtca aagagagccc tgcaaagaga gcactgggcc  50640
caggacaggc tggatcagaa atgttgtcag ggcctcactg ggaaaccttc cattatgtat  50700
ttgctacccc ataaacccaa gttatcccag atgcctccag gaacccctca tcccccatca  50760
ctctggacct ccttacttcc tctaaaagcc attcagtctc actgtgtagt acccactgca  50820
tgcccctgga tctgagcctg gccttcaggg ccttccgtgc tcctcagggc ttttgcagtc  50880
tgcattgtgg gtatcatggg atgcagcagc cctggcaggg atgggggtgt tcagatcaac  50940
gtggggtgcc aacataacta acaagagtag gaagttgctg aggagggcag ttaccacgcc  51000
cccaggaggg agtcccaggg ggattatggg taatagaggc cagctggaag aagatttcag  51060
attctccatc ctgccctgcc tctgtggacc atcagactgg atgcatctgc tgtaggggaa  51120
ttccagggcc tggaagggag gctggtgacc ccaggccagg tcagatcccc tggctgtgct  51180
tccagaagtc cccatacccc acccttctcc atggcagcac tttcttctcc ctgcactttg  51240
tcatttactt acttgtagtg ttttgctcaa tgcttgcctc ccctcctggg ttaagagctc  51300
catgaagggc agagaaagcc ctgtcttgtc tatatctcca cagtctagcc caggggagtc  51360
gggtctcccc actctgaggt gtagggagga gtggtttgtg ggcactgctg ggtgcttccc  51420
ggtgctgagg cctcacagca gtccctgtgg gagattatta ttaacctcac tgtgtatgta  51480
tgtttttttt tttttttttt ttaaatggac tcaagctctg tcatccaggc tagagtgcgg  51540
tggcgcgatc tcagctcact gcaagctctg cctcccaggt tcacgccatt ctcctgcctc  51600
agccttccaa gtagctggga ctacaggcgc ccaccaccac gcccagctaa tttttttttt  51660
atttttagta gagacggggt ttcaccttgt tagccaggat gggtatgtat gtattttttg  51720
agacagagtt ttgctcttgt tgtccaggct ggagtgcagt gatgcagtct tggctcactg  51780
caacctctgc ctcctgggtt caagtgattc tcctgcctca gcctcctgag tagctgggat  51840
tacaggcgcc caccaccata ctcggctaat tttttgtatt tttagtagag acagggcatc  51900
atcatgttgg ccaggctggt ctcaaactcc cgacctcagg tgatccaccc gcctcggcct  51960
cccaaaatgc aggattata ggcctacctg agccaccatg cccaggctta acctcacttt  52020
```

-continued

```
ttaaagaaga aagtggaagc gcatggaggt gaagttcttt tatttatttt tcctcattta  52080
ttgattactc cattcaacaa aatatttatt gtgggattac aatgtgtggg gccctgggga  52140
aactgaggga gacaaaaaga caaggattct gtcctcctgt actttgtagc cagtggagag  52200
cctggcatga aattagaaaa agcacaaatg gaagagataa ttgcaaattg tgaaaagaac  52260
agggtgctgg gtgttggggg caaagagaat acaagagaca tcatgtagct ggcactcgtg  52320
ggagagtggt ccgggaaggc ccttttgaag gcacaatgtg tcaactgagg ccagaagaat  52380
gccatttctt cagccgtgtc ctccctcgtg ggcctctgc aacagcccca gcgccctaga  52440
ctctcccctc tctccctggg atggaggaga tgtgctctgt gacctggggc caagctcctg  52500
cctttgctgg tccgtcttcc gctctcctcc ccttcatctg caggatttcc tgtggaaggc  52560
cattctttgg ggtccctgct gacagggtga tgtgggggca agtgaatgga ggcctctgga  52620
gagcctggga ggggagcaca gaggaagttc caggaccagg gtcctggggc aggtgtttgc  52680
tctggactct gccactgacc cccagagagg cccaggtagc ccatgctccc tgactcagct  52740
tccccgccta tgaaatggga atccaacctg ctttacactg tgggtgcttt gcggtaaggt  52800
agggctcttg atggaagctg tgccccaggt gctcccagag gggatgacct ggctccttta  52860
gtggatccca cacccagggg caggcagggt aggtaagggt gggccctagt tgtgtcctgg  52920
gcatacatct ggagtcctct ccatcctgcc ccctttctgt ccccacccag gtggaggtgc  52980
aggcaaaggg ctgacccctt atgggcagag ggccgtgcag ggtgggaggg tgggggatga  53040
gaacagccct ggtaagcaca gttagcctag agagtatgag tctgtgtgtg tcaggggatg  53100
tctaatgtgt gtgtgtgtgt gtttgtgaat atatgtctaa gtgagtgtgt gtcaagtgtg  53160
tctgaataca tgtgtatgca tgtctgcacc tgtgtgtctg catttgtggg tgttgatatg  53220
tgtttctcca tgtatgagtg tgtatgtgag catatatcta catgtgtgtc tgtgtgagtg  53280
tgcatatgtg tatgactgtg tgaaagctct gcggcccccct aggtcctttt cccacctcct  53340
cctcactcct gcagtaggct tggggaaggt ttcagaaggg ccttgggtcc tggtcattaa  53400
tatctgagcc tgaccaggga ggtcctcctg acctgttcag tccctggcca gccccctccc  53460
cagcccggga ggtacccagg ccccaccctg ctgcctgggc attgcctcag cccggccttg  53520
gtggacggac ctcggacaca actgtgctgt tctctctttg cacgctgcca ggagagacca  53580
ctatgcctac tcctactacc cgtaagtagc tctaccttgc ctgggagtcc ccggccctgc  53640
ctagggggag atcccctgtc cccgccttct ctggttgggc ttagtctcgc tgcacccagc  53700
ctggcctggt gtccacccgg ttctctctgg tcacctcggc ctctgacttt ctttcctctg  53760
ctctgtcctt cccctctgca tcttcctcct caagtcgtgg tcatgagtgc tggttctgcc  53820
cctaagaggc atgggttcag agctggccct gctgagtcac cccagcaag tccctgagcc  53880
tcaatgtccc cttcaccacc agagcagccc cttacgtcta ctgttcctcg tggttagaag  53940
tatgtcctga cctccaacca aatccacgtt caggacacgc tctggagccc acgtccatgt  54000
gcatgtgtgt gcttgtgtgc atgtgggtgg ggcctacctg ttctgagact ggcagcttct  54060
cccacagcac aggcaactct caggccccta caagtccctt ctccagccag gcagccccag  54120
ctctgcagac ccaccatttc ctgggagcct cctctgggcc aagccctgtg ctcagttctt  54180
gacagagtcc tcacaacagc tctgagaaat aggagctttt atcactccca ctttactgat  54240
gaggaaactg aggctcagag agaccaaggg agttgtggga ggttgcaaaa tgcactggaa  54300
ctgggataca acccaggccc ctgctgactc cacagcctgc cgatgctact ctgtcttctc  54360
tctctgtctt ctactctgca agccttctgg aacattcctc ctgcccctgt gctggttttc  54420
```

```
cctccctcga agtgcaggcc cagagggcgc caggccagcc ctgaggacag tgggtctctc  54480
acctcctcct ccctggacag ctccttacct tagtgtttcc tgacacgagc ttttccaaca  54540
actcaacacc cagcgactcg cgctgagccc ccagctcggc tcctgcaggg gctgtggaca  54600
ggcagctctc cctgctgctt gcgcagttag ttttcaaaac cagatgcaga acttctcaaa  54660
gaatctgtat taaattccat ctgcttaatc tcacattgag ctcagctgga tgccaacagc  54720
attaggtgtc cctcccgggt tccatcttct ggggatcggg ttggtttgtt tctgtagctc  54780
ttcttccagg taggccagga atcctgggct gggaacagag cctgtggcac acccctggag  54840
accaccctct aggccagcat ctgctcagtg acgggtcctc tctgggctcc atgttcagcc  54900
aggctggctg gctgtcctct gtccatggcc ctatctcccc acctcctttt ctccctccca  54960
ctttcctcca agttccttcg aagtcacaaa ctgccatcct catccgtgaa gctgggcctg  55020
gagggagagg aggtctctct ttctcttccc tgctgctctg agcagcagga cggactggtg  55080
ggcagtggtg ggaatctgga ccttctgtgg gtctctttac aagtctgtgg tggtctatgc  55140
tgggaccatc ctaggtgcta ctgggagtag ggagaagcca agggtggagt tcattctgtg  55200
cgtgggggaa gcccccgagc tctggctgag cacaagctag actctctgcg gggaaggagg  55260
ggtgtagtcc ctccttcctg caggagaagg aggagtctgg agagtggtcc ctgtttaaca  55320
cggggaggag agaggtgggg acatgctggg cctggagctg ggccagccat tttcctagtt  55380
tggggtgcag tgggggtgag ggggctgtct gctgtgacac caaattagcc ctggagtgac  55440
tttctttccc atttcctaag cccagggggc cagtgaaact taggagtgag atcccagcct  55500
gaagccactg ctgctccacc cctttccctt agcaaaggtc cctaggacgg gctctgccaa  55560
gcccttttca gggaagaagc agctctgggt ctaatgagtg aaggatgggg gcagagccct  55620
cagcatccag agatgcttct aggacagctg ctggctcctg gccttgaggt ccccttactc  55680
cagggcctcc ccagccacct ctgggtgctg tccagcccca cacaatgcct gtgtctcccc  55740
tcaacccccc tctccaggaa gccggtgaac atgaccaagg ccaccgtcaa ctaccgccag  55800
gagaagacac acatgatgag cgccgtggac cgcagcttca cagaccagag caccctgcag  55860
gaggacgagc ggctgggcct gtccttcatg gacacccatg gctacagcac ccggggtgag  55920
tgcccggccc tcctacccct tcttcatggc tctggggctc ccaacctgag acaatagggt  55980
ccccacatca ggtgagttct gtaacacctg caaccaaaag tgaagcatct gtggtgctcc  56040
tgctggatac cttctggata tagagccagc acaggtggcg tttttgcatt gtgtactaga  56100
ggagcttgca aggaattctg ctagcaaaag aggaatgcaa ggtccattgt gacagtcgtc  56160
aaggaggagg tgctgctgta ggatcagagg gatcagagtg gcctcacccc ttattgagca  56220
cctgttatgt gagaggtggg gatacagtgg ctgagagaga ccgatataga gtcagacctg  56280
ggcttacctc tccctttctt agctgtgtga cctggggcaa gtcacttaag ccctctggat  56340
gtctgtttcc ttgtgtataa aatgggaatg cagattgcct ctgctagtag ggccgatgtg  56400
aagactaaat gagataatgt gtgcaaaatc acttagggct gtgcttgtat tcacagaata  56460
tagtgagtca gccgttatgt actaggtctg tgtcataact tgcttcatcc cacatctttt  56520
tattctgttt agtgttgatt tgtacagaag agaatatgta atgtttatga aagtcataaa  56580
atcataacaa tacaacaaac agcaatgaac ctcattggtg aattagaaca ttatcttggt  56640
acacctccct ggctatatcc cctacctctt tcttagatgt aaatattccc ttgaaattgt  56700
tgtgtttttt tttttttttt gtgagatgga gtctcactct atcacccagg ctggagtgca  56760
```

-continued

```
gtggcatgat ctcggctcac tgtaacctct gcctcccagg ttcaaacaat tttcctgcct  56820
taacctccca agtagctggg attacaggca cctgccacca tacccggcta attttttgt  56880
tttttgaga tggagtctca ctctgttgcc caggctggag tgcagtggtg tgatcttggc  56940
tcactgtaac ctctgcctcc agggttggag caattctcct ggctcagcct cctgagtagc  57000
tgggattaca ggtgtgcgcc accacaccca gataattttt gtatttttag tagatggggt  57060
ttcaccatgt tggccaggct ggtcttgaac tcctgacctt aggtgatcca cccaccttgg  57120
cctcccagag tcttgggatt acaggcgtga gccaccgcac ctggccagtt tttgtatttt  57180
tagtagagac agggtttcac catgttagcc acgctgttag ccacgctggt ctcgaactcc  57240
tgacctcaat tgatctgtcc gcctcagcct cccaaagtgt tgggattact ggcgtgagtc  57300
actgtgccca gcctcccttg aaatttgtgt ttataatttt cctacctttt tcgggggtag  57360
tttttgttt ttttttttt tgagacggag tctccctctg tcacccaggc tggagtgcag  57420
tggcgcaatc tccgctcact gcaagctccg cctcccgcat tcatgccatt cttctgcctc  57480
agtctcccta gtagctggga ctacaggcgc ccgccactgc gcccggctaa tttttgtat  57540
ttttaataga gacgggattt caccgtgtta gccaggatgg tctcgatctc ctgacctcgt  57600
gatccacctg cctcgacctc ccaaagtgct gggattacag gcgtgagcca ctgcgcccgg  57660
acttttgggg gtagttttac catgtgtaca tatatcccca aacaacgcat tgtatagttt  57720
tgctcatttt catcctttat aaaaatgaaa tcacacacta cttaactcca catcatattt  57780
aaatttaccc atgtggatgt tttgctgcag ttcatttact ttctctgatg cgtagtttcc  57840
cattgtatgg ctgtatcaca attgacttct ccattctgcc atccatgggc attcgattgg  57900
tttttagttt tcttgttatc acaaatgaga ctgctgtgaa tattctgatg tggatgtcta  57960
gatgcacctg cacacaaggt tctagaaata gaattgctgg attatggagt acgtgcatct  58020
tcagcttaat aagagtgcca agttgctttc caaagcaact ctgcctgttt tctttcctag  58080
cagcagtgtg taagactttc tgttgctcta catcaagatc aaaatttgcc agccttttc  58140
acttctgcca cattagtttg tataaaatgg taattctcta tagtcttaat ttgcatttca  58200
ctgatgacta atgaagttga acgtattttc aagtcatcaa tggccattca ggtctctttt  58260
tccatgaaat gcctgttcat gtctttcacc taattttcta ttgggttttc tgttgctttc  58320
ttagtggttt ttaggagttc tttatatatt taggataata atcatttgtc acttgtgaat  58380
tgcaaatatc tcctcccaat ttgtggctta tcttcctagg ttatttatag tgtctttgga  58440
tgaacagaag atttttattt ttgtgtattt aaattcatca gtctttttct ttgtgatttc  58500
tacttttgt gtttttaaa gaagttttcc ctatccaaag ttataaaata tttttgctt  58560
tttttctaga acttataaca ttttacattt tatatttaaa tctttatcca tctggaattg  58620
atttttgtgt gtggtggtat aagttaagga ttttattttt tccatggtga taagccactg  58680
tcccagcatc atttattata gttcacgctt tccctgctga tttgcagtgc catctttctc  58740
gcacacccca tttctacaga taagtagatc atttttcagt tccctgtttc tttcattggt  58800
tggtttggtt gattcctaac cacacggtct aattatcgag gctatttaag tcttgatatc  58860
tgaaacatga agctgtgcca actttgtgct tcatcaagga tgtcttggct atttttgttt  58920
tcattctctc tctctgtctt aatgagatag gatctagctc tgtcacccag gctggagtgc  58980
agtggcacaa tctgggctca ctgcaacctt cgtcttccgg gctcaagcga tctcccacct  59040
cagcctcccg aggagctggg actacagggg cgcaccacca tgcctggcta atctttgcat  59100
ttttttttt ttggtagaga cggggtttca ctatgttact ccaggctggt ctcaaactcc  59160
```

-continued

```
tgggctccag tgatctgccc gcctcagcct cccaaagtgt tgggattaca ggcatgagcc  59220
atcacgctcg gctaattctc tttgttataa attttagagt catctcttta agtttcttga  59280
aaaactttgt tggatggttt tgtattgaat ttatagatca atttggaaga atcgccatct  59340
tatgaaattg tctttccacc catgaaagtg atttatattg ccccatttat ttaggtcttg  59400
aatgtctttc aataattctc tccataaaat cttgtacatc ttttttaga tagatgtccc  59460
taggttcttt atttttgact tctattgcaa atggtacact tttcaaatat tacatttcca  59520
tttcttatat agagaaatgc agtttatttt tgattgcata ttgatcttac attcatactt  59580
cttttttttt tgtgagacgg agtctcactc tgtcacccag gctggagtgc agtggcgcaa  59640
tctcagctca ctccaacctc tgcctccctg gttcaagtga ttctcctgct tcagcctccc  59700
aagtagctgg gactacagac gtgcgccacc atgcccagct aatttttgta ttttttttta  59760
gtagagatgg ggtttcacca tgttgaccag gccagtctcg cactcctgac ctcaggtgat  59820
ccacccacct tggcctctcg aagtgctgag attacaggca tgagccaccg tgcctagcct  59880
tatatacata cttctcgata tgctttctta ttctcatttc tctgtagaat gtttcaggct  59940
ttctgagcag ttaaaggatc tgtgaatatc ctttgcagaa gaaatagttg tttttcttt  60000
cccacttctt attctttttc cccatgtttt tttggctggg acctccggta ctgtgttgaa  60060
tagactggtt gtagctggaa tccttgtctt cttttcctga ctttaacagg aatgtttcta  60120
acatttaaac acagaatgaa gattgctttg gggttttggt agaaatgttt ttatcaggct  60180
aaccaaattc cttttagttt ttagtttgct gagaggtttt aagtgggcat taaacttacc  60240
aaatactttt ttctgcaatt attgtgataa ttattttttc cccttttgtc tgctaatggg  60300
atgagtgaca tttttagatt tttaaaaaat taccttaaat tcctgggata aattcaactt  60360
ggtcatgatg attatgatgt ttcctttcct ttctttttt ttttttttc tttttgagat  60420
agggtttcac cctgttgccc aggctggact atagtggtgt gatcatggtt cactgcaacc  60480
tcgacctcct gggctcaagt gatcctccta cctcagcctc ctgaatagct gggatgacag  60540
gtgcccactg tcatgccttg ctactttgtt tttttttttt ttgtattttt tgtagagaca  60600
gggttttgtc atgttgtcca ggttggtctt gaacccctgg gcccaagcga tttacttgtc  60660
tttgcctctc aaagtgctgg gattacaggt gtgagccacc gtgtctggcc agattttaaa  60720
gttctaattt ggtatattta aaggactaaa caactattca ggctttctat tttttaaaa  60780
atagaaagtt atatttttga taagttatat ttgtctaggt atttggccat tttatttatg  60840
tttttaaact cagtgttatg cacttattaa tcatattctc cttgtaatct ctcttattaa  60900
attttcacca ttttatacca ttttaccctg cttagtagct gttttttttt tttttttttt  60960
gaaacagggt ctcactgtgt cgcccaggct ggagtgcagt ggtgcaatcc tggctcactg  61020
caaccctctg cctcccgggt tcaagtgatt ctcctgcctc agcctcccta gtagctggga  61080
ctacaggcac ctgccatcat gcctggctaa tttttgtatt ttttgtagag acggggtttc  61140
actatgttgg ccaggctggt ctcgaactcc tgacctcaag tgatccaccc gtcttggcct  61200
cccaaagtgc tgagattaca ggtgtgagcc accgcacctg cctgcttagt agctgttatt  61260
aacccttcag cttacaaatc aggaaacaga ggcttggaga ggggaagtca cttgtccagg  61320
ttaaatagcc agaaagtggc agagtcagga cttaaatgca agtctttctg aattgcaaat  61380
ttgtttctac tgcatcatgc tgcacctcga gggatgggta ggattcagac cgcagagatg  61440
ggaaggaaag ggcatgtgta gaggaggcac tgtatgtgca aatgtgtggt gataggcatg  61500
```

-continued ggaggagaca gggagaggtg tgactgcact aaatcctcca gtgggtgcta gagagagcgg 61560
gagatcaggg tggtgtgggc tcatgcctaa ccgctgagtc ttgctgagag acagagagag 61620
gcaggaaaca tgggctctgc tcctgggatt cactgatgag ttggggagtc aggactgacc 61680
cagggaagtc gggaccaggc taattgctat gtggatagtg gggacaatca gtgctgttag 61740
ttttgagaaa atatgccctt gggcaggagt ggtcagcatt ttggtgagat gggtatggtt 61800
gactgatggt gaggaggaag gggcactgag cctgggcaga ggtgatggtt ggaaactcaa 61860
aaggtgctag gcgcggtggc tcacacctgt aatcccagca cttgaggagg cagaggcagg 61920
cagattgctt gaggttagga gttcaagacc agcctggcta acgtggtgaa accccgtctc 61980
tactaaaaat acaaaaatta gccagggatg gtggcaggca cctgtaatcc cagctacttg 62040
ggaggctgag gcacaagaat tgcttgaacc tgggaggcag aggttgcagt gagccgagat 62100
cactccactg cactgcactc cagcctggca gacagagcaa gactctgtct caaaaaaaaa 62160
aagacaaaaa aaaaaaaacc aaaacgtgtc caggagatga gctgagctgt gcctcagcac 62220
attctctctc tttattcttc tctgccctcc acttgctggt ctgccttcca cttccttctt 62280
ttccaaacag tggaggccag gtttttgtgg tttagaatgg aaagccatgt tgattttggt 62340
ggatccttct atgcaaattt taaatgaagg acttatcact gtgggtaact ggtggcgggg 62400
ctggtgtgaa aaagccagct ggaaccttcc caaggtgttg gaatgagccc tgttgtctct 62460
gaaatcctgc ctgcgaaaac cctcagatcc tcctgggcct tgtacgtctg gagctattga 62520
ctcctgtggg tgccagtcgg tgttggccaa attgtttgtc aaataagtgc caggtttttt 62580
catgcccatc aatgcccctt aatcagggaa gcagagagag cagtggggac agcagggtct 62640
cagagtcagg tggattcaag cctgggtttg aatcctagtg cttccattta atgagcaagt 62700
agcttaactc ttctgggcct cagttttctc gtttgcacaa gaggaacaat ggtagtgccc 62760
ctgccatacg gatattctaa ggaataaatg acttaagaat tgtgctgggc actcaatatg 62820
ttagatatgg ctagctctta ttacaggctg tgcttctgta ggaaagaaac ttacttgcta 62880
attgcaaaca gtggaggaaa agtttggggt gctaccacat tgaataactg gggcctctc 62940 ctcatctgag ggtggtggga atcagggaaa gtgccaccac tgagggaggg ctgaggattt 63000
tcatttccag aagaagaaac tgagacccag agaggtcaag gaacttgagc cagaatttga 63060
attcaggtct ctctgactcc aaacctagtg ttcttttttc tgggcctcag ccctccccat 63120
aaagcatcag ctgtccagtg gttactcaca gaagatgttc cacagtcacg atggtgctag 63180
gaagagcctg ggagagtccc aaagtggaga ctttgaaggt gggcctatgg gcaaactggt 63240
ccttaggggt aggggatggg gtggggtagg aagtgtgtct caagtcccac aggggaactc 63300
ataggcaagg agagtaggga cctgtcctct ctgggcccag gaattggagg gtccttttgg 63360
gaacatcatc atcccttcct ttcctggtgg tcttatttgt agaacatctt gtgttattct 63420
taggctcagc tgtcagctgc ccagatgtgg ctctggcttt ccaggcggga ctttttgctt 63480
gtcctcagcc actgtgcact gattgcatgc ctccttgtgg ggctgtgcca gggctgccag 63540
cctttcagga tctctgggat aaactctttg attctctgcc accctcattt gctcctttct 63600
ctgccaggag agctctctgt ggagctgtcg gcccactttc cacaaagagc acgagggctt 63660
ctccatctcg ccagtttctt ctctgagttc tttgagccaa cagaagtccc tcttcttgaa 63720
actgttgcac ttgcctggtg gtgcgttacg gacactcctt ggaatcatct tttcaagctg 63780
ccttttaggt cccagaccca agatcttaca gcagagaagc accaagactc ttgtcagcca 63840
gctgccatgg ctttctggca ctcaggggct tccttccttt cctggaaatg actagtaatg 63900

```
tcaacagttg cccttgcagg tgctcgctgt gtgccaggca cggggctggg tgctttatat  63960

acattattat atttaatatt tacatcatca tattggattg taacaatttt taccttcact  64020

tgacatgtga gaatggaagt ttggagagag taggtaacat ccccacggtc acatacagag  64080

ctgggaattg atctgaagtc tttccagagc ccatctctca gtgtctacat tgcacagtgt  64140

tctcctgagg atgtttcatg aaacaaacaa gaaaagccct ccgtggcaaa agatgtttat  64200

gaaacattgc tgtttccact cctctcttga agatttaaaa tgcaaacaaa catgccgaaa  64260

gccccgagag gtcttgcagg gaagaaacct gtttgttttt gtttaaacca gaatttcaca  64320

gactccttta aaacacagaa ttcctcttcc tcctcttgct cttcttttta atgggacacc  64380

acttaatcat cttgcatacc tacgattttc tgaaacactt tggcaaccac caaattaggc  64440

cagtcttttc tctttggacc tcagtttccc catctgtaaa attaagggtt tgggcatccc  64500

accacaatgg cataactggt acttgatttg ccatccagct gtaagcaacc agtaatccag  64560

ctaaaatata ggaatcaatt gctttcagac attgaactat aggcagctga agaccgtggt  64620

tcctgagagc agagaagcaa atgaggtgaa gtcatcttca aaccatggca caggaaggtg  64680

gaacccaagc acaatggggc agcctccctg ccctggttgg agtttgagga agttgagctc  64740

atcagggggt ctcctggtga tcctgcattc attctaccag ttagttgctg agtaggaatt  64800

ctaggccagg caccggagag ggttcttgcc gggagggtca tttcagttga gagttgaagg  64860

atgagtatga gttcatcagg caagaaaagt agggggagga ggagttttgg agggagaagg  64920

acagcatatg tgaaggcaca gggagtgggg gcaggttatc taggccccac tgacagtccc  64980

ccactggacc ctgccagctt agatctgggc agagattggc ttgaaaatgt ggggagggct  65040

ggagttgaat aagcccctca cagcctcacc cagagcagga ggagggacat gcgtacaatc  65100

atgcactgca taatgaagtt ttggtcaaca atggaccacg tataccatgg tggtcctata  65160

agattataat ggagttgaaa aactcctatg acctagtgac attgtagcca tcataatgtc  65220

atcgtgcaat gcattattca cttgtttgtg gtgaagctgg aataaaccta ctgcattgtc  65280

agttgtaaaa aagtctagca catacaatta tgtgcagtac ataatagtta atgatgactg  65340

tgttactggt ttatgtattt aatatactat taatcattat tttagagtgt acttattttt  65400

taaaaagtta actgtaaaac agcctctggc aggtccttca ggaagtgtcc cagaagaagg  65460

caccattttc tttctttctt tttttattgt actttaagtt ctagggtaca tgtgcacaat  65520

gtgcaggttt gttacatatg tatacatgtg ccatgttggt gtgctacacc cattaacttg  65580

tcatttacat taggtatatc tcctaatgct atccttcccc cctcccctca tcccatgaca  65640

ggccccggtg tgtgatgttc cccgccctgt gtccaagtgt tctcattgtt caattcccac  65700

ctatgagtga gaacatgtga tgtttggttt tctgtccttg caacagtttg ctcagaatga  65760

tagtttccag cttcatccat gtccctacaa aggacatgga ctcatccttt tttatggctg  65820

catagtattc catagtgtgt atgtgccaca ttttcttaat ccagtctatc actgatggac  65880

atttgggttg gttccaagtc ttagaaggca acgttttcat aggtgatgac ggctacgtgt  65940

gtgttattgc ccctaaagac ctcccagtgg gacaagatgt ggaggtggaa gacagcgata  66000

ctgatgatcc tgaccctgtg caggcctagg ctaatgtgta tgtgtgtgtg tgtgtgtgtg  66060

tgtgtgtgtg tgtcttagtt tttaacaaaa aaaatttaaa aaacgaaaaa aaattttaaa  66120

tagaaaaaag tatagaataa agatagaaaa tatttttgta tagctgtact atgtgcatgt  66180

cattacaaaa gtcaaaaaat tcaaattaaa acatttcagt aagctaaggt taatttatta  66240
```

-continued

```
ttcaagaagg aaaactattt ttaaataagt gtattgtagc ctaagcatac agtgtttata  66300
aagctcacag tagcgtacag gaatgtccta ggccttcata ttcacttacc agtcactcag  66360
tgactcaccc aggacagctt ccagtcctgc agcttcattc atggtaaatg ccttatacag  66420
gtgtatcatt tattatgatt tttttttctt tttttgaga cagagtctcg cactgtcacc  66480
tgggctggag tgcagtggcg cgatcttggc tcactgcaac ctctgcctcc caggttcaag  66540
tgattctcct gcctcagcct cccaagtagc tgggattaca ggctcgtgcc atcataccca  66600
gctaattttt tgtattttta gtagagacgg ggtttcacca tgttggccag gttggtcttg  66660
aactcctgac ctcatgattc acccacctcg gcctcccaaa tttctgggat tacaggtttg  66720
agccaccaca cccggcccat ttattatttt tatagcgtat ttttagtgtg cattttctat  66780
gttaagatac ataaatactt accattgtgt tataattgcc tacagtattc agtacaggtt  66840
tgtagcgtag gagcaatagg ctatgccgtg cagcccaggt ccatggagta ggctctacta  66900
tctgagtttg tgtaaataca ctctgtggtg ttcgcacaaa gaccaaatca cctaacaatg  66960
catttttcgg aatgcatccc tgttgttaag cgatgcataa gtattaaatg agtgagtggg  67020
cgtgcgtgtc ccaaggcggg tgtggctatt ttctcagtcc caggacctga tctccaagac  67080
cagagtggga cgtccttggg aatgctgaac agaacagccg gggacggggt ggtcctgggg  67140
gctcggggga ggatggtttc ccagggtgtg tgaggagctg tggacctctc cacccactcc  67200
cccactggct gcggccccgc acaggctgac ggtggaactg cctgcgcagg agaaaggcgc  67260
ctattcgggt gcctggtgtt aatctgcaga ggggttggca gcagctgcta atttctgatt  67320
tgcctgtctt tgaatggggg taattgctgg gagttgccag tgttccaggt tgttctctgg  67380
aagaggggga ggaagaagca gctgtcatgg gctctgcgga gtgctgcctt ctgcaggtag  67440
catggtgaag cctcgctgga tagagtgagg ggataatgaa atctagccag gcagggccgc  67500
aagggccctc ggaggccacc tgatctgacc ggctcattct acaggtggaa ccgagatttg  67560
gagggaggga atgtgttcag gaccacacag ggtgggcctg gctaggctgc ttggctccag  67620
ccaacaaccc agctatgctt ggcattggct gtgcctcccc acccccatag accccagtct  67680
ctccaggacc cccgaggctg gggcatgtgt gtcaagaacc cttttgtctt tctctgactg  67740
caggagacca gcgcagcggt ggggtcactg aggccagcag cctcctgggg ggctccccga  67800
ggcgtccctg tggccggaag ggctccccat accacacggg gcagctgcac cctgcggtgc  67860
gtgtcgcaga ccttctgcag cacatcaacc agatgaagac ggccgagggt tacggcttca  67920
agcaggagta tgaggtgcac gccggccccg ggccagcagg atccctgcag aggcctcacc  67980
tggctcttac tctctgtgga ctctgaccct ggcaaccctc agcctagtcc tggttggacg  68040
cctgctctga cagtttccaa ctcaaccttt ttgacctcga ctctgaccct catcctaatt  68100
ttagactgat ttggtttttc actctcatgc taaccctgat ttgaaatctg accttgaatc  68160
tcgtctccat ctctatgtgg actgtgatcg ggatccttat tctgtcccta aactgaatct  68220
gcccactgac actgaccttg acctaatccc agcctgacat tgatcctgac tgtcatccta  68280
agctccattt gaactctgga tctcatccca cctctgtctg gactctgaca tcacccttat  68340
cctaatctaa atctgacctc acctttacct tctttctaac cgttattcta agcctgaccc  68400
ttattccaaa atgtctttga accctggccc tcttttcctc ttttctcatt tcccttcccc  68460
ccacatgcct tggttttgac cctggtccct ggctgataaa aggacccaca gtgacacagt  68520
gactttatct caggcccaag ttcagcttga atctggccct tatcatccca cccccatcct  68580
gcctacatca tcccccactga ggggaagggg ccctcagtga gggtccctct ctcccactga  68640
```

```
ccaccacttt tctttctggt agagcttctt tgaaggctgg gacgccacaa agaagaaaga  68700
caaggtcaag ggcagccggc aggagccaat gcctgcctgt gagtcctggg gaagggcctg  68760
gggtccaggg cagtgggtgg gagggcatca ggagggggaa cacagccagg gtgagctggg  68820
gcagcctcag agatgatagt agcattggcc accttttatt gagggcctac cacacgtcac  68880
gccctgtgct tgtttcattt attcccttca atttccctgt gaaacgggaa atactataat  68940
ccctgtttta caaataagga aactgaggct tgggagatta agattcctgc ttaaggtctc  69000
agagccagta attgcctgag cagcatacac tcttaggcct ccttgactcc atagcccagg  69060
ctctaccccc tggtgtgtcc tgcctcccat ggtgcccaga gactactggt aagccctgag  69120
actctaggtt ccctggctgc cctgcctgtg ccctatcccc tagcctccag gaatccctcc  69180
ctgactgcct agctctgggc tccccagttc agcccctgcc cacctgctct gtgtttacag  69240
atgatcggca ccgagtgaaa ctgcacccga tgctgggaga ccccaatgcc gactacatta  69300
atgccaacta catagatgtg agtgccttgc cctgtcattt ctgcagacct ggccctgccc  69360
gctccaggct tactatccag gcagggcaga aacctgtcgg gataaatggg ggttcaaatg  69420
gctgagttcg gagtgcccct atctctgcag tcagtgccag ggagctcaga ggagggagga  69480
cagtgagcag cagcttctgg aaggctttct gtaggtggga gttggcctga gagatgaggt  69540
gctttagaga agcaaagcaa agggaagagg cagacagcta ggccaagagg tgaggaaggc  69600
gggaggcatg gagaatggga ttctcatcgt gcaccatgag gctgaagagg taggcagggg  69660
ctggattgtg aagacctcaa atggcaggct caggagtggg ggcttttttcc taggggcacc  69720
agggagttgt taaagtgttt tgaccatgat cagagtggtc ctttaagaat aataacgcac  69780
atttatccag cacgtactga gtgccaagca ctgtgctaag cactttacac ccaagatctc  69840
cttttctgta atccctccac ccaccctttg aggcagttag caccatgacc tcactttaca  69900
ggtgaggaaa ccggggctca gagacgtgga gcgacttgtc ccaggttgca cagctagtga  69960
gtggtaaaga aaggacgcaa atctcagcct gtctgtgtct ctaaagcctt tgctgctgtg  70020
aggctgtcct gccccctgct gcagcagcag caggacttgg atggattgga gggaggggcc  70080
agagacagag caggcagcca ggaggcctgg gcttgggtgt caaagagagg tgatgagtct  70140
acttcctagg tgtggaagag gggcgaggcg ggacagggcc cctaatccct acagcaaacc  70200
aagtttggga gagcatcatt taatcacgta tgaaatatat tttgagcact tcctttgtgc  70260
catgcattgt gctgggcacc agggatacag atgtgaacaa gacagtcatg gcctctgctt  70320
tccttgaaca tatctatttg agtgggtgag acagatagac atgtttacaa atcaaaataa  70380
cttcagatta gatgagcaag tgcaggccag gagagagatc acacagcttg agtgttacac  70440
agcaggctag tggcagagcc agggctggtg tggcgggctt tgtggaggaa gcagggcttg  70500
agctgcctct gggtggctgg agaggagagg gaagagtgtc ccgggtgagg agctgcctaa  70560
gcaaaggcct ggggggccag gcagagcaag gcacaggtct gggagccgag gtagtcaggg  70620
tctctggagg tggcctctcc tctccctctt cttctcctcc tcctggggcc agatgtgcca  70680
tgccatgttt cccagaatcc cttgctgcct cccccactca tcctgtccct tggttggagt  70740
cagggccagg cccagcctgg aagacttggg cagctttggt gacagcgggc ctctccttgg  70800
tcttgccaag gtcccagttg gctcctcttg ggccctggca gggacatgcc actccccact  70860
ctgtggctca gcccagcccg gcctgcccgt ctccgctctg cctgccctgc tcacatcgcc  70920
cattctggcc actcctgtgc tccgtccacc tccatctgcc cctggcctaa tatctgtctc  70980
```

-continued

```
ttttgctttg tactgtttcc tcactggaat cattaagatt cggataaacc gagaagtaag  71040
tatctctctc cccttctcct cctcctcctc ttcctcctgt ctgtctgact ggctgtatct  71100
cagactctct cacggtctct ggctgtctgt ctctctgtct ctgtccttcc tttctactta  71160
tgtgcccagc accaaccgtc catttcagca gcctggccag gggctgccca gggctgaaga  71220
ttcgagagtg ttcctattgt aagcagttcc ctcccatcct ccactgcctt gagcaggggc  71280
agcagtgttg gggtgcttcc ccctgcccat tctgcactgg tcacaacagt ctgtcacctt  71340
ccttccctgg ctccgccatt cccaaggagt cctccctagc ctccctagct gcaccttcta  71400
caggaccctt tggagggtgc aggggaagct gccctggagg gccctgtttc tgctgcttaa  71460
gggtcaagat cttggacagc cccaggtcag cctcctaaaa ctactttccc tagtgttcaa  71520
ataccttcat gatcagtttg cctgaaactc aaccccgacc attttaccct caatttagcc  71580
ttaatttgaa tgtttttgg tggaagcagt ttggatagtc tgtttttaaa tattatgctt  71640
ttttttttt ttttttttt ttttttgagg tggagtttcg ctcttgttgc ccaggctgga  71700
gcgcagtggc acgatctcgg ctcactgcaa cctctgcctc ctgggttcaa gtgattctcc  71760
tgcctcagcc tcccaagtag ctggaattac aggcatgcac caccacgccc agctaatttt  71820
tgtattttta gtagagatgg ggtttcacca tgttaggctg gtctcaaact cctgacctta  71880
ggtgatccac ctgccttggc ctcccaaagt gctgggatta caggcatgag ccaccacacc  71940
tggcccattt tttagccttt taaaattaaa aaaactaccc taattcatct agctattctc  72000
taatttgatt tctttttct tttttttga gacaggttct tgctctggag tgcaggggtg  72060
tgatcatggc tcactgcagc cttgaagtcc tatgcacaag caatccttct acctcagcct  72120
cctgagtagc tgggactaca ggcgtgtgct gccatgcccg gctaattttt tcctttttt  72180
ttttttta agagatgggg tcttctcagc actttgggag gccaaggcag gcagattgct  72240
tgagtccagg agttcgagat cagcgtgggc aacatagtga gattgcctct acaaaaaata  72300
caaaaattag ctgggcgtgg tggctcatgc ctgtagtccc agctactagg gaggctgaag  72360
tgggagggtt gcttaagcct gggaggcaga agttgcagtg agtcgagatc gtgccattgc  72420
actccagact gaccaacaga gccagtccct gtctcaaaaa aaaaaaaaaa aaaaagagag  72480
agagagatgg ggtctcacta tgttgcctag gctggggatt tttaatacat atatactgtt  72540
ttcataatat ttaatgactg gtgattattt gctattttgt gggtgctttt tccattttgt  72600
ctccttttc ttttaaaaaa tatatttctt ggctgggtgc agtggctcac acctgtaatc  72660
tcagtacttt gggaggctga ggcgggagga ttgcttgagc ccaggagtta gaccagcctg  72720
ggtaacatag tgagacccca tttctacaaa caaaccaaca aacaaaaatt agttggatgt  72780
agtggcctgt gcctgtagtc ccagctactt gggaggttga ggtgggagga ttgcttgagc  72840
actggaggtc gaggctgcag tggagacagt ggcatggagc gacagcagga gggaattggg  72900
ctagacgtgg agaagttcca gtgctgaggg ctgagagtca ctgggaggct tttcgtcatt  72960
agtcactttg actatgtttt ggtcattttc gtgggaacag tgagcaggta tccagcagaa  73020
tctctgagtg tttgtcttgc tattatcctc atattgcaga ggagaacaaa ggcttagaga  73080
ggccaagagc ctggctactc aggatgtttt gaggccagca atatggacac cacctgggag  73140
ctggtgatgc ataatcccgg gccccacccc agacctttga atctgaatct gccttttaac  73200
aagatccccc gggagattta tgtctcaaga aagactgaga agcaccttct cagcgctcag  73260
agttacacag ctactgctcg gcatagctgt ggcagggacc caggtccatt caactccaag  73320
actcagattc ttcaccccat agtcaatcgc cttctgcccc agcaattctt gacttccatt  73380
```

tgatacactt gattcatttg tatcttcaag gatactgctt cagctttaaa atagtagtag 73440
taataataat ggctattact gaataagtac tgactttgtg ctagacacag tggcagacat 73500
ttaacatact actttatttg cttctcacaa cagccctcag aggtaaatgc tgtaattatt 73560
ccattttata gacatgaaaa tggaggcata gagaaatgaa ggagtttttg ctcaaaggca 73620
cacagctagt gagaggtaga gctgggattt gaaccttggc agtctggccc ctgggctcct 73680
caggcctggg aagttcacga gaccggagga gttgctggga gctgtgttga gggtgtaaac 73740
ttgaggtagg gggctgggct agttttctca gcgccagccc tgcagtacta attccccttt 73800
ccgcattgcc cgcattgatg cccttggtat ctggtgaatt cttttgctca gaaagatgag 73860
gccttgtggc aggacctcat gggtggctgt ggccctgggg tggcttgtcg gagggcaggt 73920
ttctctcctc agcttggggg ctctggggat ggaggatgaa gtagctcttg gcctctctct 73980
cgtgggaggt ggtactggta aagtgcttag cacagtacgt gaccataaca gggtcattat 74040
tattgatctt aaagatttta acattttatc caagggccat gagtaatgtc tgtgcccata 74100
tacttccatc ctgaagccct catctaggcc ccccacgctc tgagtgactg aggagtaagg 74160
gggaggggta ctgtccattc tggttatccc aagtgtgggg gctaagataa ctgacaagct 74220
ctggttatcc cacgtgtggg atctgggttg attagagctt ctggaaccct gggaacaggg 74280
cagggccatt ggggactctg tctccgaaca acagcctggc tgaaagcaga tgcctctctc 74340
cactttatgg gtggggggtc cctctaggca cataaaggag tcatgtcctc cctggggttg 74400
cacagcccag gttggattaa gcccacgact ctggtgtccc agctgtactt ctccacttcc 74460
ttggggacct ggggggatgc aaagtcatcc tgcttaggag gtcctaggga tgtgagggag 74520
cagttccctg gtggggtagg ggttctgctg ctgggagggg agggtagagg aggtgtgggg 74580
gagtgagggg ctactccctg gggtctaacc gtgccctctc ctcctgttcc agggttacca 74640
caggtcaaac cacttcatag ccactcaagg tacctggcac ttctgcccac atgcgccttc 74700
ccatgtgcct cccagcgtgc tggaatgccc tcagcttgcc tttctgcctc ccctgctgat 74760
ccgcttgatt cctgaatgtc tccccaccgt cgccatattc tggctccctg cttgttcatc 74820
tgctcccgat tctgctggat ctcttggaat ctggccaact gcctttgtcc cctctttgtg 74880
tttgtgtctc cctgatgtgc tcagtccatc tgttgctcct ggtctacctg cctgtctcca 74940
aagtggtgtc tgtaaaaggg ccagctgggc tcaggcctca tgggtgtggg ttgggcctct 75000
cggtctggtg gctgcctgga ttcttctgtt tgcatccctt tccacgactg tccatctgtc 75060
tgtccctcct ggacactcat gccattgccc aaccatctgg tcctcctcca gggtcccatt 75120
caggatgagc gggctcttta gccaggccct ctcctgatgc tacccaacct cagggcccta 75180
caggcatgcg tcagctgcaa gctgggtgtt gtgggcagca tgaagccccc gttggggctc 75240
aggaggcctc ctggcctggg gtgtggtgct ggatggtgct ggatgtgctg acctggggtg 75300
gagaccttgt ctcagggaca ggcaccctct gcctgcatcc ccagggccga agcctgagat 75360
ggtctatgac ttctggcgta tggtgtggca ggagcactgt tccagcatcg tcatgatcac 75420
caagctggtc gaggtgggca gggtaagccg ggctgtgggg cgagctgggg cgcatggcag 75480
gccaaggggg cagcaaagag cccactgagt cccgtcctgt ggggcctcta ggtgaaatgc 75540
tcacggtact ggccggagga ctcagacacc tacggggaca tcaagattat gctggtgaag 75600
acagagaccc tggctgagta tgtcgtgcgc acttttgccc tggagcgggt gagtctcccc 75660
accgcctgtt ccctgcagag ggtgcctgag cagggattag agcccactcc cacttccccc 75720

-continued

```
agccctggga gcaggagggt gaggagcgca ccactgccca tcccagcaag gaagctactt  75780
ggtcactgtt ggctgggagc actctagaag ggcaggaagg tcactgcctt tgttggtgcc  75840
cataggagga agctgagaca atgaaggggg tgacagtatc tgccaggtgc tggctcctac  75900
tctgtgctga gcctgttata aatattgttt cagtcctgga aagctccgtg tgattagccc  75960
agatacagaa agtgaggctc agagggctta tgccaggcag gagaggccac atagtcagtg  76020
gctggccagc gagtcctgtc cacgatccca tttgatctgc tctgtaaagt cctcagagga  76080
aagatagttt tttttccttt aaattaagac cctgggagtc aaaatgatat atgtttacac  76140
aacaacctgg tggcagaggt gagtatttca cagcccaggt ttaggcatca ggcagaccat  76200
tgtccaaatc ctgcatgttg ttggtttctc taaccttggg aaagtggttt ctcctctttg  76260
agccttagtt ttcttgtttg tacaatggga cattaatacc tacttcatca gtaaattgat  76320
cattgggatt agttgagatt atacaatgag atgcttactg cagtgcctgg cacacagcag  76380
gtgtctaatg gtgacagatg ctgccaggga ctctgattat tattcccatt gtctccccag  76440
agaggctact ctgcccggca cgaggtccgc cagttccact tcacagcgtg gccagagcat  76500
ggcgtcccct accatgccac ggggctgctg gctttcatcc ggcgcgtgaa ggcctccacc  76560
ccacctgatg ccgggcccat tgtcatccac tgcaggtggg ggcaccggga atcccaagga  76620
gaaaaggggc ccttctccct gggaatttgg gcttggggtc aggttggttc aggatctgta  76680
gtggggacca ggcctgggtt ctcctgctta gagatggagt gcaggaggga acgaccccca  76740
aaggccctgt cccctttggc ctttggctct gaggttggca tcttcatgtg ccccccaaga  76800
cctgtgaagc cccttgaccc aggtgctgag gaggcactgg agatagggag gggcctccgg  76860
gccgctgagg cgccaggcac gattgagttc tgcctgcttt cagtaagcag ctttttgttg  76920
cacacctgcc gcgtgctagg cctggcctgg gggtgggaag gacttcactt ctctccacca  76980
aacccagtgg gccttgccta ccccttggcc ttcacacctt ctgcagaccc tgactggctc  77040
ccgtgacccc agctgcccct cctctctctg ctttctccct ggctccacat ctttctcttg  77100
cttcttaaat ggggacccag tacgctgtcc tggcctgccc tctgtctccc cctggagagc  77160
gtaacccccca acctttgtgg ctttgtccat ggcctctgtg tctcattgcg gttcctctac  77220
tgtgttctta tcagctcccc aaatgccgca tggtagagtc gtcctccctg ccctgccacc  77280
taaaccagct tctctttgat ttctttaggc ctctttaaga tgccatcttt taaaaacaaa  77340
actttattga tatataatac acttaaagca aagtgcagaa atatgtttaa aaatatgaat  77400
tttcataaac tgagcacact tgtgaaaaaa ccagctctac tgagattaag aaacagaaca  77460
ttggctgggc acaggggctc atgcctgtaa tctcagcact ttgggaagcc aaggtgggag  77520
gatcatttga ggcccaaagt tcgagaccag cctgggcaac atagtgagac ctcattgcta  77580
caaaaataaa aaaattagtg ggttgtggtg gcacaagcct gtagtcccag ctacctgtga  77640
ggctgaggtg ggaagtttgt ttgagtatgg gagttccagg ttacagtaaa ctgtaattgc  77700
accactgtac tccagcctgg gcaacagagc gagactctgc ctctaaaaaa aaattttttt  77760
ttaaagttaa gaaaggagca gaacatgaac agttcccaga agccccccttg aacccgtttc  77820
tggcctgaat tcccccatcc ccagtcccag agaaatcact attctgactt ctaaagcgca  77880
gttagttgca catgtttttg gacttgtcat aaatggaatc atacagcatg tgctctttgc  77940
tgtttgtctt ctttccctga gccttaggtt tgtgaggctc gtccacagtg gatcatcgtc  78000
catcaagtga ataaatgaca gtgtgtttgt ccattctgcc atgataggca tttgggttgt  78060
ttccagtctt aagctattat gagtagtgct gctaaggaca ttcgatcgta tgtcttttgg  78120
```

-continued

```
ccaagaaatg tatttctttc tgtgtggtat gtacgtagga gtagaactgt tatctgtgtg  78180
aacgttcagc tttaggagat attgctgagc agttttacaa gggggttgtg ctaagttaag  78240
ccccaccagg ggtatttggg gtattcagtt gctgtatgtc ctcgctagca cgtggatgcc  78300
actgttttca aacctgaaat cttgctgtca tctttgtcca ctctccttcc ccctcagctc  78360
tgcacaacct tgcgtgagga caatgatctt gatgtgcccc cagtcaagtt agggagacag  78420
ccacataaac aatgaccatg tagcaggaag agtgttttat tgaattaatt aatttttttt  78480
ttttgagaca ggatcttgtt ctgtcatcca ggctggagtg cagtggtgtg gtcttggttc  78540
actgcaacct ccatctcccg ggttcaagcg attcttctgc ctcagcctcc tgagtagctg  78600
gaattacagg cacgtgccac cacacccggc tatttttttgt attttttggt agagacaggg  78660
tttcactatg ttggccaggc tggtctcgaa ctcctgacct caagtgatcc acccacttcg  78720
gcctcccaga gtgctgggat tacaggcctg agccaccgtg cctggccacg aagagtgttt  78780
taataaaaac ctgcccacgt tgctttggga actcaaaaga atgacatcat cctggaaggg  78840
tcagggatgc tccagtgggt atgtgaatgg gtatgagtgt gtgggctttt caaggatgtg  78900
taggagattt ggtggttttc aggaggaaag aacattcttg aattagctcg gaggatcatc  78960
attcctgttc tctcctaatc ttaagttgct aggttgagcc agtgtcacct ttgcattctc  79020
cccaccctct ctcctctcct tccctgaggc ccatcccatc tctgtcctct agcacatttc  79080
actagagctc ttccatccag cagcctgcgt cctggctcct tactcgggga ggggcagtca  79140
tctctgtgtc cgtgtcccct gtatggtgta gacatggcca gtgccctcct ctcttcttct  79200
ccttagtccc gggcttcctc cccaaagctc tgacctggtc tggggctgct ctctctccag  79260
cgcgggcacc ggccgcacag gttgctatat cgtcctggat gtgatgctgg acatggcaga  79320
gtgtgagggc gtcgtggaca tttacaactg tgtgaagact ctctgctccc ggcgtgtcaa  79380
catgatccag actgaggtgc ggggacctgg ccctgtcccc accattatta cttctaggac  79440
tggagtttct cgtgaaggat cctggagccg gcagagcatg cccaaagggt gtcctgaggc  79500
tcttgccttc cctcagatca tccctgacct tgggccgcca actgcatagg gtcatcctga  79560
actgctcccc tgtgttctgt tgggtggggt cagacaaccg gtcctgtagc tgacatacct  79620
gggattgcat cctcagtgga tgtgtgaccg tgagctgtcc cccacctctc agagcactca  79680
cagagttgtt ataggggggta gggatgaaat aggagataaa ggggcatgtc catggaggtt  79740
gtttcaggta ggcttggtcc agcctgtagt aacatggttg gcctccacct caggacaccc  79800
tgcttcaacc ttgagcttgc ttaagcccca tcaccacaga tctccagctt ctaggcccct  79860
cctcggcctc attctcatct cctgttccag gagcagtaca tcttcattca tgatgcaatc  79920
ctggaggcct gcctgtgtgg ggagaccacc atccctgtca gtgagttcaa ggccacctac  79980
aaggagatga tccgcattga tcctcagagt aattcctccc agctgcggga agagttccag  80040
gtgggggatg agtgcgtgtg tataggtgtg tgtgtgtgtg tctgtgtgtg tgttggggca  80100
tccttaatac tgcaggagtc attgagggcc aagaagcagg gaccagcctg aggccacagc  80160
tggagggaca gagctgagct accaggaagg actttgggac agcggaagat ggggtgcatc  80220
aaagcagtta agagcccagg ctttgaagtc agataaaccc aggttcaaat cctggcttac  80280
ctagttaaga gctgtgagta tccttgaaca gttcccttta cctctctgag cctcagtttt  80340
gttacccaga gaagagaagt agttaatatg tcccttgggg tgtttgtatt cattgggatt  80400
cttttggttg tgagtgatga aaatccagct tttataactg aaaagtctga ggatcgtgca  80460
```

```
gcttcagttg tagctggatc caggggctca gatgatgatg ccaacaggtg gtttctgtct  80520
gccttggttc tgctctccta tttttggctt cattctcaga cctgcacctg gccgccagca  80580
gtgctgggct cccatcatct ctattgtctg gtgacttagg aaaaaggcgc ttgctgctcc  80640
cagcatcccc ccaacagtcc tagatcagac tttcatgttc ccatccctgg accagtcaca  80700
ggttggagag gtggagctca ctgattgccc ctggctctgg tcacatgccc aaggcctggc  80760
tcttggggca ggaccagcct caccatatca catggctgag atgggaaaag gctggttctc  80820
cagagaagcc tgagagcgat cactgggtgg cagagacctc agaagtcccc tccactccag  80880
ggttcctgca gtggctcagc aggatggcac gtgctgggga cctggcactt ctcacaggag  80940
gtgcagggtt cccggaggag ggtgtcaggc tttggggatc atgatagact gtggttccct  81000
gtgagggatc tccaagaaca agagaaagaa actgagagcc cctgggtctg gatgcgtgag  81060
gtgtgaaggc atgcgggcgg aggagatgcc ccggagatcc aggtgtgatt cagtgcccgg  81120
tgcttaggac ttcattctgt tcagacaggg ccgtgaccaa ggaacgtgac cccctctcca  81180
cgtgcctgga gtccgcttct tggagggtgt ggggtttcag gggttgcctc agtgaaggca  81240
ctggtcagct agtaaagttc ctcactgtgc ccgtgtgtgc cgagctcagc ccagtgcttg  81300
tcatgatctc actttggcct cccagcagcc ccatgaagta ggcatattac ttccctattt  81360
cacagtcgag gaaactgagg ctgagagatg cagtagcttg tctgaggtta tgtgggtggc  81420
aaggaggtag actctggtct ctagagctct atccaggccc tataatggcc tagagacagg  81480
gagtctggct ccgtgccctg tacccttctc tctggacctc agtttctcca tccataaaat  81540
gggattagta actcagtcca gcctccttca tggggatgtg aggaggccca gcaagccctg  81600
gacgtaactc tctgtcccca cccccgctcc ctgtagacgc tgaactcggt caccccgccg  81660
ctggacgtgg aggagtgcag catcgccctg ttgccccgga accgcgacaa gaaccgcagc  81720
atggacgtcc tgccgcccga ccgctgcctg cccttcctca tctccactga tggggactcc  81780
aacaactaca ttaatgcagc cctgactgac gtgagagctt ggggtggagt gggctctggg  81840
gctccccttc ccagcagcat cagggaaggt ccaggggcca cgggaacaaa gctgaaggct  81900
ctgttggggg gacccctgcc cattctgggg aacaggcctg tgtgtgaccc tcctactcct  81960
agggagcttc cattcagggc attcaagcca gtgcccccca cactctgcct cagtggggtc  82020
tggttgtgga gttcaggcag ggctgtctcc aagattaggc ccagcagagc ctggggtagg  82080
atgagtgatt caggggactt tggctgggga gacctcgagg gtttggggat ggaactcgag  82140
acctgatgtc tggaagcagg ggagcttgtc ctggggagaa tgagctggag tctgctccag  82200
gaccaggcct gggacagtga tctctggccc cattcttccc tgggtgggca tgggccctct  82260
gagggctcag gagcctttta gaagtctctt tccctgcttc aagctcaggg gctctgcctc  82320
ctttactgag ggttgcaagc agctcaggag atgggtgctg gcattttagt cccctgctaa  82380
atggctccaa gatgctgctg tctgaggcgg gaagggtcta ggattattat ccctattcct  82440
ctgccacact ggaaccagtt cagatataga cacaggagac acacgggtgg agatcatatg  82500
ttatagataa aactggagat ggagtttgag atgtgtggcc agttggtggg ccgctccttc  82560
acccctcccc gatatagccg tgcaaccgca ggccacccct ccccgtcagg gactggcctt  82620
tactggcagg gagcaggagc aattgagtgc acactttcca agggtaggct ggcctggaaa  82680
aagaggaagg agtggagcca agcagcctcg ctcatgggag gagtgagtga aggatgggcc  82740
agggccaggt gtgtcactgc tgcgtctctc cacgcggaaa tgagggatgc cgatggggaa  82800
ggttctccca cagcggttaa gagggagatg ggctttttgc ggcctgatgc ctggccagga  82860
```

```
actccttggc aggacagtgc gggggacagc ggggtttctt taaagagggt aaccacccag  82920
ggggcttccg ggtgtcagct gaaggggagg ggaagagctg ccctagccac tgatgagaga  82980
tgtgaggggc ccatcagtca ctgtcactca gcttggtgga tggaatgtgt gtgcccacat  83040
gctcgccggg ggacatctgg cctgctgagg ggtcaggggt cctggagggg tggcatgtag  83100
taccgggaag atctttgaac taaacttagg aagctgtgcc ctcccgccca gccccctcct  83160
tggccttggt gtgcccatct gcacattggg ggcctggaaa ggagactgtc tgagggtcct  83220
gagctggggc tccctggccc tgatgggtgg gttatcacgt ggaaaagttc tgagacagcc  83280
ctgtcccctc ctgaggtcct tgatgcctct gacgtctgac cccagccatg caggtcctat  83340
tggcttggag ccaggaggcc ccatttctca gacaggccct gaactcgtca gtgaggggcc  83400
agctggagtc tttgtggtgg tcaagtctgc aaggagccct gttgggcacc caggcctgag  83460
ttttggaatc tggctgggcc tggccttgag gagttgttaa tcaggagcct tcagagagtc  83520
ctggagagag atcgctgggg gaccaggggg gctctttgtt tctctgcact gcaccttgca  83580
ggattacaaa gggcagatca atatttggtt agggcccaag tcagggtcaa ggccagaaga  83640
agccagacaa agaccagggt catgggagct tgtgccagcc cctaggtcag gaggaagact  83700
gggggacagg agaagagctc ggggaaggga ggggggacat ggcacagggt ggggcagggc  83760
aggtcaccag gggaggctgg gagctagatc tttaatggga gaaggccggg tgccagcccc  83820
cctggcagga cgagggagca gtgagcagcg tcggggcctg tcactgcctg gagagcctgg  83880
ggccccagac ccttcactta tggagttgga agggacctag agatttattc aaaatattta  83940
ttgagcccct acagggttct gggtggagac catacctag aagctctgct ctcctgaacc  84000
ttgcttttag caggtggagt gggatagtca ggaaatatac aatgaaatgt catcaactgg  84060
aaatttctac aaaaacagcc aggcagtgtt taatgtggat ttggggtgtg tgtggggcta  84120
tttttgatga ggtggtgggg gagggcttct ttgaggaggt gataagtaaa gaccagaagg  84180
aagtgaggga gacagccata tagacatttg ggaaatttgg cctaggcagc caaaatagca  84240
gatgccgaag cgcggaggca gggagtaagc tcggccagcc tctgccttga gctcagcctc  84300
atgcccaagc tcccctcgcc atacctttgg aaacttttgc tgtttagttc tggggggtca  84360
tgggcttggt ccccagaggc ctgggcccac cctgtcaacc caggcctcag tgtgccaacc  84420
aacatcagaa atggcccact ggaggcagcc tggtcctgtg gggcacaacc gtccaactca  84480
gggtgggcag tgcgggaaga cagcctgggg cagaggctca gcccaggcca ggggccggga  84540
acagggccct gctgagttcc ggtttccctg cagagctaca cacggagtgc ggccttcatc  84600
gtgaccctgc acccgctgca gagcaccacg cccgacttct ggcggctggt ctacgattac  84660
gggtgcacct ccatcgtcat gctcaaccag ctgaaccagt ccaactccgc ctgggtgagg  84720
cctccactgg ccaggccaat gggccgcctg ctcccaggtc ctctgtgtat tcagggccat  84780
ggtccccaaa gccaaaagtt gggtcccagc tctgccatct atttattgtg tgatgaatca  84840
tacaccttcc cagagcctca gtttcttcat ctgtaaaaca agggtgtcag atgggagatc  84900
actagttgct ctttttcttt tctttttttt gagacaaggt ctcactcttt tgcccaggct  84960
ggagtgcagt ggcgcgatca cagctcacta agttgtgcag cctcgacctc ttgggcccaa  85020
gccatccttc cacctcagcc tatcgagtag ctgggactac aggctgcatc accacagctg  85080
tctgattttt tttttttttt tttttttca gtagagacaa ggtctcactg tgttgcctgg  85140
actggtctcg aacacctggc ctcaagtgat cctcccacct tggtctccca aagaactggg  85200
```

-continued

```
attataggca tgagccactg cctctggcca cagttgctct ttattggccc cctgctaagc  85260
cagggactgc tttgcactca tggtcttatt tagaatctat aatgaccttg gagggaaggc  85320
ttcagtgaga aaattaagac ccaaagaggt tcagtgcctt ctccagggcc acatggctgg  85380
ggaggggcag agctgtgctc cccagcctca gctgcctcat tccagagctt ctgctctttt  85440
agtcactcca ctaaagcgcc catcatgggg gcctccgagg tagagtacaa ttcaagcctc  85500
ctactttctg actgtttgat ctagggtaag ttgattgacc tcttttgagt tttactttcc  85560
ttctctgtaa aatgggggcc atcataggac ctgttcttgt ggggttattg tgaggaccag  85620
gtcaggtgtg cataggatat gtggcactgc tgtgtctgct gcacagtagg catgtggtat  85680
gtggcaggga caaagatgat gagggtgaca gttgtatctg agattggccc agacactggt  85740
tcagtgacct cagcctgggg gcagcccctc tgactcccct gtttcccttt ggagctccca  85800
agaagtacag atacccagcc ttccagccct gcctgaccat gtgctttagg tctctggacc  85860
ccttcccacc ccagctttct gctgggccca gggggctagg aagatttgct gtaaaatgag  85920
tacaacagct tcttaatggc ctccttgaga agattgcatt aactgggctc tttatgagtc  85980
aggcactttg tgaaaatgac ccaggactac aggataatgg gcctcagccc tggtgcagca  86040
ggaaccatcc ttgctagggt agaggggaga ggcccagagg gaggctcaca gagatgtagt  86100
tcactgggca ctgatttgct catctgctca accaactttg cccatgaaca gctccctgca  86160
gtgggcaggg aggagacaga gggagaagag acacagcccc tcccagatct catggtccag  86220
gaggaaacag gtagaaaaac tgatagtgac agcacagagg gaaaagagct atgaaagagc  86280
tggcacaggg acagagaagt ccgggggatc atgtatcggc gatggcttcc tggaggaggt  86340
agtgtctgag ctgagatgtg tgggaagggc agaattaact aggtgaggag gtggaggaag  86400
agagacccgt ggagagggag cagcctgtgc agggttctga acgcacaggg ttgccaggac  86460
ctgaggcaaa atgaggaagg tggtgtcctc ctgtcctggg ctgtggtcag aggggattga  86520
tgagcacggt gtctttttgg gagaggatgg gagtcatttt accgacggag aaactgaggc  86580
caagagaaag gaagagcctt tcctgggctt caggcagagc tgagactaga aactgaggct  86640
caggatactt agcctggagg atgtgtgtgt gtatttgtac gtgtgtttgt gtgtgttagg  86700
tcatagggct gtacctcctc tgtccctcca cagtctggag tctgggaggg ggttgtattt  86760
aggaccctga ctccatggag gggtcctggg gcagaagtgg gggtactgaa ctgtgttgca  86820
gcatcaggga caccccacct ctgtgagctg gtgctgaagg gcagaggcag tgagagagaa  86880
ggctgggggg aggttctggg gtgggtggga gtgatccagg cctattcctg gaagcaggca  86940
gcctcatgta ggagcgtgtg aaccggttaa ggtgtagctt tctagctgca cagcagtagg  87000
catcagtgca gtttgcaaag ggttcatctt ggctgatctg aacgtgtcag tgcagaacgc  87060
attggggcag gtgggccttg cagcctgtgg gcaactggtg gtgattgggg gagctgctga  87120
aggtgagtct ggagtgagtg ggtgggccag ggttcgtggg agccacaggg caagtgtgga  87180
gcccttgggg tgggcatggc tgtggggtga gccccggcca ggctctactc agctctcccc  87240
tctccgtgct tatgcccagc cctgcctgca gtactggcca gagccaggcc ggcagcaata  87300
tggcctcatg gaggtggagt ttatgtcggg cacagctgat gaagacttag tggctcgagt  87360
cttccgggtg cagaacatct ctcgggtgag tggtctgagg agccccaggg aaggaccctg  87420
ggtggtggct ggggcagctt ttaatgaccc tctgtgtcat caggggcccc tgggaccctg  87480
gtgctcatgt cctccctggc tggctgcccc tgtccccagt tgcaggaggg gcacctgctg  87540
gtgcggcact tccagttcct gcgctggtct gcataccggg acacacctga ctccaagaag  87600
```

gccttcttgc acctgctggc tgaggtggac aagtggcagg ccgagagtgg ggatgggcgc 87660
accatcgtgc actgcctgtg agtacctgcc ctgtgggagg gcgggtggag gggttgggga 87720
gccaggggca gaggtccagt ctgaaagggt gccagctttg gctggactgc aaagctggca 87780
ccgaaacccc tgggctctta gatggctgtg gccaggatgc tgcccaacca gccaaggctg 87840
gccctggagg aatccagtga gtttccaggc tatagactca gccctgaaca actgcccagt 87900
atcctctgtg tgatgtctga ctttgccaat ttaattagag tccttggtca gaatttttta 87960
ccccatgaga ttgtggcaca cttttatgcc aatagaattc cagtctttgt tcatgcatgc 88020
acacatgtga ctttttccat ccatccatcc atccacccat ccatccatcc atccatctgc 88080
atgccccatt cataagttca tgtattcact catgtctggg tgcagtcact cctttgctcc 88140
ccacttttc atgctttcag catttactga gcctttcgag tggcaggctg ggcctactgg 88200
aagctggtgc ggagctgagt cagtccgggt ctggccccca ggggttttgg ttctggtggg 88260
aaagacccct gagaagggga gtgagggccg catcagtctg ccattcccca ggaggcaccc 88320
cacacgtgga gtcacaggga aggagggaga ggcacggagg ggatggagct ctgtgggagg 88380
ctgtgggttt gacttggggt ttgggtacgt ttgtgcctgt gtgcccacga tgccaggtgg 88440
tgaccagtct tctcagcatt cctgttccac cttgctctct gggtacgcgc ttgctgctcc 88500
tccgcccttc tttgtcactg tctttgtctc tccgggtgtt tctcttggag tgtgtctggc 88560
ctcctttctc tcagaatccg cagtctgttt cgccttgaga atatgtcttc tgagatgtct 88620
tagcctctga tccttcttaa cctggtcctg ctcctccctc tgggttccct agccccgccc 88680
cttacctctg ggtcctctgc cccgcccttc tgagttccct agttctgccc ctcaccttgg 88740
gctctttggc cctccttagt ttcctagccc cgcccctcac ctctggactc tttggcccct 88800
cctttctggg tttcctagct ctgcccctca tctctgggct ctttggcctc ttccttctgg 88860
gttccctagc tccgcccctc tcctctaggc tctcgggccc ctcctttctg tgttctctaa 88920
ctccgcccct cacctctggg ctctctgccc cacccttcta gattccctag ctccgtccct 88980
ctcctctagg ctctctgccc ctccctcgtg gttccctggc ccttttctta ccttcaggtt 89040
ccaaggcccc gcccctcagc ttttgcatct ctcattcaga aacgggggag gacgcagcgg 89100
caccttctgc gcctgcgcca cggtcctgga gatgatccgc tgccacaact tggtggacgt 89160
tttctttgct gccaaaaccc tccggaacta caaacccaac atggtggaga ccatggtgag 89220
gggctgtgtc ccgtgcccag ccacttccac cttcctggtc catgccaggc caggttcctt 89280
agcacccact ctcccatatc tgggccccac cactgggcct tggttctagc cctgtggtcc 89340
taaaacatta cccccatttc tcccttctcc ccgagggcgg gcctgggctc gggctcgtgc 89400
ttgccctctc actccccgtt cccctccccc cacaatactg gagttggggt caggctcatg 89460
attccctccc tctcttcctc tccccaggat cagtaccact tttgctacga tgtggccctg 89520
gagtacttgg aggggctgga gtcaagatag cggggccctg gcctggggca cccactgcac 89580
actcagggcc agacccacca tcctggactg gcgaggaaga tcagtgcctc ctgctctgcc 89640
caaacacact cccatggggc aagcactgga gtggatgctg ggctatcttg ctcccccttc 89700
cactgtgggc agggcctttc gcttgtccca tgggcgggtg gtgggccaag gaggagctta 89760
gcaagtctgc agcccagccc cacctccata gggtcctgca ggcctgtgct gagaggcctg 89820
gtgctgcctg gcagagtgac aaaggctcag gacggctggc tctgggggac tcaggccaag 89880
ccccttggca ccatcctggc ttttggcagg gatgagtgag gccctgcaga gagcatccca 89940

```
ggccaaggtt cccactcagc ctgccccctc tgcatgtggg tagaggatgt actgggactt  90000

ggcatttagg attccatctg gcccagcccc tgaaggtcct ggggaagcag gtctcaattc  90060

tgaatagcca gtggggcaca ctgactgtcc tccccagggg aactgcagcg ccctcctccc  90120

cactgccccc tgcagcccct gagatatttt gctcactatc cctccccact tgcttccctg  90180

atatgtgctc tgagcttccc tgaaccagga tctgcctatt actgctgtgc cccatggggg  90240

gctccttccc tgcctgaccc actgttgcag aatgaagtca cctcgccccc ctcttccttt  90300

aatcttcagg cctcactggc ctgtcctgct cagcttgggc cagtgacaat ctgcaaggct  90360

gaacaacagc ccctggggtt gaggcccctg tggctcctgg tcaggctgcc cgttgtgggg  90420

aggggcagtg ttagagcagg gctggtcata ccctctggag ttcagaggaa gaggtaggac  90480

cagtgctttt ttgtttcttt tgttattttt ggttgggtgg gtgggaaggt ctctttaaaa  90540

tggggcaggc cacaccccca ttccgtgcct caatttcccc atctgtaaac tgtagatatg  90600

actactgacc tacctcgcag ggggctgtgg ggaggcataa gctgatgttt gtaaagcgct  90660

ttgtaaataa acgtgctctc tgaatgccac agagcagccc tgtgtgtgtc tcaccagcct  90720

gacggggcct gctcacctgc ccccagcctc cagtgcagtg ggagggccct ggagaagcct  90780

gggttctgat ctggtcctgg tttttccatt cgtaaaatgg tgggagtgtg gaccaggaca  90840

tcactcaggg tccttccact ttcagagttg gttccaaggg accctggcca ttgctgtccc  90900

catccaggcc tctgaagcag ttcctcaggt agggtatatc aactcgagat ccctgagggc  90960

cacagagctg cctctcactc cactgggggc cctggatcag gttcagctct ttctggggca  91020

gcatgggagg ctcaggcttt ggtgtcaggc agatgggccc agcagctgcg agaccctggg  91080

caagttagt                                                         91089
```

<210> SEQ ID NO 5
<211> LENGTH: 5732
<212> TYPE: DNA
<213> ORGANISM: M. Musculus

<400> SEQUENCE: 5

```
gttgactact cagctgccag aacatccaat ctggctcctg caactttaga ccaacatatt    60

gtgtttgatc ttctcctgaa caacttggga gatacgtctg atcttcagct tggtacatac   120

agttgcgcag tgaatggcac ttacgtgttc attgtgcaca tgctaaagct ggcatgatta   180

atgttcgact gctatgtcaa cctgattaac aatgaggatg tcttggtgtc agctatgcca   240

acgatggtgc tccagaccgg cgccagtccc gctccgcgcg gcactgtcca ctacggctcc   300

cgctcgcctt gggctcccgg tcgggctccg gaggcgtcgc ctccccagct gcgggtctcc   360

aggacctagg cggcggccat ggcccgggct caggctctgg tcctggcgct caccttccag   420

ttctgcgcgc ctgagaccga gactcccgca gctggctgca ccttcgagga ggcgagtgac   480

ccggtcgtgc cctgcgagtt cagccaggct cagtatgacg acttccaatg ggagcaagtg   540

cggatccacc ccggcacccg gacccctgaa gacctgcccc atggtgccta cttgatggtc   600

aatgcttctc agcataccc aggtcagagg gcccacatca tcttccagac cctgagcgag   660

aacgacaccc attgtgtgca gttcagctac ttcctgtaca gcagggatgg gcacagccca   720

ggcaccctgg gggtctacgt gcgcgtgaat gggggccctc tgggcagtgc cgtgtggaat   780

atgaccggat cccacggccg tcagtggcac caggctgagc tggctgtcag caccttctgg   840

cccaatgagt ttcaggtgct gtttgaggcc ctcatctccc cagaccacaa gggctacata   900

ggcttagacg acatcttgct cttcagctat ccctgcgcaa aggcccctca cttctcccgc   960
```

-continued

```
cttggggacg tggaggtcaa tgcaggccag aacgcatcct tccaatgcat ggcagcaggc   1020

agagccgcag aggcagaaca cttcttcctg cagcgtcaga gtggagtgct ggtgcctgcg   1080

gccggggtgc ggcacatcag tcaccgtcgc ttcctggcca cttttccgct ggcctcggta   1140

ggccgctcag agcaggatct gtaccgttgc gtgtcccagg ccccgcgtgg tgctggcgtc   1200

tccaactttg cagagctcat cgtcaaagag cctcccaccc ccatcgcgcc cccacagctg   1260

ctgcgtgcag gccccaccta cctcattatc cagctcaaca ccaactccat cattggcgac   1320

gggccgatcg tgcgcaagga gatcgagtac cgcatggcac ggggcccgtg ggccgaggtg   1380

cacgctgtca acctgcagac ctacaagctg tggcatctgg acccagacac tgagtatgaa   1440

atcagcgtgc tgctcacacg cccgggagat ggaggcacag gccgccctgg gccaccactg   1500

atcagccgga ccaagtgcgc agagcccacg agggccccca aaggtctggc ttttgctgag   1560

atccaggctc gccagctgac cctgcagtgg gagcccctgg gctataatgt cacacgttgt   1620

catacctacg ctgtgtccct ttgctatcgc tacaccctgg gcggcagcca caaccagacc   1680

atccgggagt gtgtgaagat ggagcggggt gccagccgct acaccatcaa gaatctgctg   1740

ccattcagaa acatccacgt gcgtctgatt ctcacaaacc ctgaggggcg caaggagggc   1800

aaggaggtca ccttccagac agatgaagat gtgcctggtg ggattgcagc tgagtcccta   1860

accttcactc cactggagga catgatcttt ctcaagtggg aggagcccca ggagcccaat   1920

ggcctcatca ctcagtatga gatcagctac caaagcattg agtcctcaga cccagcagtg   1980

aacgtgcccg gcccgagacg caccatctcc aaactccgga atgagactta ccacgtcttc   2040

tccaacctgc atcccggcac cacgtatctg ttctccgtgc gtgctcggac gagcaagggc   2100

ttcggccagg cggctctcac tgagataacc accaacatct cagctcccag ctttgattat   2160

gccgacatgc cgtcacccct gggcgagtcc gagaacacca tcactgtgct gttgaggccg   2220

gcccagggcc gaggagcccc catcagcgtc taccaggtgg ttgtggagga agagcggcca   2280

cggcgcttgc ggcgggagcc cggagctcag gactgcttct cggtacctct gacctttgag   2340

acggccctgg ctcgcggcct ggtgcactac tttggggctg aactggctgc cagcagcctg   2400

cttgaggcca tgcccttcac cgtgggtgac aaccagacct atcgtggctt ctggaaccca   2460

ccgcttgagc ccagaaaggc ctatctcatc tatttccagg cagcaagcca cctgaaaggg   2520

gaaacccgac tgaactgcat ccgaattgcc aggaaagctg cgtgcaagga gagcaagcga   2580

cccctcgaag tgtcccagag atcggaggag atggggctca tcctgggcat ctgtgcaggt   2640

ggtcttgccg tcctcattct cctcctgggg gccatcattg tcatcatccg caaagggaag   2700

ccagtgaaca tgacgaaagc cacggtcaac taccgccagg agaagactca catgatgagt   2760

gccgtggacc gcagcttcac agatcagagt actctgcagg aggatgagcg gttgggtctg   2820

tcctttatgg atgctcctgg ctatagtcct cgtggagacc agcgaagcgg tggtgtcacc   2880

gaggccagca gcctcctggg ggttctccca aggcgcccat gcggccggaa gggttctccg   2940

tatcataccg ggcagctcca ccctgcagtc cgagtggctg accttctaca gcacatcaac   3000

cagatgaaga cagccgaggg ctacggcttc aagcaggagt acgagagttt ctttgagggc   3060

tgggacgcca ccaagaagaa agacaagctc aagggcggcc gacaggagcc agtgtctgcc   3120

tatgatcgac accatgtgaa actacacccg atgctggcag accctgatgc cgactacatc   3180

tctgccaact acatagacgg ctaccacagg tcaaaccact tcatagccac tcaagggcca   3240

aagcctgaga tgatctacga tttctggcgc atggtgtggc aggaacagtg tgcgagcatc   3300
```

-continued gtcatgatca ccaagctggt agaggtgggc agggtgaagt gttctcgcta ctggcctgag 3360
gactcagaca tgtatgggga catcaagatc acgctggtaa agacagagac actggctgag 3420
tatgtggtgc gcacctttgc cctggagcgg agaggttact cagcccggca tgaggtccgc 3480
cagttccatt tcacagcgtg gccagagcat ggtgtcccct accacgccac ggggctgctg 3540
gccttcatcc ggcgtgtgaa ggcttccact ccacctgatg ccgggcccat tgtcattcac 3600
tgcagtgcag gaactggccg cacaggctgc tacatcgtcc tggatgtgat gctggacatg 3660
gctgaatgtg agggggtcgt ggacatttac aactgtgtga agaccctctg ttcccgacgg 3720
gtcaacatga tccagacgga ggaacaatat atcttcatcc acgatgcaat cttggaggcc 3780
tgcctgtgtg gggagaccac catccctgtc aacgagttca gggccaccta cagggagatg 3840
atccgcattg accctcagag caattcctcc cagcttcggg aagagttcca gacgctgaac 3900
tcggtcacgc cgccgctgga tgtggaggag tgtagcattg ccctgctgcc ccggaatcga 3960
gacaagaacc gtagcatgga tgtgctgcca ccagaccgct gcctgccctt cctcatctcc 4020
agtgatgggg accccaataa ctacatcaat gcagcactga ctgacagcta cacacggagc 4080
gccgccttca tcgtgaccct gcacccgctg cagagtacca cgcccgactt ctggcggctg 4140
gtctacgact acgggtgcac ctccatcgtc atgctgaacc aacttaacca gtccaactcc 4200
gcctggccct gcttgcagta ctggccggag ccaggccgac agcagtatgg gctcatggag 4260
gtggagtttg tgtctggcac agcaaacgag gatttggtgt cccgagtgtt ccgggtgcag 4320
aactcttctc ggctgcagga gggtcacctg ctggtacggc acttccagtt tctgcgttgg 4380
tctgcttatc gggacacgcc tgactccagg aaggcctttc tgcacctgtt ggctgaggtg 4440
gacaagtggc aggcagagag tggggatggg cgcaccgtgg tgcattgtct caacgggggt 4500
ggccgcagtg gcaccttctg cgcctgtgcc acggtcttgg agatgatccg ctgtcacagc 4560
ctggtggatg ttttctttgc tgccaaaaca cttcggaact acaagcccaa tatggtggag 4620
accatggatc agtatcattt ctgctacgac gtggccctgg agtacctgga ggctctggag 4680
ttgagatagc aggcgcctga cctggggcac ccagtgaaca cccagggcat ggcccatcat 4740
cccagatgag gagggcctgt ggccccaact ttgctcagcc ataattccac agggacaaca 4800
ctggaacgga cggacactgc accatcttgg tgacccccac gggaaggctg caggccaagg 4860
agaagctttg caagactgta tcagccccac ctctagaggg ccctgcagac ctgtgcagag 4920
aagctcgcct ggaccaaaat agctagtgct ggagagcaca ggccaggccc ctctgctcca 4980
tcacagtcct tggccagaaa tgaatgagtg tctgcagaga gcacccatgg tttgcaccca 5040
gtatggtcct ttctgcacgt ggtggaggct cactgggact tggcaggggc tgagtccccg 5100
agagtcctga agctgggact cttccccgtc tcgccggtgg gacccgctga gcatcctgca 5160
gctccattct ccatccccac tgcccctaca gacctggggt gctttgctcg ctttcctcct 5220
gcttctgagc ttttcctgca acaggacccg tgcctccttc ctgggctcca tccctgcctg 5280
gcccagtata tgcagaatga tatacttcag ctccttcttc ccctggcctt tgggtctcca 5340
tggttcagtc ctgctcagct tgggcctgtg acaatccaca aggctgaatc acagcccctg 5400
gggttgaggt ccctgtggct cttggtgagg ctgccactgg atcggggcag gctagaacag 5460
ggctggtgtc agctcctaga gtacagagga agaagggata ctttggaatg gaggaccagt 5520 gcttttttttg ttgttgttat tttgttattt ttttgatggg agggtgggaa gttctcttta 5580
taatggggta ggccacaccc ccatttcgtg cctcaatttc cccatctgta aactgtagat 5640
atgactactg acctacctca cagggggctg tggggaggtg taaggtaatg tttgtaaagc 5700
gctttgtaaa taaatgtgct ctctgaatgc ca 5732

<210> SEQ ID NO 6
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 6
cgtgtgtctg tgctagtccc 20

<210> SEQ ID NO 7
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 7
ggcaacgtga acaggtccaa 20

<210> SEQ ID NO 8
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 8
gcccattgct ggacatgc 18

<210> SEQ ID NO 9
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 9
agcccattgc tggacatgca 20

<210> SEQ ID NO 10
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 10
ttgtcccagt cccaggcctc 20

<210> SEQ ID NO 11
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 11
ctttccgttg gacccctggg 20

<210> SEQ ID NO 12
<211> LENGTH: 20
<212> TYPE: DNA

<213> ORGANISM: Artificial Sequence
<220> FEATURE:
<223> OTHER INFORMATION: Oligomeric Compound

<400> SEQUENCE: 12
gtgcgcgcga gcccgaaatc 20

<210> SEQ ID NO 13
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 13
atccaagtgc tactgtagta 20

<210> SEQ ID NO 14
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1, 2, 3, 4, 5, 6, 7, 8, 9, 10, 11, 12, 13, 14, 15, 16,
17, 18, 19, 20
<223> OTHER INFORMATION: n = A,T,C or G

<400> SEQUENCE: 14
nnnnnnnnnn nnnnnnnnnn 20

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
gccctccatg ctggcacagg 20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
agcaaaagat caatccgtta 20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
tacagaaggc tgggccttga 20

<210> SEQ ID NO 18
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 18
atgcattctg cccccaagga 20

<210> SEQ ID NO 19
<211> LENGTH: 15
<212> TYPE: DNA
<213> ORGANISM: Artificial Sequence
<220> FEATURE:
<223> OTHER INFORMATION: Oligomeric Compound

<400> SEQUENCE: 19
agtgctgaca gccag 15

<210> SEQ ID NO 20
<211> LENGTH: 15
<212> TYPE: DNA
<213> ORGANISM: Artificial Sequence
<220> FEATURE:
<223> OTHER INFORMATION: Oligomeric Compound

<400> SEQUENCE: 20
gctgacagcc agctc 15

<210> SEQ ID NO 21
<211> LENGTH: 13
<212> TYPE: DNA
<213> ORGANISM: Artificial Sequence
<220> FEATURE:
<223> OTHER INFORMATION: Oligomeric Compound

<400> SEQUENCE: 21
gtgctgacag cca 13

<210> SEQ ID NO 22
<211> LENGTH: 24
<212> TYPE: DNA
<213> ORGANISM: Artificial Sequence
<220> FEATURE:
<223> OTHER INFORMATION: Oligomeric Compound

<400> SEQUENCE: 22
agtgctgaca gccagctcag cctg 24

<210> SEQ ID NO 23
<211> LENGTH: 14
<212> TYPE: DNA
<213> ORGANISM: Artificial Sequence
<220> FEATURE:
<223> OTHER INFORMATION: Oligomeric Compound

<400> SEQUENCE: 23
gccagctcag cctg 14

<210> SEQ ID NO 24
<211> LENGTH: 35
<212> TYPE: DNA
<213> ORGANISM: Artificial Sequence
<220> FEATURE:
<223> OTHER INFORMATION: Oligomeric Compound

<400> SEQUENCE: 24
agaaagtgct gacagccagc tcagcctggt gccac 35

<210> SEQ ID NO 25
<211> LENGTH: 27
<212> TYPE: DNA
<213> ORGANISM: Artificial Sequence
<220> FEATURE:
<223> OTHER INFORMATION: Oligomeric Compound

<400> SEQUENCE: 25
ctgacagcca gctcagcctg gtgccac 27

<210> SEQ ID NO 26
<211> LENGTH: 23
<212> TYPE: DNA
<213> ORGANISM: Artificial Sequence
<220> FEATURE:
<223> OTHER INFORMATION: Oligomeric Compound

<400> SEQUENCE: 26
cagccagctc agcctggtgc cac 23

<210> SEQ ID NO 27
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 27
cagccagctc agcctgttgc 20

<210> SEQ ID NO 28
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 28
cagccagctc agcctggtgg 20

<210> SEQ ID NO 29
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 29
ttgccagctc agcctggtgc 20

<210> SEQ ID NO 30
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 30
caggcagctc accctggtgc 20

<210> SEQ ID NO 31
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 31
cagtcagcac agccttgtgc 20

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
gagcctgagc gagaatgata cc 22

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
gggatccagt catattccac aca 23

<210> SEQ ID NO 34
<211> LENGTH: 21
<212> TYPE: DNA
<213> ORGANISM: Artificial Sequence
<220> FEATURE:
<223> OTHER INFORMATION: Probe

<400> SEQUENCE: 34
cgtctacgtg cgcgttaatg g 21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
gcccagaaag gcctatctca t 21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
gcaattcgga tgcagttcag t 21

<210> SEQ ID NO 37
<211> LENGTH: 23
<212> TYPE: DNA
<213> ORGANISM: Artificial Sequence
<220> FEATURE:
<223> OTHER INFORMATION: Probe

<400> SEQUENCE: 37
aggcagcaag ccacctgaaa ggg 23

<210> SEQ ID NO 38
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 38
gcacgggcca tggttggagc 20

<210> SEQ ID NO 39
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 39
tcgaaggtgc agccagctgc 20

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 40
cctcctcgaa ggtgcagcca 20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
aagtagctga actgcacaca 20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
acaggaagta gctgaactgc 20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
gctgtacagg aagtagctga 20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
cactgacggc cgtgggatcc 20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
ggtgccactg acggccgtgg 20

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
agcctggtgc cactgacggc 20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
agctcagcct ggtgccactg 20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
cagccagctc agcctggtgc 20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
gctgacagcc agctcagcct 20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
gggcctcaaa cagcacctga 20

<210> SEQ ID NO 51
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 51

gatgagggcc tcaaacagca                                                  20


<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52

gagttggtgt tgagctggat                                                  20


<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53

tgatggagtt ggtgttgagc                                                  20


<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54

gccaatgatg gagttggtgt                                                  20


<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55

cccgtcgcca atgatggagt                                                  20


<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56

acagcttgta ggtctgcagg                                                  20


<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57

tggatctcag caaaagccag                                                  20
```

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
gatggtctgg ttgtggctgc 20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
tcttgatggt gtagcggctg 20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
tcctccagtg gagtgaaggt 20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
tcatgtcctc cagtggagtg 20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
tggtagctga tctcatactg 20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
aagctgggag cagagatgtt 20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
gcataatcaa agctgggagc 20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
tgtcggcata atcaaagctg 20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
cggcatgtcg gcataatcaa 20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
ggtgacggca tgtcggcata 20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
aggtctggtt gtcacccacg 20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
tcctccgatc tctgggacac 20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
ccatctcctc cgatctctgg 20

<210> SEQ ID NO 71

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
cctgcacaga tgcccaggat 20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
cggatgatga caatgatggc 20

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
ctttgcggat gatgacaatg 20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
gtggtctctc cctttgcgga 20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
ttctcctggc ggtagttgac 20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
gtgaagctgc ggtccacggc 20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77

-continued cccaggaggc tgctggcctc 20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
aagtggtttg acctgtggta 20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
ctatgaagtg gtttgacctg 20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
agtggctatg aagtggtttg 20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
cccttgagtg gctatgaagt 20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
cagcttggtg atcatgacga 20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
cctctccgct ccagggcaaa 20

<210> SEQ ID NO 84
<211> LENGTH: 20
<212> TYPE: DNA

<213> ORGANISM: Artificial Sequence
<220> FEATURE:
<223> OTHER INFORMATION: Oligomeric Compound

<400> SEQUENCE: 84
tgctctggcc acgctgtgaa 20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
atgggcccgg catcaggtgg 20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
tgacaatggg cccggcatca 20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
agcatcacat ccaggacgat 20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
catgtccagc atcacatcca 20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
gtctccccac acaggcaggc 20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
tggtggtctc cccacacagg 20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
agggatggtg gtctccccac 20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
cgtgtgtagc tgtcagtcag 20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
tgcagggtca cgatgaaggc 20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gtagaccagc cgccagaagt 20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
caggcggagt tggactggtt 20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
tgccacttgt ccacctcagc 20

<210> SEQ ID NO 97
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 97
gttttggcag caaagaaaac 20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
ggtactgatc catggtctcc 20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
agggccccgc tatcttgact 20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
ggttcaggga agctcagagc 20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
gtatgaccag ccctgctcta 20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
atctacagtt tacagatggg 20

<210> SEQ ID NO 103
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
gtcatatcta cagtttacag 20

-continued

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
cagtagtcat atctacagtt 20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
taggtcagta gtcatatcta 20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 106
gcacgtttat ttacaaagcg 20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
caccggcttc cctttgcgga 20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
ctggcagcgt gcaaagagag 20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
gtggtctctc ctggcagcgt 20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound -continued

<400> SEQUENCE: 110
agctacttac gggtagtagg 20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
atttcaaggg aatatttaca 20

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
cctcctcagc acctgggtca 20

<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
cagcaatatc tcctaaagct 20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
ggtgcccctc ctgcaactgg 20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
aggtactcac aggcagtgca 20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
cgcaactgta tgtaccaagc 20

<210> SEQ ID NO 117
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 117
atagcagtcg aacattaatc 20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
tcgttggcat agctgacacc 20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
gagcccgggc catggccgcc 20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
tgggccggcc tcaacagcac 20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
tggccgctct tcctccacaa 20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
gccagggccg tctcaaaggt 20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
ctcaagcagg ctgctggcag 20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
tgggttccag aagccacgat 20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
tcgcttgctc tccttgcacg 20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 126
cttccctttg cggatgatga 20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
tctcgtactc ctgcttgaag 20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
taggcagaca ctggctcctg 20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
cagcgtgatc ttgatgtccc 20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
gtctggatca tgttgacccg 20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
gcgcctgcta tctcaactcc 20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
cagtgtccgt ccgttccagt 20

<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
tggcattcag agagcacatt 20

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
ccttccctga aggttcctcc 20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
tagtgcggac ctacccacga 20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
taaagttgca ggagccagat 20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
acaatgaaca cgtaagtgcc 20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
gcggagcggg actggcgccg 20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
cgggagccca aggcgagcgg 20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
cctaggtcct ggagacccgc 20

<210> SEQ ID NO 145
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 145
gatccgcact tgctcccatt 20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 146
gatgtgggcc ctctgacctg 20

<210> SEQ ID NO 147
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 147
gaagtagctg aactgcacac 20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
aggaagtagc tgaactgcac 20

<210> SEQ ID NO 149
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 149
gtacaggaag tagctgaact 20

<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
tgctgtacag gaagtagctg 20

<210> SEQ ID NO 151
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 151

-continued gtgccactga cggccgtggg 20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
tggtgccact gacggccgtg 20

<210> SEQ ID NO 153
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 153
cctggtgcca ctgacggccg 20

<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
tcagcctggt gccactgacg 20

<210> SEQ ID NO 155
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 155
cagctcagcc tggtgccact 20

<210> SEQ ID NO 156
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 156
gtgctgacag ccagctcagc 20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
ctcaaacagc acctgaaact 20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
gagggcctca aacagcacct 20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
atgagggcct caaacagcac 20

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
agatgagggc ctcaaacagc 20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161
aagcctatgt agcccttgtg 20

<210> SEQ ID NO 162
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
atagctgaag agcaagatgt 20

<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
gacctccacg tccccaaggc 20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
gcattggaag gatgcgttct 20

-continued

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
gaagtgttct gcctctgcgg 20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
caccagcact ccactctgac 20

<210> SEQ ID NO 167
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 167
tgactgatgt gccgcacccc 20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
aaagtggcca ggaagcgacg 20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 169
cctgctctga gcggcctacc 20

<210> SEQ ID NO 170
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 170
ttggagacgc cagcaccacg 20

<210> SEQ ID NO 171
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 171
gggtgggagg ctctttgacg 20

<210> SEQ ID NO 172
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 172
gtgttgagct ggataatgag 20

<210> SEQ ID NO 173
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 173
tggtgttgag ctggataatg 20

<210> SEQ ID NO 174
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 174
tggagttggt gttgagctgg 20

<210> SEQ ID NO 175
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 175
gatggagttg gtgttgagct 20

<210> SEQ ID NO 176
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 176
atgatggagt tggtgttgag 20

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 177
cagatgccac agcttgtagg 20

<210> SEQ ID NO 178

-continued

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 178
agcacgctga tttcatactc 20

<210> SEQ ID NO 179
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 179
gtgcctccat ctcccgggcg 20

<210> SEQ ID NO 180
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 180
agcaaaagcc agacctttgg 20

<210> SEQ ID NO 181
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 181
tagctgatct catactgagt 20

<210> SEQ ID NO 182
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 182
atggtgcgtc tcgggccggg 20

<210> SEQ ID NO 183
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 183
gacgtggtaa gtctcattcc 20

<210> SEQ ID NO 184
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 184
acgtggtgcc gggatgcagg 20

<210> SEQ ID NO 185
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 185
tatctcagtg agagccgcct 20

<210> SEQ ID NO 186
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 186
aaagctggga gctgagatgt 20

<210> SEQ ID NO 187
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 187
gtcggcataa tcaaagctgg 20

<210> SEQ ID NO 188
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 188
atgtcggcat aatcaaagct 20

<210> SEQ ID NO 189
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 189
gcatgtcggc ataatcaaag 20

<210> SEQ ID NO 190
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 190
gacggcatgt cggcataatc 20

<210> SEQ ID NO 191
<211> LENGTH: 20
<212> TYPE: DNA

-continued

<213> ORGANISM: Artificial Sequence
<220> FEATURE:
<223> OTHER INFORMATION: Oligomeric Compound

<400> SEQUENCE: 191
gggtgacggc atgtcggcat 20

<210> SEQ ID NO 192
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 192
tctcaaaggt cagaggtacc 20

<210> SEQ ID NO 193
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 193
gccgtctcaa aggtcagagg 20

<210> SEQ ID NO 194
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 194
gagccagggc cgtctcaaag 20

<210> SEQ ID NO 195
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 195
ccgcgagcca gggccgtctc 20

<210> SEQ ID NO 196
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 196
ggccgcgagc cagggccgtc 20

<210> SEQ ID NO 197
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 197
caggccgcga gccagggccg 20

<210> SEQ ID NO 198
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 198
agttcagccc caaagtagtg 20

<210> SEQ ID NO 199
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 199
catggcctca agcaggctgc 20

<210> SEQ ID NO 200
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 200
aggtctggtt gtcacccacg 20

<210> SEQ ID NO 201
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 201
ggaaatagat gagataggcc 20

<210> SEQ ID NO 202
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 202
ttcccctttc aggtggcttg 20

<210> SEQ ID NO 203
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 203
tggcaattcg gatgcagttc 20

<210> SEQ ID NO 204
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 204
cttgctctcc ttgcacgcag 20

<210> SEQ ID NO 205
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 205
tgagccccat ctcctccgat 20

<210> SEQ ID NO 206
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 206
gcaagaccac ctgcacagat 20

<210> SEQ ID NO 207
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 207
atggccccca ggaggagaat 20

<210> SEQ ID NO 208
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 208
actggcttcc ctttgcggat 20

<210> SEQ ID NO 209
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 209
ggtagttgac cgtggctttc 20

<210> SEQ ID NO 210
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 210
gcactcatca tgtgagtctt 20

<210> SEQ ID NO 211
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 211
gtactctgat ctgtgaagct 20

<210> SEQ ID NO 212
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 212
gacagaccca accgctcatc 20

<210> SEQ ID NO 213
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 213
cggtgacacc accgcttcgc 20

<210> SEQ ID NO 214
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 214
ttggagaacc ccccaggagg 20

<210> SEQ ID NO 215
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 215
atacggagaa cccttccggc 20

<210> SEQ ID NO 216
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 216
ggtctcccca cacaggcagg 20

<210> SEQ ID NO 217
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 217
aactcgttga cagggatggt 20

<210> SEQ ID NO 218
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 218
gatcatctcc ctgtaggtgg 20

<210> SEQ ID NO 219
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 219
tctggaactc ttcccgaagc 20

<210> SEQ ID NO 220
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 220
cagcagggca atgctacact 20

<210> SEQ ID NO 221
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 221
gctgcattga tgtagttatt 20

<210> SEQ ID NO 222
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 222
ctccggccag tactgcaagc 20

<210> SEQ ID NO 223
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 223
catgagccca tactgctgtc 20

<210> SEQ ID NO 224
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 224
ttgctgtgcc agacacaaac 20

<210> SEQ ID NO 225
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 225
tcctgcagcc gagaagagtt 20

<210> SEQ ID NO 226
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 226
cgtgtcccga taagcagacc 20

<210> SEQ ID NO 227
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 227
gtgcagaaag gccttcctgg 20

<210> SEQ ID NO 228
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 228
tctgcacagg tctgcagggc 20

<210> SEQ ID NO 229
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 229
actagctatt ttggtccagg 20

<210> SEQ ID NO 230
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 230
ggccaaggac tgtgatggag 20

<210> SEQ ID NO 231
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 231
ggtgctctct gcagacactc 20

<210> SEQ ID NO 232
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 232
cagaaaggac catactgggt 20

<210> SEQ ID NO 233
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 233
ctgccaagtc ccagtgagcc 20

<210> SEQ ID NO 234
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 234
gcaaagcacc ccaggtctgt 20

<210> SEQ ID NO 235
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 235
gcaggaaaag ctcagaagca 20

<210> SEQ ID NO 236
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 236
gggatggagc ccaggaagga 20

<210> SEQ ID NO 237
<211> LENGTH: 20
<212> TYPE: DNA
<213> ORGANISM: Artificial Sequence -continued
<220> FEATURE:
<223> OTHER INFORMATION: Oligomeric Compound

<400> SEQUENCE: 237
agctgaagta tatcattctg 20

<210> SEQ ID NO 238
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 238
ccaagctgag caggactgaa 20

<210> SEQ ID NO 239
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 239
cagccttgtg gattgtcaca 20

<210> SEQ ID NO 240
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 240
ggctgtgatt cagccttgtg 20

<210> SEQ ID NO 241
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 241
cagcctcacc aagagccaca 20

<210> SEQ ID NO 242
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 242
ccccgatcca gtggcagcct 20

<210> SEQ ID NO 243
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 243
caccagccct gttctagcct 20

-continued

<210> SEQ ID NO 244
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 244
tactctagga gctgacacca 20

<210> SEQ ID NO 245
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 245
gtatcccttc ttcctctgta 20

<210> SEQ ID NO 246
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 246
gtcctccatt ccaaagtatc 20

<210> SEQ ID NO 247
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 247
caaaaaaagc actggtcctc 20

<210> SEQ ID NO 248
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 248
aataacaaaa taacaacaac 20

<210> SEQ ID NO 249
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 249
catcaaaaaa ataacaaaat 20

<210> SEQ ID NO 250
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 250
aagagaactt cccaccctcc 20

<210> SEQ ID NO 251
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 251
ttataaagag aacttcccac 20

<210> SEQ ID NO 252
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 252
tcatatctac agtttacaga 20

<210> SEQ ID NO 253
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 253
acagccccct gtgaggtagg 20

<210> SEQ ID NO 254
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 254
tacaaacatt accttacacc 20

<210> SEQ ID NO 255
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 255
tcagagagca catttattta 20

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
ggcacagcaa acgaggattt 20

<210> SEQ ID NO 257

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 257

gcagaccaac gcagaaactg                                                20


<210> SEQ ID NO 258
<211> LENGTH: 17
<212> TYPE: DNA
<213> ORGANISM: Artificial Sequence
<220> FEATURE:
<223> OTHER INFORMATION: Probe

<400> SEQUENCE: 258

tcccgagtgt tccgggt                                                   17
```

COMPOSITIONS AND THEIR USES DIRECTED TO PTPRU

RELATED APPLICATIONS

This application is a U.S. National Phase under 35 U.S.C. §371 of PCT/US2006/020388, filed May 24, 2006, designating the United States and published in English on Nov. 30, 2006 as WO2006/127976, which claims the benefit of priority of U.S. Provisional Patent Application No. 60/684,398, filed May 24, 2005. The content of these applications is incorporated herein by reference in their entireties.

FIELD OF THE INVENTION

Disclosed herein are compounds, compositions and methods for modulating the expression of PTPRU in a cell, tissue or animal.

BACKGROUND OF THE INVENTION

Phosphorylation and dephosphorylation are ubiquitous processes within cells that greatly influence cellular phenotypes. The extent and duration of phosphorylation is regulated by the opposing action of phosphatases, which remove the phosphate moieties. Consequently, considerable attention has been devoted to the characterization of tyrosine kinases and tyrosine phosphatases and their associations with disease states (Zhang, *Crit. Rev. Biochem. Mol. Biol.,* 1998, 33, 1-52).

Protein tyrosine phosphatases are signaling molecules that regulate a variety of cellular processes, including cell growth and differentiation, cell cycle progression and growth factor signaling. A number of protein tyrosine phosphatases have been implicated as negative regulators of insulin signaling (Zhang, *Crit. Rev. Biochem. Mol. Biol.,* 1998, 33, 1-52). Characterization of the protein tyrosine phosphatase PTPRU revealed it to be a member of the type II receptor protein tyrosine phosphatase (rPTP) subfamily, which includes PTP.mu. and PTP.kappa. PTPRU contains many of the domains characteristic of this subfamily, including a transmembrane domain and two tandem intracellular protein tyrosine phophatase domains. In addition, the presence of the extracellular immunoglobulin (Ig) domain and four tandem fibronectin-type III (FN-III) repeats, which are common to cell-adhesion receptors, suggests that PTPRU can contribute to the mechanisms of cell adhesion and homotypic cell interactions (Avraham et al., *Gene,* 1997, 204, 5-16; Crossland et al., *Biochem. J.,* 1996, 319 (Pt 1), 249-254; Thomas et al., *J. Biol. Chem.,* 1994, 269, 19953-19962; Wang et al., *Biochem. Biophys. Res. Commun.,* 1997, 231, 77-81; Wang et al., *Oncogene,* 1996, 12, 2555-2562). PRPRU also contains a MAM domain, which, along with the Ig-like domain, is required for the homophilic interactions displayed by PTP.mu. and PTP-.kappa. (Avraham et al., *Gene,* 1997, 204, 5-16; Crossland et al., *Biochem. J.,* 1996, 319 (Pt 1), 249-254; Wang et al., *Biochern. Biophys. Res. Commun.,* 1997, 231, 77-81; Wang et al., *Oncogene,* 1996, 12, 2555-2562).

Owing to its simultaneous identification in several different cell types, PTPRU is known by many synonyms, including protein tyrosine phosphatase, receptor type, U, also known as PTP-RU or PTPU2; protein tyrosine phosphatase receptor omicron or PTPRO; protein tyrosine phosphatase pi; protein tyrosine phosphatase J or PTP-J; pancreatic carcinoma phosphatase 2, PCP2 or PCP-2; protein tyrosine phosphatase psi, receptor type, R-PTP-Psi, PTPPsi or pi R-PTP-Psi; glomerular epithelial protein 1 or GLEPP1; and FMI.

The expression of PTPRU is developmentally regulated. During early development expression is mainly in the brain and lung. In adults, PTPRU expression is in the kidney, lung, heart, skeletal muscle, pancreas, liver, prostate, testis, brain, bone marrow, and stem cells (Avraham et al., *Gene,* 1997, 204, 5-16; Crossland et al., *Biochem. J.,* 1996, 319 (Pt 1), 249-254; Wharram et al., *J. Clin. Invest.,* 2000, 106, 1281-1290; Beltran et al., *J. Comp. Neurol.,* 2003, 456, 384-395; Stepanek et al., *J. Cell Biol.,* 2001, 154, 867-878). PTPRU is additionally involved with megakaryopoiesis, cell adhesion and promotion of the G0/G1 cell cycle arrest in normal naïve quiescent B cells (Taniguchi et al., *Blood,* 1999, 94, 539-549; Aguiar et al., *Blood,* 1999, 94, 2403-2413; Yan et al., *Biochemistry,* 2002, 41, 15854-15860).

A number of tissue-specific forms of PTPRU have been identified. In the kidney, PTPRU is known as GLEPP1 and is highly expressed in podocytes, specialized epithelial cells that form the glomerular capillaries (Thomas et al., *J. Biol. Chem.,* 1994, 269, 19953-19962). In megakaryocytes, PTPRU is called PTPRO, alternative splicing of which yields a lymphoid tissue-specific, truncated form called PTPROt (Aguiar et al., *Blood,* 1999, 94, 2403-2413). Alternative splicing of PTPRU also yields osteoclastic protein tyrosine phosphatase or PTP-oc (Amoui et al., *J. Biol. Chem.,* 2003, 278, 44273-44280).

In addition to participation in the regulation of several essential functions, PTPRU is implicated in numerous disease conditions. Motiwala et al., have reported a correlation between PTPRU and diet dependent development of preneoplastic nodules and hepatocellular carcinoma (Motiwala et al., *Oncogene,* 2003, 22, 6319-6331). PTPRU expression was found to be altered in several cancerous cell lines (Crossland et al., *Biochem. J.,* 1996, 319 (Pt 1), 249-254; McArdle et al., *J. Invest. Dermatol.,* 2001, 117, 1255-1260; Wang et al., *Biochem. Biophys. Res. Commun.,* 1997, 231, 77-81; Wang et al., *Biochem. Biophys. Acta.,* 1999, 1450, 331-340). Furthermore, PTPRU was found to be hypermethylated in colon cancer (Mori et al., *Cancer Res.,* 2004, 64, 2434-2438).

The diverse tissue distribution and disease associations of PTPRU indicate that it can be an appropriate target for therapeutic intervention in a number of disease conditions.

Currently, there are no known therapeutic agents that effectively inhibit the synthesis and/or function of PTPRU. Consequently, there remains a long felt need for agents capable of effectively inhibiting PTPRU synthesis and/or function.

Generally, the principle behind antisense technology is that an antisense compound hybridizes to a target nucleic acid and effects the modulation of gene expression activity, or function, such as transcription or translation. The modulation of gene expression can be achieved by, for example, target RNA degradation or occupancy-based inhibition. An example of modulation of target RNA function by degradation is RNase H-based degradation of the target RNA upon hybridization with a DNA-like antisense compound. Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. This sequence-specificity makes antisense compounds extremely attractive as tools for target validation and gene functionalization, as well as therapeutics to selectively modulate the expression of genes involved in diseases.

SUMMARY OF THE INVENTION

Disclosed herein is the discovery PTPRU can be modulated to effect in vivo glucose levels. This newly discovered correlation between PTPRU activity and in vivo glucose levels provides a novel pathway for regulating glucose homeostasis in an animal. In one embodiment, modulators that decrease the activity of PTPRU are provided as compounds that reduce in vivo glucose levels. Preferrably the PTPRU modulators are specific for PTPRU, and more preferably the modulators are antisense compounds that hybridize with a nucleic acid molecule that expresses PTPRU, thereby inhibiting expression of the nucleic acid molecule. In another embodiment, the glucose levels are blood glucose levels, which include, but are not limited to, whole blood, plasma or serum glucose levels. In a further embodiment, the in vivo blood glucose levels are reduced to treat a disease or condition associated therewith. The disease or condition can include, but is not limited to, diabetes, type II diabetes, prediabetes, obesity, metabolic syndrome or a combination thereof.

In a further aspect, PTPRU is modulated to effect the levels of HbA.sub.1c (hereinafter "HbA1c"). HbA1c is a glycosylated form of hemoglobin and is a clinical indicator of excessive blood glucose levels and diabetes. In one embodiment, modulators of PTPRU are provided as compounds that that reduce in vivo blood glucose levels and in turn reduce the levels of HbA1c. Preferably, the PTPRU modulators are specific for PTPRU, and more preferably the modulators are antisense compounds that hybridize with a nucleic acid molecule that expresses PTPRU, thereby inhibiting expression of the nucleic acid molecule.

Disclosed herein are antisense compounds targeted to and hybridizable with a nucleic acid molecule encoding PTPRU and which modulate the expression of PTPRU. In a preferred embodiment the nucleic acid molecule encoding PTPRU has a nucleotide sequence that is substantially similar to one or more of GenBank Accession Nos.: NM_005704.2, NM_133177.1, NM_133178.1 or NT_004538.15 (SEQ ID NOS: 1-4, respectively), presented in table 1, below and incorporated herein by reference. In a further aspect, the antisense compounds are targeted to and hybridizable with a region of a nucleic acid molecule encoding PTPRU. Still further, the antisense compounds are targeted to and hybridizable with a segment of a nucleic acid molecule encoding PTPRU. Still further the antisense compounds are targeted to and hybridizable with a site of a nucleic acid molecule encoding PTPRU.

Further disclosed herein are active target segments comprising segments of a nucleic acid molecule encoding PTPRU, the active target segments being accessible to antisense hybridization, and so, suitable for antisense modulation. In one embodiment, the active target segments have been discovered herein using empirical data that is presented below, wherein at least two chimeric oligonucleotides are shown to hybridize within the active target segment and reduce expression of the target nucleic acid (hereinafter, "active antisense compound"). The at least two active antisense compounds are preferably separated by about 60 nucleobases on the nucleic acid molecule encoding PTPRU. In another embodiment, antisense compounds are designed to target the active target segments and modulate expression of the nucleic acid molecule encoding PTPRU.

In one aspect there are herein provided antisense compounds comprising sequences 12 to 35 nucleotides in length comprising at least two chemical modifications selected from a modified internucleoside linkage, a modified nucleobase or a modified sugar. Provided herein are chimeric oligonucleotides comprising a deoxynucleotide mid-region flanked on each of the 5' and 3' ends by wing regions, each wing region comprising at least one high affinity nucleotide.

In one embodiment there is herein provided chimeric oligonucleotides comprising ten deoxynucleotide mid-regions flanked on each of the 5' and 3' ends with wing regions comprising five 2'-O-(2-methoxyethyl) nucleotides and wherein each internucleoside linkage of the chimeric oligonucleotide is a phosphorothioate. In another embodiment there is herein provided chimeric oligonucleotides comprising fourteen deoxynucleotide mid-regions flanked on each of the 5' and 3' ends with wing regions comprising three locked nucleic acid nucleotides and wherein each internucleoside linkage of the chimeric oligonucleotide is a phosphorothioate. In a further embodiment there are hererin provided chimeric oligonucleotides comprising fourteen deoxynucleotide mid-regions flanked on each of the 5' and 3' ends by wing regions comprising two 2'-O-(2-methoxyethyl) nucleotides and wherein each internucleoside linkage of the chimeric oligonucleotide is a phosphorothioate. In a further embodiment, the antisense compounds may comprise at least one 5-methylcytosine.

Further provided herein are methods of modulating the expression of PTPRU in cells, tissues or animals comprising contacting the cells, tissues or animals with one or more of the antisense compounds. In one embodiment, the antisense compounds are contacted to the cell, tissue or animal and inhibiting the expression of PTPRU therein. The inhibition of PTPRU expression can be measured by analyzing the cells for indicators of a decrease in expression of PTPRU mRNA and/or protein by direct measurement of mRNA and/or protein levels, and/or measuring glucose levels, triglyceride levels, insulin levels, fatty acid levels, cholesterol levels, transaminase levels, electrocardiogram, glucose uptake, gloconeogenesis, insulin sensitivity and body weight In one embodiment, there are provided methods of lowering plasma glucose or plasma triglycerides using antisense compounds that inhibit PTPRU expression in cells, tissues or animals. In another embodiment, there are provided methods of improving insulin sensitivity using antisense compounds that inhibit PTPRU expression in cells, tissues or animals.

In other embodiments, the there are provided methods of ameliorating or lessening the severity of a condition in an animal comprising contacting said animal with an effective amount of an oligomeric compound that inhibits PTPRU expression in cells, tissues or animals. In an additional embodiment, the ameliorating or lessening of the severity of the condition of an animal is measured by one or more physical indicators of said condition, comprising glucose levels, triglyceride levels, insulin levels, fatty acid levels, cholesterol levels, transaminase levels, electrocardiogram, glucose uptake, gluconeogenesis, insulin sensitivity and body weight. The conditions include, but are not limited to, diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease.

Also provided is a method of use of the oligomeric compound of the instant invention for the preparation of a medicament for the prevention, amelioration, and/or treatment disease, especially a disease associated with and including at least one indicator comprising glucose levels, triglyceride levels, insulin levels, fatty acid levels, cholesterol levels, transaminase levels, electrocardiogram, glucose uptake, gloconeogenesis, insulin sensitivity and body weight.

DETAILED DESCRIPTION OF THE INVENTION

PTPRU is herein shown to effect in vivo glucose levels in mammals. This novel discovery, therefore, provides PTPRU as a novel target for modulating blood glucose levels. Provided herein are methods of modulating blood glucose levels using a modulator of PTPRU. Preferrably the modulator is selective for PTPRU. Also preferably the modulator is an antisense compound that hybridizes with a nucleic acid molecule that expreses PTPRU, thereby inhibiting the expression of the nucleic acid molecule. In one aspect, the methods of modulating PTPRU are useful for treating a disease or condition associated thererwith, the disease or condition including, but not being limited to, diabetes, type II diabetes, prediabetes, obesity, metabolic syndrome or a combination thereof.

Also provided herein are modulators that decrease the activity of PTPRU and in turn reduce in vivo glucose levels. Preferrably the PTPRU modulators are specific for PTPRU, and more preferably the modulators are antisense compounds that hybridize with a nucleic acid molecule that expresses PTPRU, thereby inhibiting expression of the nucleic acid molecule. In another embodiment, the glucose levels are blood glucose levels, which include, but are not limited to, whole blood, plasma or serum glucose levels. In a further embodiment, the in vivo blood glucose levels are reduced to treat a disease or condition associated therewith. The disease or condition can include, but is not limited to, diabetes, type II diabetes, prediabetes, obesity, metabolic syndrome or a combination thereof.

In a further aspect, PTPRU is modulated to effect the levels of HbA.sub.1c (hereinafter "HbA1c"). HbA1c is a glycosylated form of hemoglobin and is a clinical indicator of excessive blood glucose levels and diabetes. In one embodiment, modulators of PTPRU are provided as compounds that that reduce in vivo blood glucose levels and in turn reduce the levels of HbA1c. Preferably, the PTPRU modulators are specific for PTPRU, and more preferably the modulators are antisense compounds that hybridize with a nucleic acid molecule that expresses PTPRU, thereby inhibiting expression of the nucleic acid molecule.

Moreover, PTPRU has been shown to effect triglyceride levels, insulin levels, fatty acid levels, cholesterol levels, transaminase levels, glucose uptake, gloconeogenesis and insulin sensitivity. Therefore, PTPRU is indicated in diseases and conditions related thereto and including, but not limited to, diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease. The instant invention provides antisense compounds for the prevention, amelioration, and/or treatment of diseases and conditions relating to PTPRU function. As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators may be determined by subjective or objective measures which are known to those skilled in the art. As used herein, "treatment" means to administer a composition of the invention to effect an alteration or improvement of the disease or condition. Prevention, amelioration, and/or treatment may require administration of single dose or of multiple doses at regular intervals to alter the course of the condition or disease.

Disclosed herein are antisense compounds, including antisense oligonucleotides and other antisense compounds for use in modulating the expression of nucleic acid molecules encoding PTPRU. This is accomplished by providing antisense compounds that hybridize with one or more target nucleic acid molecules encoding PTPRU. As used herein, the terms "target nucleic acid" and "nucleic acid molecule encoding PTPRU" have been used for convenience to encompass RNA (including pre-mRNA and mRNA or portions thereof) transcribed from DNA encoding PTPRU, and also cDNA derived from such RNA. In a preferred embodiment, the target nucleic acid is an mRNA encoding PTPRU.

Target Nucleic Acids

"Targeting" an antisense compound to a particular target nucleic acid molecule can be a multistep process. The process usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes PTPRU and has a polynucleotide sequence that is substantially similar to one or more of SEQ ID NOS: 1-4.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Antisense compounds targeted to such variants are within the scope of the instant invention.

In accordance with the present invention are compositions and methods for modulating the expression of PTPRU. Table 1 lists the GenBank accession numbers of sequences corresponding to nucleic acid molecules encoding PTPRU (nt=nucleotide), the date the version of the sequence was entered in GenBank, and the corresponding SEQ ID NO in the instant application, when assigned, each of which is incorporated herein by reference.

TABLE 1

Gene Targets

| Species | Genbank # | Genbank Date | SEQ ID NO |
|---|---|---|---|
| Human | NM_005704.2 | Mar. 26, 2002 | 1 |
| Human | NM_133177.1 | Mar. 26, 2002 | 2 |
| Human | NM_133178.1 | Mar. 26, 2002 | 3 |
| Human | nucleotides 751930 to 843018 of NT_004538.15 (replaced by NT_004610) | Oct. 7, 2003 | 4 |
| Mouse | U55057.1 | Nov. 1, 1996 | 5 |

Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is L 0 converted into structures present and operating in a cell. These structures include the products of transcription and translation. "Modulation of expression" means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of PTPRU. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of antisense compounds of the present invention on target nucleic acid expression can be tested in any of a variety of cell types provided that the target nucleic acid is present at measurable levels. The effect of antisense compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources, and are well known to those skilled in the art. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). Primary cells prepared by methods known in the art.

Assaying Modulation of Expression

Modulation of PTPRU expression can be assayed in a variety of ways known in the art. PTPRU mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by PTPRU can be quantitated in a variety of ways well known in the art, such as immunoprecipitation, Western blot analysis (immunoblotting), ELISA or fluorescence-activated cell sorting (FACS). Antibodies directed to a protein encoded by PTPRU can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of Monoclonal Antibodies is Taught in, for Example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997.

Active Target Segments

The locations on the target nucleic acid defined by having at least two active antisense compounds targeted thereto are referred to as "active target segments." An active target segment is defined by one of the at least two active antisense compounds hybridizing at the 5' end of the active target segment and the other hybridizing at the 3' end of the active target segment. Additional active antisense compounds may hybridize within this defined active target segment. The compounds are preferably separated by no more than about 60 nucleotides on the target sequence, more preferably no more than about 30 nucleotides on the target sequence, even more preferably the compounds are contiguous, most preferably the compounds are overlapping. There may be substantial variation in activity (e.g., as defined by percent inhibition) of the antisense compounds within an active target segment. Active antisense compounds are those that modulate the expression of their target RNA. In one of the assays provided herein, active antisense compounds inhibit expression of their target RNA at least 10%, preferably 20%. In a preferred embodiment, at least about 50%, preferably about 70% of the oligonucleotides targeted to the active target segment modulate expression of their target RNA at least 40%. In a more preferred embodiment, the level of inhibition required to define an active antisense compound is defined based on the results from the screen used to define the active target segments. One ordinarily skilled in the art will readily understand that values received from any single assay will vary in comparison to other similar assays due to assay-to-assay conditions.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural base 5-methyl cytosine and the artificial base kiniown as a G-clamp. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid.

Those in the art understand that for an antisense compound to be active it need not be 100% complementary to the target nucleic acid site wherein it hybridizes. Often, once an antisense compound has been identified as an active antisense compound, the compounds are routeinly modified to include mismatched nucleobases compared to the sequence of the target nucleic acid site. The art teaches methods for introducing mismatches into an antisense compound without substantially altering its activity. Antisense compounds may be able to tolerate up to about 20% mismatches without significant alteration of activity, particularly so when a high affinity modification accompanies the mismatches.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least 70%, or at least 75%, or at least 80%, or at least 85%, or at least 90%, or at least 92%, or at least 95%, or at least 97%, or at least 98%, or at least 99% sequence complementarity to a target region within the target nucleic acid sequence to which they are targeted. For example, an oligomeric compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mal. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Identity

Antisense compounds, or a portion thereof, may have a defined percent identity to a SEQ ID NO, or a compound having a specific compound number. As used herein, a sequence is identical to the sequence disclosed herein if it has the same nucleobase pairing ability. For example, a RNA which contains uracil in place of thymidine in the disclosed sequences of the instant invention would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the invention. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the invention, the complement of an active target segment may constitute a single portion. In a preferred embodiment, the oligonucleotides of the instant invention are at least about 80%, more preferably at least about 85%, even more preferably at least about 90%, most prefereably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA in an oocyte injection model. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358, 1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs.

Therapeutics

Modulators of PTPRU, more preferably selective modulators of PTPRU and more preferably still antisense compounds can be used to modulate the expression of PTPRU in an animal, such as a human. Modulation of PTPRU is herein disclosed as resulting in a corresponding modulation in glucose levels, therefore there are provided compositions and methods for treating conditions and disorders associated with blood glucose levels. In one non-limiting embodiment, the methods comprise the step of administering to said animal in need of therapy for a disease or condition associated with PTPRU an effective amount of an antisense compound that inhibits expression of PTPRU. A disease or condition associated with PTPRU includes, but is not limited to, diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease. The diseases or conditions are associated with clinical indicators that include, but are not limited to blood glucose levels, blood lipid levels, hepatic lipid levels, insulin levels, cholesterol levels, transaminase levels, electrocardiogram, glucose uptake, gluconeogenesis, insulin sensitivity, body weight and combinations thereof. In one embodiment, the antisense compounds of the present invention effectively inhibit the levels or function of PTPRU mRNA. Because reduction in PTPRU mRNA levels can lead to alteration in PTPRU protein products of expression as well, such resultant alterations can also be measured. Antisense compounds of the present invention that effectively inhibit the level or function of PTPRU mRNA or protein products of expression are considered an active antisense compounds. In one embodiment, the antisense compounds of the invention inhibit the expression of PTPRU causing a reduction of RNA by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of PTPRU can be measured in a bodily fluid, tissue or organ of the animal. Methods of obtaining samples for analysis, such as body fluids (e.g., blood), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the PTPRU expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; glucose levels, triglyceride levels, insulin levels, fatty acid levels, cholesterol levels, electrocardiogram, glucose uptake, gloconeogenesis, insulin sensitivity and body weight, and other markers of diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease. Additionally, the effects of reatment can be assessed using non-invasive indicators of improved disease state or condition, such as electrocardiogram, body weight, and the like.

The antisense compounds of the present invention can be utilized in pharmaceutical compositions by adding an effective amount of a compound to a suitable pharmaceutically acceptable diluent or carrier. Acceptable carriers and dilutents are well known to those skilled in the art. Selection of a dilutent or carrier is based on a number of factors, including, but not limited to, the solubility of the compound and the route of administration. Such considerations are well understood by those skilled in the art. In one aspect, the compounds of the present invention inhibit the expression of PTPRU. The compounds of the invention can also be used in the manufacture of a medicament for the treatment of diseases and disorders related to PTPRU expression by restoring glucose levels, triglyceride levels, insulin levels, fatty acid levels, cholesterol levels, glucose uptake, gloconeogenesis and insulin sensitivity to non-diesase state profiles. Moreover, the compounds of the invention can be used in the manufacture of a medicament for the modulation of blood glucose levels. In this aspect, the compound is preferably a modulator that is specific for PTPRU, and is more preferably an antisense compound that inhibits the expression of a nucleic acid that encodes PTPRU. Also in this aspect, the medicament is used to modulate blood glucose levels and treat diseases and conditions associated therewit. Disease and conditions associated with dysregulated blood glucose levels include, but are not limited to, diabetes, type II diabetes, prediabetes, obesity, metabolic syndrome or a combination thereof.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of PTPRU expression in the cells of bodily fluids, organs or tissues.

Kits, Research Reagents, and Diagnostics

The antisense compounds of the present invention can be utilized for diagnostics, and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the antisense compounds of the present invention, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Antisense Compounds

The term "antisense compound" refers to a polymeric structure capable of hybridizing to a region of a nucleic acid molecule. As is also used herein, the term "active antisense compound" is an antisense compound that has been determined to hybridize with the target nucleic acid and modulate its expression. Generally, antisense compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar, includes a nucleobase, modified nucleobase or a nucleobase mimetic. Preferred monomeric subunits comprise nucleosides and modified nucleosides. An antisense compound is at least partially complementary to the region of a target nucleic acid molecule to which it hybridizes and which modulates (increases or decreases) its expression. This term includes oligonucleotides, oligonucleosides, oligonucleotide analogs, oligonucleotide inimetics, antisense compounds, antisense oligomeric compounds, and chimeric combinations of these. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. In some embodiments it is desirous to take advantage of alternate antisense mechanisms (such as RNAi). Antisense compounds that use these alternate mechanisms may optionally comprise a second compound which is complementary to the antisense compound. In other words, antisense double-stranded compounds can be two strands hybridized to form double-stranded compounds or a single strand with sufficient self complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang Each strand of the siRNA duplex may be from about 12 to about 35 nucleobases. In a preferred embodiment, each strand of the siRNA duplex is about 17 to about 25 nucleobases. The two strands may be fully complementary (i.e., form a blunt ended compound), or include a 5' or 3' overhang on one or both strands. Double-stranded compounds can be made to include chemical modifications as discussed herein.

In one embodiment of the invention, the antisense compound comprises a single stranded oligonucleotide. In some embodiments of the invention the antisense compound contains chemical modifications. In a preferred embodiment, the antisense compound is a single stranded, chimeric oligonucleotide wherein the modifications of sugars, bases, and internucleoside linkages are independently selected.

The antisense compounds may comprise a length from about 12 to about 35 nucleobases (i.e. from about 12 to about 35 linked nucleosides). In other words, a single-stranded compound of the invention comprises from about 12 to about 35 nucleobases, and a double-stranded antisense compound of the invention (such as a siRNA, for example) comprises two strands, each of which is independently from about 12 to about 35 nucleobases. This includes oligonucleotides 15 to 35 and 16 to 35 nucleobases in length. Contained within the antisense compounds of the invention (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases. For convenience we describe antisense compounds, but one ordinarily skilled in the art will understand that analogues and mimetics can have a length within this same range.

The oligomeric compounds in accordance with this invention may comprise a complementary oligomeric compound from about 13 to about 80 nucleobases (i.e. from about 13 to about 80 linked nucleosides). In other words, a single-stranded compound of the invention comprises from 13 to about 80 nucleobases, and a double-stranded antisense compound of the invention (such as a siRNA, for example) comprises two strands, each of which is from about 13 to about 80 nucleobases. Contained within the oligomeric compounds of the invention (whether single or double stranded and on at least one strand) are antisense portions. The "antisense portion" is that part of the oligomeric compound that is designed to work by an antisense mechanism. One of ordinary skill in the art will appreciate that this comprehends antisense portions of 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases. In one embodiment, the oligomeric compounds of the invention have antisense portions of 13 to 50 nucleobases. One having ordinary skill in the art will appreciate that this embodies oligomeric compounds having antisense portions of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases. In one embodiment, the oligomeric compounds of the invention have antisense portions of 13 to 30 nucleobases. One having ordinary skill in the art will appreciate that this embodies oligomeric compounds having antisense portions of 13, 14, 15, 16, 17, 18, 19, 20, 21, 22, 23, 24, 25, 26, 27, 28, 29 or 30 nucleobases. In some embodiments, the oligomeric compounds of the invention have antisense portions of 13 to 24 nucleobases. One having ordinary skill in the art will appreciate that this embodies oligomeric compounds having antisense portions of 13, 14, 15, 16, 17, 18, 19, 20, 21, 22, 23 or 24 nucleobases.

Antisense compounds about 12 to 35 nucleobases in length, preferably about 15 to 35 nucleobases in length, comprising a stretch of at least eight (8), preferably at least 12, more preferably at least 15 consecutive nucleobases selected from within the active target regions are considered to be suitable antisense compounds as well.

Modifications can be made to the antisense compounds of the instant invention and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-Methoxy ethoxy (2'-MOE) sugar modifications, inverted abasic caps, deoxynucleobases, and bicyclice nucleobase analogs such as locked nucleic acids (LNA.sup.TM) and ENA.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the present invention. The terms modified nucleobase and nucleobase mimetic can overlap but generally a modified nucleobase refers to a nucleobase that is fairly similar in structure to the parent nucleobase, such as for example a 7-deaza purine or a 5-methyl cytosine, whereas a nucleobase mimetic would include more complicated structures, such as for example a tricyclic phenoxazine nucleobase mimetic. Methods for preparation of the above noted modified nucleobases are well known to those skilled in the art.

Antisense compounds may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-$(CH_2)_2$—O-2' bridge); and substituted sugars, especially 2'-substituted sugars having a 2'-F, 2'-$OCH_2$ or a 2'-O$(CH_2)_2$—$OCH_3$ substituent group. Sugars can also be replaced with sugar mimetic groups among others. Methods for the preparations of modified sugars are well known to those skilled in the art.

Internucleoside linking groups link the nucleosides or otherwise modified monomer units together thereby forming an antisense compound. The two main classes of internucleoside lnking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH.sub.2-N(CH.sub.3)-O—CH.sub.2-), thiodiester (—O—C(O)—S—), thionocarbamate (—O—C(O)(NH)—S—); siloxane (—O—Si(H).sub.2-O—); and N,N'-dimethylhydrazine (—CH.sub.2-N(CH.sub.3)-N(CH.sub.3)-). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this disclosure, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

Provided are compounds having reactive phosphorus groups useful for forming internucleoside linkages including for example phosphodiester and phosphorothioate internucleoside linkages. Methods of preparation and/or purification of precursors or antisense compounds of the instant invention are not a limitation of the compositions or methods of the invention. Methods for synthesis and purification of DNA, RNA, and the antisense compounds are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound.

Chimeric antisense compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter antisense compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric antisense compounds can be further described as having a particular motif. As used herein, the term "motif" refers to the orientation of modified sugar moieties and/or sugar mimetic groups in an antisense compound relative to like or differentially modified or unmodified nucleosides. As used herein, the terms "sugars", "sugar moieties" and "sugar mimetic groups' are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used herein, the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings.

As used herein, the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used herein, the term "fully modified motif" refers to an antisense compound comprising a contiguous sequence of nucleosides wherein essentially each nucleoside is a sugar modified nucleoside having uniform modification.

As used herein, the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used herein, the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. Methods of preparation of chimeric oligonucleotide compounds are well known to those skilled in the art.

As used herein, the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), alpha. or beta., or as (D) or (L) such as for amino acids et al. This is meant to include all such possible isomers, as well as their racemic and optically pure forms.

In one aspect, antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The compositions and methods disclosed herein not limited by the method of oligomer purification.

Salts, Prodrugs and Bioequivalents

The antisense compounds may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term “prodrug” indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., phosphodiester backbone linkages) to produce the smaller active compound.

The term “pharmaceutically acceptable salts” refers to physiologically and pharmaceutically acceptable salts of the antisense compounds: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds may also be admixed, encapsulated, conjugated or otherwise associated with other molecules, molecule structures or mixtures of compounds.

The antisense compounds may also include pharmaceutical compositions and formulations. The pharmaceutical compositions of the present invention may be administered in a number of ways depending upon whether local or systemic treatment is desired and upon the area to be treated.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery).

A “pharmaceutical carrier” or “excipient” can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions provided herein can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions can contain two or more antisense compounds targeted to different regions of the same nucleic acid target. Two or more combined compounds may be used together or sequentially. Compositions of the instant invention can also be combined with other non-antisense compound therapeutic agents.

Nonlimiting Disclosure and Incorporation by Reference

While certain compounds, compositions and methods have been described with specificity in accordance with certain embodiments, the following examples serve only as illustrations of the compounds and methods and are not intended to limit the claims of the invention. Each of the references, GenBank accession numbers, and the like recited in the present application is incorporated herein by reference in its entirety.

EXAMPLE 1

Cell Types and Transfection Methods

Cell types—The effect of antisense compounds on target nucleic acid expression was tested in one or more of the following cell types.

A549: The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsimization and dilution when they reached approximately 90% confluence. Cells were seeded into 96-well plates (Falcon-Primaria #3872) at a density of approximately 5000 cells/well for use in oligomeric compound transfection experiments.

B16-F10: The mouse melanoma cell line B16-F10 was obtained from the American Type Culture Collection (Manassas, Va.). B16-F10 cells were routinely cultured in DMEM, high glucose (Invitrogen Life Technologies, Carlsbad, Calif.) supplemented with 10% fetal bovine serum (Invitrogen Life Technologies, Carlsbad, Calif.), Cells were routinely passaged by trypsinization and dilution when they reached approximately 90% confluence. Cells were seeded into 96-well plates (Falcon-Primaria #3872) at a density of approximately 6500 cells/well for use in oligomeric compound transfection experiments.

RAW264.7: The mouse Abelson murine leukemia virus-induced tumor macrophage cell line is obtained from the American Type Culture Collection (ATCC) (Manassas, Va.). RAW 264.7 cells are routinely cultured in alpha-MEM (Invitrogen Corporation, Carlsbad, Calif.) supplemented with 10% fetal bovine serum (Invitrogen Corporation, Carlsbad, Calif.), penicillin 100 units per mL, and streptomycin 100 .micro.g/mL (Invitrogen Corporation, Carlsbad, Calif.). Cells are routinely passaged by trypsinization and dilution when they reach 90% confluence. Cells are seeded into 24-well plates (Falcon-353047) at a density of ~20,000 cells/cm2 for treatment with the oligomeric compounds of the invention.

For Northern blotting or other analysis, cells may be seeded onto 100 mm or other standard tissue culture plates and treated similarly, using appropriate volumes of medium and oligonucleotide.

Treatment with antisense compounds: When cells reach appropriate confluency, they are treated with 50 nM of oligonucleotide using Lipofectin™. When cells reached 65-75% confluency, they were treated with oligonucleotide. Oligonucleotide was mixed with LIPOFECTIN™ (Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 .micro.g/mL per 100 nM oligonucleotide. Final concentration of the oligonucleotide was 50 nM. This transfection mixture was incubated at room temperature for approximately 0.5 hours. For cells grown in 96-well plates, wells were washed once with 100 .micro.L OPTI-MEM™-1 and then treated with 130 .micro.L of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37 .deg.C, the medium containing the transfection mixture was replaced with fresh culture medium. Cells were harvested 16-24 hours after oligonucleotide treatment.

Control Oligonucleotides

Control oligonucleotides are used to determine the optimal oligomeric compound concentration for a particular cell line. Furthermore, when antisense compounds of the invention are tested in oligomeric compound screening experiments or phenotypic assays, control oligonucleotides are tested in parallel with compounds of the invention.

The concentration of oligonucleotide used will vary from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 mM to 300 nM when the antisense oligonucleotide is transfected using a liposome reagent and 1 .micro.M to 40 .micro.M when the antisense oligonucleotide is transfected by electroporation. Representative control oligos are presented in table 17.

TABLE 17

Control oligonucleotides for cell line testing, oligomeric compound screening and phenotypic assays

| Compound # | Target Name | Species of Target | Sequence (5' to 3') | Motif | SEQ ID NO |
|---|---|---|---|---|---|
| 113131 | CD86 | Human | CGTGTGTCTGTGCTAGTCCC | 5-10-5 | 6 |
| 289865 | forkhead box O1A (rhabdomyosarcoma) | Human | GGCAACGTGAACAGGTCCAA | 5-10-5 | 7 |
| 25237 | integrin beta 3 | Human | GCCCATTGCTGGACATGC | 4-10-4 | 8 |
| 196103 | integrin beta 3 | Human | AGCCCATTGCTGGACATGCA | 5-10-5 | 9 |
| 148715 | Jagged 2 | Human; Mouse; Rat | TTGTCCCAGTCCCAGGCCTC | 5-10-5 | 10 |
| 18076 | Jun-N Terminal Kinase-1 | Human | CTTTC$^{u}$CGTTGGA$^{u}$C$^{u}$CCCTGGG | 5-9-6 | 11 |
| 18078 | Jun N-Terminal Kinase-2 | Human | GTGCG$^{u}$CG$^{u}$CGAG$^{u}$C$^{u}$C$^{u}$CGAAATC | 5-9-6 | 12 |
| 183881 | kinesin-like 1 | Human | ATCCAAGTGCTACTGTAGTA | 5-10-5 | 13 |
| 29848 | none | none | NNNNNNNNNNNNNNNNNNNN | 5-10-5 | 14 |
| 226844 | Notch (Drosophila) homolog 1 | Human; Mouse | GCCCTCCATGCTGGCACAGG | 5-10-5 | 15 |

TABLE 17-continued

Control oligonucleotides for cell line testing, oligomeric compound screening and phenotypic assays

| Compound # | Target Name | Species of Target | Sequence (5' to 3') | Motif | SEQ ID NO |
|---|---|---|---|---|---|
| 105990 | Peroxisome proliferator activated receptor gamma | Human | AGCAAAAGATCAATCCGTTA | 5-10-5 | 16 |
| 336806 | Raf kinase C | Human | TACAGAAGGCTGGGCCTTGA | 5-10-5 | 17 |
| 15770 | Raf kinase C | Mouse; Murine sarcoma virus; Rat | ATGCATT$^{u}$CTG$^{u}$C$^{u}$C$^{u}$C$^{u}$CAAGGA | 5-10-5 | 18 |
| 141923 | None | None | CCTTCCCTGAAGGTTCCTCC | 5-10-5 | 138 |
| 129700 | None | None | TAGTGCGGACCTACCCACGA | 5-10-5 | 139 |

EXAMPLE 2

Real-Time Quantitative PCR Analysis of PTPRU mRNA Levels

Quantitation of PTPRU mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the PTPRU being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 .micro.L PCR cocktail (2.5×PCR buffer minus MgCl.sub.2, 6.6 mM MgCl.sub.2, 375 micro. M each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 .micro.L total RNA solution (20-200 ng). The RT reaction was carried out by incubation for 30 minutes at 48 .deg.C. Following a 10 minute incubation at 95 .deg.C to activate the PLATINUM® Taq, 40 cycles of a two-step PCR protocol were carried out: 95 .deg.C for 15 seconds (denaturation) followed by 60 .deg.C for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 .micro.L of RiboGreen™ working reagent (RiboGreen™ reagent diluted 1:350 in 10 mM Tris-HCl, 1 mM EDTA, pH 7.5) was pipetted into a 96-well plate containing 30 .micro.L purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

PTPRU-specific primers and probes for use in real-time PCR

| Species | Target SEQ ID NO | Sequence Description | Sequence (5' to 3') | SEQ ID NO |
|---|---|---|---|---|
| Human | 1, 2 & 4 | Fwd Primer | GAGCCTGAGCGAGAATGATAGC | 32 |
| Human | 1, 2 & 4 | Rev Primer | GGGATCCAGTCATATTCCACACA | 33 |

TABLE 2-continued

PTPRU-specific primers and probes for use in real-time PCR

| Species | Target SEQ ID NO | Sequence Description | Sequence (5' to 3') | SEQ ID NO |
|---|---|---|---|---|
| Human | 1, 2 & 4 | Probe | FAM-CGTCTACGTGCGCGTTAATGG-TAMRA | 34 |
| Mouse | 5 | Fwd Primer | GCCCAGAAAGGCCTATCTCAT | 35 |
| Mouse | 5 | Rev Primer | GCAATTCGGATGCAGTTCAGT | 36 |
| Mouse | 5 | Probe | FAM-AGGCAGCAAGCCACCTGAAAGGG-TAMRA | 37 |

EXAMPLE 3

Antisense Inhibition of Human PTPRU Expression by Antisense Compounds

A series of antisense compounds was designed to target different regions of human PTPRU RNA, using published sequences or portions of published sequences as cited in Table 1. The designed antisense compounds are complementary to one or more of the target nucleic acids in Table 1. The start and stop sites on the target nucleic acids for each antisense compound are presented in Tables 3a, b and c.

TABLE 3a

SEQ ID NO 1

| Compound # | Start Site | Stop Site |
|---|---|---|
| 356182 | 128 | 147 |
| 284985 | 206 | 225 |
| 284986 | 211 | 230 |
| 284987 | 431 | 450 |
| 284988 | 436 | 455 |
| 284989 | 441 | 460 |
| 284990 | 545 | 564 |
| 284991 | 550 | 569 |
| 284992 | 555 | 574 |
| 284993 | 560 | 579 |
| 284994 | 565 | 584 |
| 284995 | 570 | 589 |
| 284996 | 610 | 629 |
| 284997 | 615 | 634 |
| 284998 | 1046 | 1065 |
| 284999 | 1051 | 1070 |
| 285000 | 1056 | 1075 |
| 285001 | 1062 | 1081 |
| 285002 | 1150 | 1169 |
| 285003 | 1304 | 1323 |
| 285004 | 1422 | 1441 |
| 285005 | 1471 | 1490 |
| 285006 | 1619 | 1638 |
| 285007 | 1624 | 1643 |
| 285008 | 1691 | 1710 |
| 356183 | 1892 | 1911 |
| 285009 | 1901 | 1920 |
| 285010 | 1906 | 1925 |
| 285011 | 1911 | 1930 |
| 285012 | 1916 | 1935 |
| 348393 | 2179 | 2198 |
| 285019 | 2348 | 2367 |
| 285020 | 2353 | 2372 |
| 285021 | 2378 | 2397 |
| 285022 | 2429 | 2448 |
| 285023 | 2434 | 2453 |
| 356184 | 2445 | 2464 |
| 285025 | 2513 | 2532 |

TABLE 3a-continued

SEQ ID NO 1

| Compound # | Start Site | Stop Site |
|---|---|---|
| 285026 | 2549 | 2568 |
| 285027 | 2669 | 2688 |
| 285030 | 2990 | 3009 |
| 285031 | 2995 | 3014 |
| 285032 | 3000 | 3019 |
| 285033 | 3006 | 3025 |
| 285034 | 3087 | 3106 |
| 285036 | 3224 | 3243 |
| 285037 | 3278 | 3297 |
| 285038 | 3359 | 3378 |
| 285039 | 3364 | 3383 |
| 285040 | 3422 | 3441 |
| 285041 | 3429 | 3448 |
| 285043 | 3566 | 3585 |
| 285044 | 3571 | 3590 |
| 285045 | 3576 | 3595 |
| 285046 | 3845 | 3864 |
| 285047 | 3872 | 3891 |
| 285048 | 3915 | 3934 |
| 285049 | 3974 | 3993 |
| 285050 | 4220 | 4239 |
| 285051 | 4358 | 4377 |
| 356185 | 4405 | 4424 |
| 356186 | 4467 | 4486 |
| 356187 | 5114 | 5133 |
| 356188 | 5359 | 5378 |
| 285054 | 5505 | 5524 |
| 285055 | 5510 | 5529 |
| 285056 | 5515 | 5534 |
| 285057 | 5520 | 5539 |
| 356189 | 5584 | 5603 |

TABLE 3b

SEQ ID NO: 2

| Compound # | Start Site | Stop Site |
|---|---|---|
| 356182 | 128 | 147 |
| 284985 | 206 | 225 |
| 284986 | 211 | 230 |
| 284987 | 431 | 450 |
| 284988 | 436 | 455 |
| 284989 | 441 | 460 |
| 284990 | 545 | 564 |
| 284991 | 550 | 569 |
| 284992 | 555 | 574 |
| 284993 | 560 | 579 |
| 284994 | 565 | 584 |
| 284995 | 570 | 589 |

TABLE 3b-continued

| SEQ ID NO: 2 | | |
|---|---|---|
| Compound # | Start Site | Stop Site |
| 284996 | 610 | 629 |
| 284997 | 615 | 634 |
| 284998 | 1046 | 1065 |
| 284999 | 1051 | 1070 |
| 285000 | 1056 | 1075 |
| 285001 | 1062 | 1081 |
| 285002 | 1150 | 1169 |
| 285003 | 1304 | 1323 |
| 285004 | 1422 | 1441 |
| 285005 | 1471 | 1490 |
| 285006 | 1619 | 1638 |
| 285007 | 1624 | 1643 |
| 285008 | 1691 | 1710 |
| 356183 | 1892 | 1911 |
| 285009 | 1901 | 1920 |
| 285010 | 1906 | 1925 |
| 285011 | 1911 | 1930 |
| 285012 | 1916 | 1935 |
| 348393 | 2179 | 2198 |
| 285019 | 2348 | 2367 |
| 285020 | 2353 | 2372 |
| 285021 | 2378 | 2397 |
| 285022 | 2429 | 2448 |
| 285023 | 2434 | 2453 |
| 356173 | 2445 | 2464 |
| 285025 | 2483 | 2502 |
| 285026 | 2519 | 2538 |
| 285027 | 2639 | 2658 |
| 285030 | 2978 | 2997 |
| 285031 | 2983 | 3002 |
| 285032 | 2988 | 3007 |
| 285033 | 2994 | 3013 |
| 285034 | 3075 | 3094 |
| 285036 | 3212 | 3231 |
| 285037 | 3266 | 3285 |
| 285038 | 3347 | 3366 |
| 285039 | 3352 | 3371 |
| 285040 | 3410 | 3429 |
| 285041 | 3417 | 3436 |
| 285043 | 3554 | 3573 |
| 285044 | 3559 | 3578 |
| 285045 | 3564 | 3583 |
| 285046 | 3833 | 3852 |
| 285047 | 3860 | 3879 |
| 285048 | 3903 | 3922 |
| 285049 | 3962 | 3981 |
| 285050 | 4202 | 4221 |
| 285051 | 4340 | 4359 |
| 356185 | 4387 | 4406 |
| 356186 | 4449 | 4468 |
| 356187 | 5096 | 5115 |
| 356188 | 5340 | 5359 |
| 285054 | 5486 | 5505 |
| 285055 | 5491 | 5510 |
| 285056 | 5496 | 5515 |
| 285057 | 5501 | 5520 |
| 356189 | 5565 | 5584 |

TABLE 3c

| SEQ ID NO: 4 | | |
|---|---|---|
| Compound # | Start Site | Stop Site |
| 356182 | 525 | 544 |
| 284986 | 19165 | 19184 |
| 284987 | 22483 | 22502 |
| 284988 | 22488 | 22507 |

TABLE 3c-continued

| SEQ ID NO: 4 | | |
|---|---|---|
| Compound # | Start Site | Stop Site |
| 284989 | 22493 | 22512 |
| 284990 | 22597 | 22616 |
| 284991 | 22602 | 22621 |
| 284992 | 22607 | 22626 |
| 284993 | 22612 | 22631 |
| 284994 | 22617 | 22636 |
| 284995 | 22622 | 22641 |
| 284997 | 23151 | 23170 |
| 284998 | 24558 | 24577 |
| 284999 | 24563 | 24582 |
| 285000 | 24568 | 24587 |
| 285001 | 24574 | 24593 |
| 285002 | 24662 | 24681 |
| 285003 | 39360 | 39379 |
| 285004 | 39478 | 39497 |
| 285005 | 39527 | 39546 |
| 285006 | 42930 | 42949 |
| 285007 | 42935 | 42954 |
| 285009 | 43927 | 43946 |
| 285010 | 43932 | 43951 |
| 285011 | 43937 | 43956 |
| 285012 | 43942 | 43961 |
| 348393 | 46739 | 46758 |
| 285019 | 48652 | 48671 |
| 285020 | 48657 | 48676 |
| 285021 | 48682 | 48701 |
| 285022 | 48733 | 48752 |
| 285023 | 48738 | 48757 |
| 356174 | 53552 | 53571 |
| 356175 | 53562 | 53581 |
| 356176 | 53592 | 53611 |
| 285025 | 55786 | 55805 |
| 285026 | 55822 | 55841 |
| 356177 | 56678 | 56697 |
| 285027 | 67770 | 67789 |
| 285030 | 74636 | 74655 |
| 285031 | 74641 | 74660 |
| 285032 | 74646 | 74665 |
| 285034 | 75408 | 75427 |
| 285037 | 76480 | 76499 |
| 285038 | 76561 | 76580 |
| 285039 | 76566 | 76585 |
| 356178 | 76815 | 76834 |
| 356179 | 78188 | 78207 |
| 285040 | 79289 | 79308 |
| 285041 | 79296 | 79315 |
| 285043 | 79927 | 79946 |
| 285044 | 79932 | 79951 |
| 285045 | 79937 | 79956 |
| 285047 | 84592 | 84611 |
| 285048 | 84635 | 84654 |
| 285049 | 84694 | 84713 |
| 356180 | 87516 | 87535 |
| 285050 | 87619 | 87638 |
| 356181 | 87668 | 87687 |
| 285051 | 89159 | 89178 |
| 356186 | 89540 | 89559 |
| 356187 | 90187 | 90206 |
| 356188 | 90432 | 90451 |
| 285054 | 90578 | 90597 |
| 285055 | 90583 | 90602 |
| 285056 | 90588 | 90607 |
| 285057 | 90593 | 90612 |
| 356189 | 90657 | 90676 |

As stated above, antisense oligonucleotides directed to a target or more preferably to an active target segment can be from about 13 to about 80 linked nucleobases. The following Table 3d provides a non-limiting example of such antisense oligonucleotides targeting SEQ ID NO 1.

TABLE 3d

| Antisense Oligonucleotides from about 13 to about 35 Nucleobases | |
|---|---|
| Sequence | Length |
| CAGCCAGCTCAGCCTGGTGC | 20 nucleobases (SEQ ID NO: 48) |
| AGTGCTGACAGCCAG | 15 nucleobases (SEQ ID NO: 19) |
| GCTGACAGCCAGCTC | 15 nucleobases (SEQ ID NO: 20) |
| GTGCTGACAGCCA | 13 nucleobases (SEQ ID NO: 21) |
| AGTGCTGACAGCCAGCTCAGCCTG | 24 nucleobases (SEQ ID NO: 22) |
| GCCAGCTCAGCCTG | 14 nucleobases (SEQ ID NO: 23) |
| AGAAAGTGCTGACAGCCAGCTCAGCCTGGTGCCAC | 35 nucleobases (SEQ ID NO: 24) |
| CTGACAGCCAGCTCAGCCTGGTGCCAC | 27 nucleobases (SEQ ID NO: 25) |
| CAGCCAGCTCAGCCTGGTGCCAC | 22 nucleobases (SEQ ID NO: 26) |

Antisense oligonucleotides directed to a target or more preferably to an active target segment can also contain mismatched nucleobases when compared to the target sequence. The following Table 3e provides a non-limiting example of such antisense oligonucleotides targeting nucleobases 565 to 584 of SEQ ID NO 1. Mismatched nucleobases are underlined. One ordinarily skilled in the art understands that antisense compounds can tolerate mismatches yet still retain their ability to hybridize with a target site and modulate the target nucleic acid through antisense mechanisms.

TABLE 3e

| Antisense Oligonucleotides from about 1-3 Nucleobases Mismatched to the Target Sequence | |
|---|---|
| Sequence | Number of mismatches to SEQ ID NO: 1 |
| CAGCCAGCTCAGCGTGGTGC (SEQ ID NO: 48) | None |
| CAGCCAGCTCAGCCTGTTGC (SEQ ID NO: 27) | One mismatch |
| CAGCCAGCTCAGCCTGGTGG (SEQ ID NO: 28) | One mismatch |
| TTGCCAGCTCAGCCTGGTGC (SEQ ID NO: 29) | Two mismatches |
| CAGGCAGCTCACCCTGGTGC (SEQ ID NO: 30) | Two mismatches |
| CAGTCAGCACAGCCTTGTGC (SEQ ID NO: 31) | Three mismatches |

These antisense compounds were screened in vitro to determine the compound's ability to modulate expression of a target nucleic acid that encodes PTPRU. The compounds shown in Table 4 are all chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the primer-probe set designed to hybridize to human PTPRU (Table 2). Data are averages from two experiments in which A549 cells were treated with 50 nM of the disclosed antisense compounds using LIPOFECTIN™. A reduction in expression is expressed as percent inhibition in Table 4. The control oligomeric compound used was SEQ ID NO: 12.

TABLE 4

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 356182 | 1 | 128 | GCACGGGCCATGGTTGGAGC | 53 | 38 |
| 284985 | 1 | 206 | TCGAAGGTGCAGCCAGCTGC | 62 | 39 |

TABLE 4-continued

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284986 | 1 | 211 | CCTCCTCGAAGGTGCAGCCA | 81 | 40 |
| 284987 | 1 | 431 | AAGTAGCTGAACTGCACACA | 77 | 41 |
| 284988 | 1 | 436 | ACAGGAAGTAGCTGAACTGC | 81 | 42 |
| 284989 | 1 | 441 | GCTGTACAGGAAGTAGCTGA | 76 | 43 |
| 284990 | 1 | 545 | CACTGACGGCCGTGGGATCC | 62 | 44 |
| 284991 | 1 | 550 | GGTGCCACTGACGGCCGTGG | 66 | 45 |
| 284992 | 1 | 555 | AGCCTGGTGCCACTGACGGC | 73 | 46 |
| 284993 | 1 | 560 | AGCTCAGCCTGGTGCCACTG | 63 | 47 |
| 284994 | 1 | 565 | CAGCCAGCTCAGCCTGGTGC | 59 | 48 |
| 284995 | 1 | 570 | GCTGACAGCCAGCTCAGCCT | 79 | 49 |
| 284996 | 1 | 610 | GGGCCTCAAACAGCACCTGA | 77 | 50 |
| 284997 | 1 | 615 | GATGAGGGCCTCAAACAGCA | 57 | 51 |
| 284998 | 1 | 1046 | GAGTTGGTGTTGAGCTGGAT | 82 | 52 |
| 284999 | 1 | 1051 | TGATGGAGTTGGTGTTGAGC | 73 | 53 |
| 285000 | 1 | 1056 | GCCAATGATGGAGTTGGTGT | 80 | 54 |
| 285001 | 1 | 1062 | CCCGTCGCCAATGATGGAGT | 84 | 55 |
| 285002 | 1 | 1150 | ACAGCTTGTAGGTCTGCAGG | 50 | 56 |
| 285003 | 1 | 1304 | TGGATCTCAGCAAAAGCCAG | 57 | 57 |
| 285004 | 1 | 1422 | GATGGTCTGGTTGTGGCTGC | 77 | 58 |
| 285005 | 1 | 1471 | TCTTGATGGTGTAGCGGCTG | 80 | 59 |
| 285006 | 1 | 1619 | TCCTCCAGTGGAGTGAAGGT | 75 | 60 |
| 285007 | 1 | 1624 | TCATGTCCTCCAGTGGAGTG | 65 | 61 |
| 285008 | 1 | 1691 | TGGTAGCTGATCTCATACTG | 80 | 62 |
| 356183 | 1 | 1892 | AAGCTGGGAGCAGAGATGTT | 55 | 63 |
| 285009 | 1 | 1901 | GCATAATCAAAGCTGGGAGC | 80 | 64 |
| 285010 | 1 | 1906 | TGTCGGCATAATCAAAGCTG | 70 | 65 |
| 285011 | 1 | 1911 | CGGCATGTCGGCATAATCAA | 75 | 66 |
| 285012 | 1 | 1916 | GGTGACGGCATGTCGGCATA | 77 | 67 |
| 348393 | 1 | 2179 | AGGTCTGGTTGTCACCCACG | 72 | 68 |
| 285019 | 1 | 2348 | TCCTCCGATCTCTGGGACAC | 53 | 69 |
| 285020 | 1 | 2353 | CCATCTCCTCCGATCTCTGG | 74 | 70 |
| 285021 | 1 | 2378 | CCTGCACAGATGCCCAGGAT | 73 | 71 |
| 285022 | 1 | 2429 | CGGATGATGACAATGATGGC | 49 | 72 |
| 285023 | 1 | 2434 | CTTTGCGGATGATGACAATG | 54 | 73 |
| 356184 | 1 | 2445 | GTGGTCTCTCCCTTTGCGGA | 38 | 74 |
| 285025 | 1 | 2513 | TTCTCCTGGCGGTAGTTGAC | 40 | 75 |

TABLE 4-continued

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 285026 | 1 | 2549 | GTGAAGCTGCGGTCCACGGC | 76 | 76 |
| 285027 | 1 | 2669 | CCCAGGAGGCTGCTGGCCTC | 52 | 77 |
| 285030 | 1 | 2990 | AAGTGGTTTGACCTGTGGTA | 69 | 78 |
| 285031 | 1 | 2995 | CTATGAAGTGGTTTGACCTG | 34 | 79 |
| 285032 | 1 | 3000 | AGTGGCTATGAAGTGGTTTG | 76 | 80 |
| 285033 | 1 | 3006 | CCCTTGAGTGGCTATGAAGT | 61 | 81 |
| 285034 | 1 | 3087 | CAGCTTGGTGATCATGACGA | 55 | 82 |
| 285036 | 1 | 3224 | CCTCTCCGCTCCAGGGCAAA | 51 | 83 |
| 285037 | 1 | 3278 | TGCTCTGGCCACGCTGTGAA | 72 | 84 |
| 285038 | 1 | 3359 | ATGGGCCCGGCATCAGGTGG | 56 | 85 |
| 285039 | 1 | 3364 | TGACAATGGGCCCGGCATCA | 45 | 86 |
| 285040 | 1 | 3422 | AGCATCACATCCAGGACGAT | 48 | 87 |
| 285041 | 1 | 3429 | CATGTCCAGCATCACATCCA | 44 | 88 |
| 285043 | 1 | 3566 | GTCTCCCCACACAGGCAGGC | 71 | 89 |
| 285044 | 1 | 3571 | TGGTGGTCTCCCCACACAGG | 80 | 90 |
| 285045 | 1 | 3576 | AGGGATGGTGGTCTCCCCAC | 58 | 91 |
| 285046 | 1 | 3845 | CGTGTGTAGCTGTCAGTCAG | 53 | 92 |
| 285047 | 1 | 3872 | TGCAGGGTCACGATGAAGGC | 80 | 93 |
| 285048 | 1 | 3915 | GTAGACCAGCCGCCAGAAGT | 39 | 94 |
| 285049 | 1 | 3974 | CAGGCGGAGTTGGACTGGTT | 72 | 95 |
| 285050 | 1 | 4220 | TGCCACTTGTCCACCTCAGC | 56 | 96 |
| 285051 | 1 | 4358 | GTTTTGGCAGCAAAGAAAAC | 21 | 97 |
| 356185 | 1 | 4405 | GGTACTGATCCATGGTCTCC | 49 | 98 |
| 356186 | 1 | 4467 | AGGGCCCCGCTATCTTGACT | 55 | 99 |
| 356187 | 1 | 5114 | GGTTCAGGGAAGCTCAGAGC | 80 | 100 |
| 356188 | 1 | 5359 | GTATGACCAGCCCTGCTCTA | 46 | 101 |
| 285054 | 1 | 5505 | ATCTACAGTTTACAGATGGG | 51 | 102 |
| 285055 | 1 | 5510 | GTCATATCTACAGTTTACAG | 80 | 103 |
| 285056 | 1 | 5515 | CAGTAGTCATATCTACAGTT | 82 | 104 |
| 285057 | 1 | 5520 | TAGGTCAGTAGTCATATCTA | 63 | 105 |
| 356189 | 1 | 5584 | GCACGTTTATTTACAAAGCG | 85 | 106 |
| 356173 | 2 | 2445 | CACCGGCTTCCCTTTGCGGA | 56 | 107 |
| 356174 | 4 | 53552 | CTGGCAGCGTGCAAAGAGAG | 59 | 108 |
| 356175 | 4 | 53562 | GTGGTCTCTCCTGGCAGCGT | 73 | 109 |
| 356176 | 4 | 53592 | AGCTACTTACGGGTAGTAGG | 64 | 110 |
| 356177 | 4 | 56678 | ATTTCAAGGGAATATTTACA | 20 | 111 |

TABLE 4-continued

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 356178 | 4 | 76815 | CCTCCTCAGCACCTGGGTCA | 66 | 112 |
| 356179 | 4 | 78188 | CAGCAATATCTCCTAAAGCT | 55 | 113 |
| 356180 | 4 | 87516 | GGTGCCCCTCCTGCAACTGG | 67 | 114 |
| 356181 | 4 | 87668 | AGGTACTCACAGGCAGTGCA | 47 | 115 |

The screen identified active target segments within the human PTPRU mRNA sequence, specifically SEQ ID NO: 1, 2 and 4. Each active target segment was targeted by at least one active antisense oligonucleotide. These active target regions identified for SEQ ID NO: 1 include nucleotides nucleotides 1046 to 1081 (Region A) with an average inhibition of 79.7%, nucleotides 5510 to 5603 (Region B) with an average inhibition of 77.3%, nucleotides 431 to 629 (Region C) with an average inhibition of 71.5%, nucleotides 431 to 589 (Region D) with an average inhibition of 70.9%, nucleotides 431 to 460 (Region E) with an average inhibition of 78.0%, nucleotides 1422 to 1710 (Region F) with an average inhibition of 75.4%, nucleotides 1422 to 1490 (Region G) with an average inhibition of 78.4%, nucleotides 206 to 230 (Region H) with an average inhibition of 71.4%, nucleotides 1619 to 1710 (Region 1) with an average inhibition of 73.3% and nucleotides 1892 to 1935 (Region F) with an average inhibition of 71.4%. Each of the oligonucleotides tested within each of these regions inhibited expression of human PTPRU greater than 50% and over half of the oligonucleotides tested in this region inhibited expression by greater than 75%. Identification of these regions allows for the design of antisense oligonucleotides that modulate the expression of PTPRU.

The active target regions identified for SEQ ID NO: 2 include nucleotides nucleotides 1046 to 1081 (Region AA) with an average inhibition of 79.7%, nucleotides 5491 to 5584 (Region AB) with an average inhibition of 77.3%, nucleotides 206 to 230 (Region AC) with an average inhibition of 71.4%, nucleotides 431 to 589 (Region AD) with an average inhibition of 70.8%, nucleotides 431 to 460 (Region AE) with an average inhibition of 78.0%, nucleotides 431 to 579 (Region AF) with an average inhibition of 71.3%, nucleotides 1422 to 1490 (Region AG) with an average inhibition of 78.4%, nucleotides 1619 to 1710 (Region AH) with an average inhibition of 73.3% and nucleotides 1892 to 1935 (Region AI) with an average inhibition of 71.4%.

Active target regions have also been identified for SEQ ID NO: 4. These active target regions include nucleotides 24558 to 24593 (Region BA) with an average inhibition of 79.7%, nucleotides 90583 to 90676 (Region BB) with an average inhibition of 77.3%, nucleotides 22483 to 22641 (Region BC) with an average inhibition of 70.8%, nucleotides 22483 to 22616 (Region BD) with an average inhibition of 74.1%, nucleotides 43927 to 43961 (Region BE) with an average inhibition of 75.4%, and nucleotides 53552 to 53611 (Region BF) with an average inhibition of 65.3%.

EXAMPLE 4

Antisense Inhibition of Mouse PTPRU Expression by Antisense Compounds

A series of antisense compounds was designed to target different regions of mouse PTPRU, using published sequences cited in Table 1. The compounds are shown in Table 5. All compounds in Table 5 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein and using the mouse primers an probe from Table 2. Data are averages from two experiments in which B 16-F10 cells were treated with 150 nM of the disclosed antisense compounds using LIPOFECTIN™ (as described above). A reduction in expression is expressed as percent inhibition in Table 5. The control oligomeric compound used was SEQ ID NO: 12.

TABLE 5

Inhibition of mouse PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284981 | 5 | 108 | CGCAACTGTATGTACCAAGC | 12 | 116 |
| 284982 | 5 | 176 | ATAGCAGTCGAACATTAATC | 0 | 117 |

TABLE 5-continued

Inhibition of mouse PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284983 | 5 | 225 | TCGTTGGCATAGCTGACACC | 0 | 118 |
| 284984 | 5 | 372 | GAGCCCGGGCCATGGCCGCC | 44 | 119 |
| 284985 | 5 | 448 | TCGAAGGTGCAGCCAGCTGC | 65 | 39 |
| 284986 | 5 | 453 | CCTCCTCGAAGGTGCAGCCA | 39 | 40 |
| 284987 | 5 | 673 | AAGTAGCTGAACTGCACACA | 56 | 41 |
| 284988 | 5 | 678 | ACAGGAAGTAGCTGAACTGC | 100 | 42 |
| 284989 | 5 | 683 | GCTGTACAGGAAGTAGCTGA | 63 | 43 |
| 284990 | 5 | 787 | CACTGACGGCCGTGGGATCC | 60 | 44 |
| 284991 | 5 | 792 | GGTGCCACTGACGGCCGTGG | 37 | 45 |
| 284992 | 5 | 797 | AGCCTGGTGCCACTGACGGC | 79 | 46 |
| 284993 | 5 | 802 | AGCTCAGCCTGGTGCCACTG | 51 | 47 |
| 284994 | 5 | 807 | CAGCCAGCTCAGCCTGGTGC | 68 | 48 |
| 284995 | 5 | 812 | GCTGACAGCCAGCTCAGCCT | 64 | 49 |
| 284996 | 5 | 852 | GGGCCTCAAACAGCACCTGA | 74 | 50 |
| 284997 | 5 | 857 | GATGAGGGCCTCAAACAGCA | 68 | 51 |
| 284999 | 5 | 1293 | TGATGGAGTTGGTGTTGAGC | 39 | 53 |
| 285000 | 5 | 1298 | GCCAATGATGGAGTTGGTGT | 63 | 54 |
| 285001 | 5 | 1304 | CCCGTCGCCAATGATGGAGT | 64 | 55 |
| 285002 | 5 | 1392 | ACAGCTTGTAGGTCTGCAGG | 67 | 56 |
| 285003 | 5 | 1546 | TGGATCTCAGCAAAAGCCAG | 71 | 57 |
| 285004 | 5 | 1664 | GATGGTCTGGTTGTGGCTGC | 53 | 58 |
| 285005 | 5 | 1713 | TCTTGATGGTGTAGCGGCTG | 60 | 59 |
| 285006 | 5 | 1861 | TCCTCCAGTGGAGTGAAGGT | 52 | 60 |
| 285007 | 5 | 1866 | TCATGTCCTCCAGTGGAGTG | 56 | 61 |
| 285008 | 5 | 1933 | TGGTAGCTGATCTCATACTG | 62 | 62 |
| 285009 | 5 | 2143 | GCATAATCAAAGCTGGGAGC | 71 | 64 |
| 285010 | 5 | 2148 | TGTCGGCATAATCAAAGCTG | 56 | 65 |
| 285011 | 5 | 2153 | CGGCATGTCGGCATAATCAA | 75 | 66 |
| 285012 | 5 | 2158 | GGTGACGGCATGTCGGCATA | 60 | 67 |
| 285013 | 5 | 2206 | TGGGCCGGCCTCAACAGCAC | 50 | 120 |
| 285014 | 5 | 2261 | TGGCCGCTCTTCCTCCACAA | 67 | 121 |
| 285015 | 5 | 2332 | GCCAGGGCCGTCTCAAAGGT | 79 | 122 |
| 285016 | 5 | 2387 | CTCAAGCAGGCTGCTGGCAG | 60 | 123 |
| 285017 | 5 | 2441 | TGGGTTCCAGAAGCCACGAT | 50 | 124 |
| 285018 | 5 | 2561 | TCGCTTGCTCTCCTTGCACG | 69 | 125 |
| 285019 | 5 | 2590 | TCCTCCGATCTCTGGGACAC | 40 | 69 |

TABLE 5-continued

Inhibition of mouse PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 285020 | 5 | 2595 | CCATCTCCTCCGATCTCTGG | 30 | 70 |
| 285021 | 5 | 2620 | CCTGCACAGATGCCCAGGAT | 64 | 71 |
| 285022 | 5 | 2671 | CGGATGATGACAATGATGGC | 24 | 72 |
| 285023 | 5 | 2676 | CTTTGCGGATGATGACAATG | 36 | 73 |
| 285024 | 5 | 2681 | CTTCCCTTTGCGGATGATGA | 58 | 126 |
| 285025 | 5 | 2725 | TTCTCCTGGCGGTAGTTGAC | 40 | 75 |
| 285026 | 5 | 2761 | GTGAAGCTGCGGTCCACGGC | 55 | 76 |
| 285027 | 5 | 2881 | CCCAGGAGGCTGCTGGCCTC | 44 | 77 |
| 285028 | 5 | 3027 | TCTCGTACTCCTGCTTGAAG | 49 | 127 |
| 285029 | 5 | 3103 | TAGGCAGACACTGGCTCCTG | 55 | 128 |
| 285030 | 5 | 3202 | AAGTGGTTTGACCTGTGGTA | 57 | 78 |
| 285031 | 5 | 3207 | CTATGAAGTGGTTTGACCTG | 33 | 79 |
| 285032 | 5 | 3212 | AGTGGCTATGAAGTGGTTTG | 42 | 80 |
| 285033 | 5 | 3218 | CCCTTGAGTGGCTATGAAGT | 38 | 81 |
| 285034 | 5 | 3299 | CAGCTTGGTGATCATGACGA | 51 | 82 |
| 285035 | 5 | 3377 | CAGCGTGATCTTGATGTCCC | 53 | 129 |
| 285036 | 5 | 3436 | CCTCTCCGCTCCAGGGCAAA | 17 | 83 |
| 285037 | 5 | 3490 | TGCTCTGGCCACGCTGTGAA | 26 | 84 |
| 285038 | 5 | 3571 | ATGGGCCCGGCATCAGGTGG | 26 | 85 |
| 285039 | 5 | 3576 | TGACAATGGGCCCGGCATCA | 54 | 86 |
| 285040 | 5 | 3634 | AGCATCACATCCAGGACGAT | 54 | 87 |
| 285041 | 5 | 3641 | CATGTCCAGCATCACATCCA | 37 | 88 |
| 285042 | 5 | 3718 | GTCTGGATCATGTTGACCCG | 38 | 130 |
| 285043 | 5 | 3778 | GTCTCCCCACACAGGCAGGC | 72 | 89 |
| 285044 | 5 | 3783 | TGGTGGTCTCCCCACACAGG | 28 | 90 |
| 285045 | 5 | 3788 | AGGGATGGTGGTCTCCCCAC | 27 | 91 |
| 285046 | 5 | 4057 | CGTGTGTAGCTGTCAGTCAG | 42 | 92 |
| 285047 | 5 | 4084 | TGCAGGGTCACGATGAAGGC | 28 | 93 |
| 285048 | 5 | 4127 | GTAGACCAGCCGCCAGAAGT | 28 | 94 |
| 285049 | 5 | 4186 | CAGGCGGAGTTGGACTGGTT | 55 | 95 |
| 285050 | 5 | 4432 | TGCCACTTGTCCACCTCAGC | 74 | 96 |
| 285051 | 5 | 4570 | GTTTTGGCAGCAAAGAAAAC | 44 | 97 |
| 285052 | 5 | 4677 | GCGCCTGCTATCTCAACTCC | 67 | 131 |
| 285053 | 5 | 4800 | CAGTGTCCGTCCGTTCCAGT | 44 | 132 |
| 285054 | 5 | 5621 | ATCTACAGTTTACAGATGGG | 48 | 102 |
| 285055 | 5 | 5626 | GTCATATCTACAGTTTACAG | 45 | 103 |

TABLE 5-continued

| Inhibition of mouse PTPRU mRNA levels by chimeric oligonucleotides having 2'-MOE wings and deoxy gap | | | | | |
|---|---|---|---|---|---|
| Compound # | Target SEQ ID NO | Target Site | Sequence (5' to 3') | % Inhibition | SEQ ID NO |
| 285056 | 5 | 5631 | CAGTAGTCATATCTACAGTT | 44 | 104 |
| 285057 | 5 | 5636 | TAGGTCAGTAGTCATATCTA | 36 | 105 |
| 285058 | 5 | 5713 | TGGCATTCAGAGAGCACATT | 33 | 133 |

EXAMPLE 5

Antisense Inhibition of PTPRU by Chimeric Phosphorothioate Oligonucleotides having 2'-MOE Wings and a Deoxy Gap: Dose Response Studies In a further embodiment of the present invention, oligonucleotides were selected for dose-response studies. A549 cells were treated with 10, 20, 40, or 80 nM of PTPRU antisense oligonucleotides Compound # 285001, Compound # 285008, Compound # 285056 or Compound # 356189. Control oligonucleotide Compound # 141923 also was included in this study. Target mRNA levels were measured as described in other examples herein. Untreated cells served as the control to which the data were normalized.

Results of these studies are shown in Table 6. Data are averages from three experiments and are expressed as percent inhibition relative to untreated control.

TABLE 6

| Inhibition of PTPRU mRNA expression in A549 Cells | | | | | |
|---|---|---|---|---|---|
| | | % Inhibition Dose of oligonucleotide | | | |
| Compound # | SEQ ID NO | 10 nM | 20 nM | 40 nM | 80 nM |
| 285001 | 55 | 46 | 64 | 78 | 81 |
| 285008 | 62 | 38 | 56 | 62 | 70 |
| 285056 | 104 | 36 | 60 | 71 | 74 |
| 356189 | 106 | 38 | 52 | 61 | 57 |
| 141923 | 138 | 4 | 5 | 0 | 0 |

A second screen was performed to test dose response with additional PTPRU oligonucleotides. A549 cells were treated with 10, 20, 40, or 80 nM of PTPRU antisense oligonucleotides Compound # 284986, Compound # 284995, Compound # 284998 and Compound # 285000. Control oligonucleotides Compound # 129700 and Compound # 141923 also were included in this study. Target mRNA levels were measured as described in other examples herein. Untreated cells served as the control to which the data were normalized.

Results of these studies are shown in Table 7. Data are averages from three experiments and are expressed as percent inhibition relative to untreated control.

TABLE 7

| Inhibition of PTPRU mRNA expression in A549 Cells | | | | | |
|---|---|---|---|---|---|
| | | % Inhibition Dose of oligonucleotide | | | |
| Compound # | SEQ ID NO | 10 nM | 20 nM | 40 nM | 80 nM |
| 284986 | 40 | 31 | 54 | 66 | 71 |
| 284995 | 49 | 46 | 55 | 69 | 82 |
| 284998 | 52 | 30 | 56 | 72 | 81 |
| 285000 | 54 | 33 | 48 | 61 | 51 |
| 141923 | 138 | 0 | 0 | 0 | 0 |
| 129700 | 139 | 0 | 0 | 0 | 0 |

As shown in Table 6 and Table 7, each of the PTPRU antisense oligonucleotides tested were effective at reducing PTPRU mRNA levels in a dose-dependent manner.

EXAMPLE 6

Antisense Inhibition of Mouse PTPRU Expression by Antisense Compounds: A Second Screen of Antisense Compounds in RAW Cells In accordance with the present invention, a second series of antisense compounds was designed to target regions of mouse PTPRU, using published sequences cited in Table 1. The compounds are shown in Table 8. All compounds in Table 8 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the following primer-probe set designed to hybridize to mouse PTPRU:

Forward primer: GGCACAGCAAACGAGGATTT (incorporated herein as SEQ ID NO: 256)

Reverse primer: GCAGACCAACGCAGAAACTG (incorporated herein as SEQ ID NO: 257)

And the PCR probe was:

FAM-TCCCGAGTGTTCCGGGT-MGB (incorporated herein as SEQ ID NO: 258), where FAM is the fluorescent dye and MGB is the quencher dye. Data are averages from three experiments in which RAW 264.7 cells were treated with 100 nM of the disclosed antisense compounds using LIPOFECTIN™. A reduction in expression is expressed as percent inhibition in Table 8.

TABLE 8

Inhibition of mouse PTPRU miRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284988 | 5 | 678 | ACAGGAAGTAGCTGAACTGC | 4 | 42 |
| 284992 | 5 | 797 | AGCCTGGTGCCACTGACGGC | 23 | 46 |
| 284998 | 5 | 1288 | GAGTTGGTGTTGAGCTGGAT | 19 | 52 |
| 285015 | 5 | 2332 | GCCAGGGCCGTCTCAAAGGT | 35 | 122 |
| 348312 | 5 | 29 | TAAAGTTGCAGGAGCCAGAT | 19 | 140 |
| 348314 | 5 | 136 | ACAATGAACACGTAAGTGCC | 3 | 141 |
| 348315 | 5 | 258 | GCGGAGCGGGACTGGCGCCG | 0 | 142 |
| 348316 | 5 | 300 | CGGGAGCCCAAGGCGAGCGG | 26 | 143 |
| 348317 | 5 | 351 | CCTAGGTCCTGGAGACCCGC | 8 | 144 |
| 348320 | 5 | 527 | GATCCGCACTTGCTCCCATT | 50 | 145 |
| 348321 | 5 | 620 | GATGTGGGCCCTCTGACCTG | 12 | 146 |
| 348324 | 5 | 674 | GAAGTAGCTGAACTGCACAC | 0 | 147 |
| 348325 | 5 | 676 | AGGAAGTAGCTGAACTGCAC | 0 | 148 |
| 348326 | 5 | 680 | GTACAGGAAGTAGCTGAACT | 28 | 149 |
| 348328 | 5 | 684 | TGCTGTACAGGAAGTAGCTG | 0 | 150 |
| 348329 | 5 | 791 | GTGCCACTGACGGCCGTGGG | 0 | 151 |
| 348330 | 5 | 793 | TGGTGCCACTGACGGCCGTG | 0 | 152 |
| 348331 | 5 | 795 | CCTGGTGCCACTGACGGCCG | 0 | i53 |
| 348332 | 5 | 799 | TCAGCCTGGTGCCACTGACG | 16 | i54 |
| 348334 | 5 | 803 | CAGCTCAGCCTGGTGCCACT | 15 | 155 |
| 348336 | 5 | 814 | GTGCTGACAGCCAGCTCAGC | 0 | 156 |
| 348340 | 5 | 848 | CTCAAACAGCACCTGAAACT | 20 | 157 |
| 348342 | 5 | 854 | GAGGGCCTCAAACAGCACCT | 48 | 158 |
| 348343 | 5 | 856 | ATGAGGGCCTCAAACAGCAC | 26 | 159 |
| 348344 | 5 | 858 | AGATGAGGGCCTCAAACAGC | 0 | 160 |
| 348345 | 5 | 886 | AAGCCTATGTAGCCCTTGTG | 60 | 161 |
| 348346 | 5 | 911 | ATAGCTGAAGAGCAAGATGT | 11 | 162 |
| 348347 | 5 | 959 | GACCTCCACGTCCCCAAGGC | 0 | i63 |
| 348348 | 5 | 989 | GCATTGGAAGGATGCGTTCT | 47 | 164 |
| 348349 | 5 | 1025 | GAAGTGTTCTGCCTCTGCGG | 2 | i65 |
| 348350 | 5 | 1055 | CACCAGCACTCCACTCTGAC | 1 | 166 |
| 348351 | 5 | 1084 | TGACTGATGTGCCGCACCCC | 0 | 167 |

TABLE 8-continued

Inhibition of mouse PTPRU miRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 348352 | 5 | 1105 | AAAGTGGCCAGGAAGCGACG | 0 | 168 |
| 348353 | 5 | 1137 | CCTGCTCTGAGCGGCCTACC | 0 | 169 |
| 348354 | 5 | 1186 | TTGGAGACGCCAGCACCACG | 7 | 170 |
| 348355 | 5 | 1221 | GGGTGGGAGGCTCTTTGACG | 0 | 171 |
| 348356 | 5 | 1282 | GTGTTGAGCTGGATAATGAG | 0 | 172 |
| 348357 | 5 | 1284 | TGGTGTTGAGCTGGATAATG | 0 | 173 |
| 348359 | 5 | 1290 | TGGAGTTGGTGTTGAGCTGG | 3 | 174 |
| 348360 | 5 | 1292 | GATGGAGTTGGTGTTGAGCT | 28 | 175 |
| 348361 | 5 | 1294 | ATGATGGAGTTGGTGTTGAG | 3 | 176 |
| 348362 | 5 | 1400 | CAGATGCCACAGCTTGTAGG | 30 | 177 |
| 348363 | 5 | 1432 | AGCACGCTGATTTCATACTC | 0 | 178 |
| 348364 | 5 | 1459 | GTGCCTCCATCTCCCGGGCG | 11 | 179 |
| 348366 | 5 | 1538 | AGCAAAAGCCAGACCTTTGG | 0 | 180 |
| 348367 | 5 | 1930 | TAGCTGATCTCATACTGAGT | 39 | 181 |
| 348369 | 5 | 1987 | ATGGTGCGTCTCGGGCCGGG | 0 | 182 |
| 348370 | 5 | 2018 | GACGTGGTAAGTCTCATTCC | 0 | 183 |
| 348371 | 5 | 2046 | ACGTGGTGCCGGGATGCAGG | 30 | 184 |
| 348373 | 5 | 2108 | TATCTCAGTGAGAGCCGCCT | 9 | 185 |
| 348374 | 5 | 2135 | AAAGCTGGGAGCTGAGATGT | 0 | 186 |
| 348375 | 5 | 2147 | GTCGGCATAATCAAAGCTGG | 0 | 187 |
| 348376 | 5 | 2149 | ATGTCGGCATAATCAAAGCT | 38 | 188 |
| 348377 | 5 | 2151 | GCATGTCGGCATAATCAAAG | 33 | 189 |
| 348378 | 5 | 2155 | GACGGCATGTCGGCATAATC | 6 | 190 |
| 348380 | 5 | 2159 | GGGTGACGGCATGTCGGCAT | 39 | 191 |
| 348381 | 5 | 2322 | TCTCAAAGGTCAGAGGTACC | 22 | 192 |
| 348383 | 5 | 2326 | GCCGTCTCAAAGGTCAGAGG | 28 | 193 |
| 348386 | 5 | 2334 | GAGCCAGGGCCGTCTCAAAG | 5 | 194 |
| 348388 | 5 | 2338 | CCGCGAGCCAGGGCCGTCTC | 12 | 195 |
| 348389 | 5 | 2340 | GGCCGCGAGCCAGGGCCGTC | 0 | 196 |
| 348390 | 5 | 2342 | CAGGCCGCGAGCCAGGGCCG | 6 | 197 |
| 348391 | 5 | 2365 | AGTTCAGCCCCAAAGTAGTG | 0 | 198 |
| 348392 | 5 | 2393 | CATGGCCTCAAGCAGGCTGC | 0 | 199 |
| 348393 | 5 | 2421 | AGGTCTGGTTGTCACCCACG | 0 | 200 |
| 348395 | 5 | 2478 | GGAAATAGATGAGATAGGCC | 0 | 201 |
| 348396 | 5 | 2504 | TTCCCCTTTCAGGTGGCTTG | 0 | 202 |
| 348397 | 5 | 2532 | TGGCAATTCGGATGCAGTTC | 0 | 203 |

TABLE 8-continued

Inhibition of mouse PTPRU miRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 348398 | 5 | 2558 | CTTGCTCTCCTTGCACGCAG | 21 | 204 |
| 348399 | 5 | 2601 | TGAGCCCCATCTCCTCCGAT | 41 | 205 |
| 348400 | 5 | 2629 | GCAAGACCACCTGCACAGAT | 42 | 206 |
| 348401 | 5 | 2656 | ATGGCCCCCAGGAGGAGAAT | 19 | 207 |
| 348402 | 5 | 2686 | ACTGGCTTCCCTTTGCGGAT | 53 | 208 |
| 348403 | 5 | 2715 | GGTAGTTGACCGTGGGTTTC | 0 | 209 |
| 348404 | 5 | 2743 | GCACTCATCATGTGAGTCTT | 18 | 210 |
| 348405 | 5 | 2773 | GTACTCTGATCTGTGAAGCT | 27 | 211 |
| 348406 | 5 | 2803 | GACAGACCCAACCGCTCATC | 16 | 212 |
| 348408 | 5 | 2862 | CGGTGACACCACCGCTTCGC | 30 | 213 |
| 348409 | 5 | 2892 | TTGGAGAACCCCCCAGGAGG | 50 | 214 |
| 348410 | 5 | 2924 | ATACGGAGAACCCTTCCGGC | 0 | 215 |
| 348411 | 5 | 3779 | GGTCTCCCCACACAGGCAGG | 39 | 216 |
| 348412 | 5 | 3799 | AACTCGTTGACAGGGATGGT | 1 | 217 |
| 348413 | 5 | 3824 | GATCATCTCCGTGTAGGTGG | 23 | 218 |
| 348415 | 5 | 3873 | TCTGGAACTCTTCCCGAAGC | 16 | 219 |
| 348417 | 5 | 3929 | CAGCAGGGCAATGCTACACT | 5 | 220 |
| 348419 | 5 | 4036 | GCTGCATTGATGTAGTTATT | 0 | 221 |
| 348420 | 5 | 4211 | CTCCGGCCAGTACTGCAAGC | 0 | 222 |
| 348421 | 5 | 4238 | CATGAGCCCATACTGCTGTC | 0 | 223 |
| 348422 | 5 | 4266 | TTGCTGTGCCAGACACAAAC | 0 | 224 |
| 348424 | 5 | 4321 | TCCTGCAGCCGAGAAGAGTT | 75 | 225 |
| 348426 | 5 | 4379 | CGTGTCCCGATAAGCAGACC | 15 | 226 |
| 348427 | 5 | 4406 | GTGCAGAAAGGCCTTCCTGG | 55 | 227 |
| 348428 | 5 | 4900 | TCTGCACAGGTCTGCAGGGC | 6 | 228 |
| 348429 | 5 | 4928 | ACTAGCTATTTTGGTCCAGG | 0 | 229 |
| 348430 | 5 | 4976 | GGCCAAGGACTGTGATGGAG | 4 | 230 |
| 348431 | 5 | 5006 | GGTGCTCTCTGCAGACACTC | 19 | 231 |
| 348432 | 5 | 5036 | CAGAAAGGACCATACTGGGT | 35 | 232 |
| 348433 | 5 | 5067 | CTGCCAAGTCCCAGTGAGCC | 20 | 233 |
| 348435 | 5 | 5188 | GCAAAGCACCCCAGGTCTGT | 30 | 234 |
| 348436 | 5 | 5220 | GCAGGAAAAGCTCAGAAGCA | 0 | 235 |
| 348437 | 5 | 5255 | GGGATGGAGCCCAGGAAGGA | 13 | 236 |
| 348438 | 5 | 5293 | AGCTGAAGTATATCATTCTG | 18 | 237 |
| 348439 | 5 | 5344 | CCAAGCTGAGCAGGACTGAA | 0 | 238 |

TABLE 8-continued

Inhibition of mouse PTPRU miRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 348440 | 5 | 5367 | CAGCCTTGTGGATTGTCACA | 31 | 239 |
| 348441 | 5 | 5377 | GGCTGTGATTCAGCCTTGTG | 0 | 240 |
| 348442 | 5 | 5414 | CAGCCTCACCAAGAGCCACA | 0 | 241 |
| 348443 | 5 | 5428 | CCCCGATCCAGTGGCAGCCT | 32 | 242 |
| 348444 | 5 | 5449 | CACCAGCCCTGTTCTAGCCT | 29 | 243 |
| 348445 | 5 | 5464 | TACTCTAGGAGCTGACACCA | 0 | 244 |
| 348446 | 5 | 5482 | GTATCCCTTCTTCCTCTGTA | 0 | 245 |
| 348447 | 5 | 5497 | GTCCTCCATTCCAAAGTATC | 27 | 246 |
| 348448 | 5 | 5511 | CAAAAAAAGCACTGGTCCTC | 27 | 247 |
| 348449 | 5 | 5530 | AATAACAAAATAACAACAAC | 3 | 248 |
| 348450 | 5 | 5539 | CATCAAAAAAATAACAAAAT | 10 | 249 |
| 348451 | 5 | 5559 | AAGAGAACTTCCCACCCTCC | 24 | 250 |
| 348452 | 5 | 5564 | TTATAAAGAGAACTTCCCAC | 5 | 251 |
| 348453 | 5 | 5625 | TCATATCTACAGTTTACAGA | 0 | 252 |
| 348454 | 5 | 5652 | ACAGCCCCCTGTGAGGTAGG | 17 | 253 |
| 348455 | 5 | 5677 | TACAAACATTACCTTACACC | 0 | 254 |
| 348456 | 5 | 5707 | TCAGAGAGCACATTTATTTA | 0 | 255 |

In a further embodiment of the present invention, seven PTPRU oligonucleotides were selected for dose-response studies. RAW cells were treated with 5, 10, 25, 50, 100 or 200 nM of PTPRU antisense oligonucleotides Compound # 348343, Compound # 348345, Compound # 349348, Compound # 348400, Compound # 348424, Compound # 343427 or Compound # 284996. Control oligonucleotide Compound # 141923 also was included in this study. Target mRNA levels were measured as described in other examples herein. Untreated cells served as the control to which the data were normalized.

Results of these studies are shown in Table 9. Data are averages from three experiments and are expressed as percent inhibition relative to untreated control for the oligonucleotide doses shown below.

TABLE 9

% Inhibition of PTPRU mRNA expression in RAW Cells

| Compound # | SEQ ID NO | 5 nM | 10 nM | 25 nM | 50 nM | 100 nM | 200 nM |
|---|---|---|---|---|---|---|---|
| 348343 | 159 | 42 | 23 | 23 | 50 | 72 | 70 |
| 348345 | 161 | 28 | 36 | 1 | 39 | 48 | 68 |
| 348348 | 164 | 0 | 0 | 0 | 19 | 30 | 51 |
| 348400 | 206 | 0 | 0 | 23 | 45 | 59 | 73 |
| 348424 | 225 | 8 | 31 | 9 | 30 | 46 | 54 |
| 348427 | 227 | 0 | 16 | 7 | 0 | 30 | 64 |

TABLE 9-continued

% Inhibition of PTPRU mRNA expression in RAW Cells

| Compound # | SEQ ID NO | 5 nM | 10 nM | 25 nM | 50 nM | 100 nM | 200 nM |
|---|---|---|---|---|---|---|---|
| 284996 | 50 | 0 | 0 | 24 | 50 | 65 | 70 |
| 141923 | 138 | 31 | 44 | 47 | 10 | 17 | 3 |

As shown in Table 9, each of the PTPRU antisense oligonucleotides tested demonstrated a dose-responsive effect on PTPRU mRNA inhibition at doses of 10 or 25 nM and greater.

In a further embodiment of the present invention, four PTPRU oligonucleotides were selected for in vivo studies in lean mice. Six-week old male C57BL/6J-Lepr ob/ob+/−mice (Jackson Laboratory, Bar Harbor, Me.) were subcutaneously injected with PTPRU antisense oligonucleotide Compound # 284996, Compound # 349345, Compound # 348424 or Compound # 348427 at a dose of 50 mg/kg two times per week for two weeks (four total doses). Saline-injected animals served as controls. Each treatment group was comprised of five animals. After the treatment period, mice were sacrificed and target levels were evaluated in liver. RNA isolation and target mRNA expression level quantitation were performed using RIBOGREEN™ as described by other examples herein. Results are shown in Table 10 as percent inhibition of PTPRU mRNA as compared to saline treated control.

TABLE 10

| Inhibition of PTPRU expression in liver of lean mice treated with PTPRU antisense oligonucleotide | | |
|---|---|---|
| Treatment | SEQ ID NO | % Inhibition |
| Compound # 284996 | 50 | 63 |
| Compound # 348345 | 161 | 77 |
| Compound # 348424 | 225 | 82 |
| Compound # 348427 | 227 | 64 |

These results demonstrate that PTPRU antisense oligonucleotides effectively reduce PTPRU expression in cell culture and in vivo.

EXAMPLE 7

Impaired Insulin Receptor Signaling in ob/ob and db/db Mice

Leptin is a hormone produced by fat that regulates appetite. Deficiencies in this hormone in both humans and non-human animals leads to obesity. ob/ob mice have a mutation in the leptin gene and db/db mice have a mutation in the leptin receptor gene. Both mutations result in obesity and hyperglycemia. As such, both types of mice are a useful model for the investigation of obesity and diabetes and treatments designed to treat these conditions. db/db mice, which have lower circulating levels of insulin and are more hyperglycemic than ob/ob mice, are often used as a rodent model of type 2 diabetes.

To characterize insulin receptor signaling in ob/ob and db/db mice, the activation states of selected proteins within the insulin receptor pathway were determined following insulin administration. Three of the key players in the insulin receptor signaling pathway are the insulin receptor .beta. subunit (IR-.beta.), PI3-Kinase and Akt. When activated, PI3-Kinase converts 4,5-PIP.sub.2 to 3,4,5-PIP.sub.3 and IR-.beta. and Akt are tyrosine phosphorylated.

Control, C57BL/6J-Lepr ob/ob mice (Jackson Laboratory, Bar Harbor, Me.) or C57B1/6J-Lepr db/db mice (Jackson Laboratory, Bar Harbor, Me.) were injected with 2 U/kg of insulin. After 2, 5, and 30 minutes, animals were sacrificed and liver samples were harvested and processed for PI3-Kinase activity and western blot analysis according to standard procedures. Briefly, to detect PI3-Kinase activity, liver samples were homogenized and immunoprecipitated with anti-IRS-1 antibody (1.5 .micro.g/mg protein) (Upstate Cell Signaling Solutions, Charlottesville, Va.). After washing the immunecomplex pellet, the sample was incubated at 30 . deg.C for 15-30 minutes with .gamma.-.sup.32P-ATP and phosphatidyl inositol substrate. Lipid was then extracted and phosphorylated lipid (PIP.sub.) was resolved by thin-layer chromatography. Plates were exposed to film and the signal was quantitated. To detect phospho-IR-.beta., liver homogenates were immunoprecipitated with anti-phosphotyrosine antibody (4G10, 1.5 .micro.g/mg protein; Upstate Cell Signaling Solutions) and immunoprecipitated protein was subjected to western blotting using anti-IR-.beta. antibody (Santa Cruz Biotechnology, Inc., Santa Cruz, Calif.). To detect phosphorylated Akt, lysates were subjected to western blot using anti-p-Akt.sup.473antibody (Cell Signaling Technology, Beverly, Mass.).

In normal control mice, PI3-Kinase activity was detected as early as 2 minutes following insulin injection, but was greatest at 15 minutes. In both ob/ob and db/db mice, little to no PI3-Kinase activity was detected in response to insulin. Similarly, western blot analysis demonstrated that IR-.beta. and Akt phosphorylation increases in response to insulin in control mice, with a peak around 15 minutes after injection. In contrast, ob/ob and db/db mice exhibit little to IR-.beta. and Akt phosphorylation in response to insulin administration. Thus, these results demonstrate that ob/ob and db/db mice have deficiencies in insulin receptor signaling.

EXAMPLE 8

Effects of Antisense Inhibition of PTPRU: In Vivo Study in ob/ob Mice

In accordance with the present invention, the antisense compounds of the invention were tested in the ob/ob model of obesity and diabetes.

Six-week old male C57BL/6J-Lepr ob/ob mice (Jackson Laboratory, Bar Harbor, Me.) were subcutaneously injected with PTPRU antisense oligonucleotide Compound # 284996 (SEQ ID NO: 50) at a dose of 25 mg/kg two times per week for 4 weeks (eight total doses). Saline-injected animals served as controls. Each treatment group was comprised of six animals. After the treatment period, mice were sacrificed and target levels were evaluated in liver. RNA isolation and target mRNA expression level quantitation were performed using RIBOGREEN™ as described by other examples herein. As compared to saline-treated control animals, treatment with Compound # 284996 resulted in a 60% reduction in PTPRU expression.

The effects of target inhibition on glucose metabolism were evaluated in ob/ob mice treated with PTPRU antisense oligonucleotide Compound # 284996. Plasma glucose was measured prior 3 days prior to the start of treatment and at 12, 19 and 26 days following the first dose. Glucose levels were measured by routine clinical methods using a YSI glucose analyzer (YSI Scientific, Yellow Springs, Ohio). Average plasma glucose levels (in mg/dL) for each treatment group are shown in Table 11.

TABLE 11

| Effect of PTPRU antisense oligonucleotide on plasma glucose levels in ob/ob mice | | | | |
|---|---|---|---|---|
| Treatment | Day −3 (mg/dL) | Day 12 (mg/dL) | Day 19 (mg/dL) | Day 26 (mg/dL) |
| Saline | 375 | 420 | 432 | 427 |
| Compound # 284996 | 374 | 425 | 375 | 303 |

As shown in Table 11, treatment with PTPRU antisense oligonucleotide significantly reduces plasma glucose levels of ob/ob mice.

To assess the effects of inhibition of target mRNA on triglyceride levels, the ob/ob mice were further evaluated 3 days prior to the start of treatment and at 12, 19 and 26 days following the first dose of oligonucleotide for plasma triglycerides (TRIG). Triglycerides were measured by routine clinical analyzer instruments (e.g. Olympus Clinical Analyzer, Melville, N.Y.). Average levels of TRIG (mg/dL) measured for each treatment group are shown in Table 12.

TABLE 12

| Triglyceride levels of ob/ob mice treated with PTPRU antisense oligonucleotide | | | | |
|---|---|---|---|---|
| Treatment | Day −3 | Day 12 | Day 19 | Day 26 |
| Saline | 145 | 192 | 152 | 125 |
| Compound # 284996 | 125 | 140 | 114 | 117 |

As shown in Table 12, treatment with PTPRU antisense oligonucleotide resulted in a reduction in plasma triglyceride levels.

Antisense oligonucleotide-treated and saline control ob/ob mice were further evaluated for PI3-Kinase activity and IR-.beta. phosphorylation following insulin administration as described in other examples herein. As expected, in saline control ob/ob mice, PI3-Kinase activation and IR-.beta. phosphorylation were not observed in response to insulin treatment. In contrast, treatment with antisense oligonucleotide to PTPRU resulted in greater activation of PI3-Kinase and IR-.beta. phosphorylation relative to mice that did not receive insulin. Taken together, these results demonstrate that PTPRU antisense oligonucleotide treatment lowers plasma glucose and triglyceride levels of ob/ob mice and increases insulin responsiveness in these animals.

EXAMPLE 9

Effects of Antisense Inhibition of PTPRU: A Second In Vivo Study in ob/ob Mice In accordance with the present invention, a second study of PTPRU antisense inhibition was performed in ob/ob mice. Six-week old male C57BL/6J-Lepr ob/ob mice (Jackson Laboratory, Bar Harbor, Me.) were subcutaneously injected with PTPRU antisense oligonucleotide Compound # 284996 (SEQ ID NO: 50) or Compound # 285015 (SEQ ID NO: 122) at a dose of 25 mg/kg two times per week for 4 weeks (eight total doses). Saline-injected animals served as controls. Each treatment group was comprised of six animals. After the treatment period, mice were sacrificed and target levels were evaluated in liver. RNA isolation and target mRNA expression level quantitation were performed using RIBOGREEN™ as described by other examples herein. As compared to saline-treated control animals, treatment with Compound # 284996 and Compound # 285015 resulted in a 53% and 34% reduction, respectively, in PTPRU expression.

The effects of target inhibition on glucose metabolism were evaluated in ob/ob mice treated with PTPRU antisense oligonucleotides Compound # 284996 and Compound # 285015. Plasma glucose was measured prior to the start of treatment (Week 0) and at Week 2 and Week 4. Glucose levels were measured by routine clinical methods using a YSI glucose analyzer (YSI Scientific, Yellow Springs, Ohio). Average plasma glucose levels (in mg/dL) for each treatment group are shown in Table 13.

TABLE 13

| Effect of PTPRU antisense oligonucleotide on plasma glucose levels in ob/ob mice | | | |
|---|---|---|---|
| Treatment | Week 0 (mg/dL) | Week 2 (mg/dL) | Week 4 (mg/dL) |
| Saline | 375 | 450 | 430 |
| Compound # 284996 | 359 | 306 | 239 |
| Compound # 285015 | 359 | 314 | 243 |

As shown in Table 13, treatment with PTPRU antisense oligonucleotide significantly reduces plasma glucose levels of ob/ob mice.

To assess triglyceride levels after inhibition of target mRNA, the ob/ob mice were further evaluated at the termination of treatment for plasma triglycerides (TRIG). Triglycerides were measured by routine clinical analyzer instruments (e.g. Olympus Clinical Analyzer, Melville, N.Y.). Average levels of TRIG (mg/dL) measured for each treatment group are shown in Table 14.

TABLE 14

| Effects of PTPRU antisense oligonucleotide treatment on triglyceride levels in ob/ob mice | |
|---|---|
| Treatment | TRIG (mg/dL) |
| Saline | 218 |
| Compound # 284996 | 110 |
| Compound # 285015 | 93 |

Taken together, the results of these studies demonstrate that PTPRU antisense oligonucleotides reduce target mRNA levels in vivo and lead to a reduction in plasma glucose and triglyceride levels in ob/ob mice.

EXAMPLE 10

Effects of Antisense Inhibition of PTPRU: In Vivo Study in db/db Mice

In accordance with the present invention, the antisense compounds of the invention were tested in the db/db model of obesity and diabetes. Six-week old male C57BL/6J-Lepr db/db mice (Jackson Laboratory, Bar Harbor, Me.) were subcutaneously injected with PTPRU antisense oligonucleotide Compound # 284996 (SEQ ID NO: 50) or Compound # 285015 (SEQ ID NO: 122) at a dose of 25 mg/kg two times per week for 4 weeks (eight total doses). Saline-injected animals served as controls. Each treatment group was comprised of six animals. After the treatment period, mice were sacrificed and target levels were evaluated in liver. RNA isolation and target mRNA expression level quantitation were performed using RIBOGREEN™ as described by other examples herein. As compared to saline-treated control animals, treatment with Compound # 284996 and Compound # 285015 resulted in a 45% and 31% reduction, respectively, in PTPRU expression.

The effects of target inhibition on glucose metabolism were evaluated in db/db mice treated with PTPRU antisense oligonucleotides Compound # 284996 and Compound # 285015. Plasma glucose was measured prior to the start of treatment (Week 0) and at Week 2 and Week 4. Glucose levels were measured by routine clinical methods using a YSI glucose analyzer (YSI Scientific, Yellow Springs, Ohio). Average plasma glucose levels (in mg/dL) for each treatment group are shown in Table 15.

TABLE 15

Effect of PTPRU antisense oligonucleotide on plasma glucose levels in db/db mice

| Treatment | Week 0 (mg/dL) | Week 2 (mg/dL) | Week 4 (mg/dL) |
|---|---|---|---|
| Saline | 382 | 479 | 545 |
| Compound # 284996 | 383 | 395 | 464 |
| Compound # 285015 | 380 | 411 | 442 |

As shown in Table 15, treatment with PTPRU antisense oligonucleotide significantly reduces plasma glucose levels of db/db mice.

To assess triglyceride levels after inhibition of target mRNA, the db/db mice were further evaluated at the termination of treatment for plasma triglycerides (TRIG). Triglycerides were measured by routine clinical analyzer instruments (e.g. Olympus Clinical Analyzer, Melville, N.Y.). Average levels of TRIG (mg/dL) measured for each treatment group are shown in Table 16.

TABLE 16

Effects of PTPRU antisense oligonucleotide treatment on triglyceride levels in db/db mice

| Treatment | TRIG (mg/dL) |
|---|---|
| Saline | 311 |
| Compound # 284996 | 200 |
| Compound # 285015 | 295 |

Taken together, the results of these studies demonstrate that PTPRU antisense oligonucleotides reduce target mRNA levels in vivo and lead to a reduction in plasma glucose and triglyceride levels in diabetic animals.

Various modifications of the disclosed compositions and methods will be apparent to those skilled in the art from the foregoing description. Such modifications are also intended to fall within the scope of the appended claims. The appended claims cover all such equivalent variations as fall within the true spirit and scope of the invention. Each of the patents, applications, printed publications, and other published documents mentioned or referred to in this specification are herein incorporated by reference in their entirety.

What is claimed is:

1. A method of reducing PTPRU comprising:

identifying an animal having an increased glucose level or an increased lipid level; and administering to said animal a compound comprising a modified oligonucleotide consisting of 13 to 80 linked nucleosides, wherein said modified oligonucleotide has a nucleobase sequence that is at least 90% complementary to a nucleic acid sequence encoding PTPRU as measured over the entirety of said modified oligonucleotide, wherein said nucleic acid sequence encoding PTPRU is selected from the group consisting of SEQ ID NOs:1, 2, and 4, and wherein expression of said nucleic acid sequence encoding PTPRU is reduced.

2. The method of claim 1, wherein said compound consists of a single-stranded modified oligonucleotide.

3. The method of claim 2, wherein said modified oligonucleotide consists of 13 to 30 linked nucleosides.

4. The method of claim 2, wherein said nucleobase sequence of said modified oligonucleotide is 100% complementary to said nucleic acid sequence encoding PTPRU as measured over the entirety of said modified oligonucleotide.

5. The method of claim 2, wherein at least one internucleoside linkage of said modified oligonucleotide is a modified internucleoside linkage.

6. The method of claim 5, wherein each internucleoside linkage of said modified oligonucleotide is a phosphorothioate internucleoside linkage.

7. The method of claim 2, wherein at least one nucleoside of said modified oligonucleotide comprises a modified sugar.

8. The method of claim 7, wherein at least one modified sugar is a bicyclic sugar.

9. The method of claim 7, wherein at least one modified sugar comprises a 2'-O-methoxyethyl.

10. The method of claim 7, wherein at least one modified sugar comprises a 4'-$(CH_2)_n$—O-2' bridge, wherein n is 1 or 2.

11. The method of claim 2, wherein at least one nucleoside of said modified oligonucleotide comprises a modified nucleobase.

12. The method of claim 11, wherein the modified nucleobase is a 5-methylcytosine.

13. The method of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

14. The method of claim 13, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar; and wherein each internucleoside linkage of said modified oligonucleotide is a phosphorothioate linkage.

15. The method of claim 14, wherein the modified oligonucleotide consists of 20 linked nucleosides.

16. The method of claim 2, wherein the modified oligonucleotide consists of 20 linked nucleosides.

17. The method of claim 1, wherein said compound or a salt thereof is administered in a composition comprising said compound or a salt thereof and a pharmaceutically acceptable carrier or diluent.

18. The method of claim 17, wherein said compound or salt thereof consists of a single-stranded oligonucleotide.

19. The method of claim 1, wherein said animal is human and said nucleic acid sequence encoding PTPRU is SEQ ID NO:1.

20. The method of claim 1, wherein a blood glucose level of said animal is lowered.

21. The method of claim 1, wherein said animal suffers from a disease or condition associated with an increased glucose level.

22. The method of claim 21, wherein said increased glucose level is plasma glucose level.

23. The method of claim 21, wherein the disease or condition is selected from the group consisting of diabetes, type II diabetes, metabolic syndrome, insulin resistance, insulin deficiency, hyperglycemia, obesity and a combination thereof.

24. The method of claim 21, wherein the animal has a deficiency in insulin receptor signaling.

25. The method of claim 21, wherein blood glucose level of said animal is decreased, and said disease or condition is treated.

26. The method of claim 25, wherein said animal is a human.

27. The method of claim 1, wherein a lipid level of said animal is reduced.

28. The method of claim 27, wherein said lipid level is plasma triglyceride level, plasma cholesterol level, hepatic triglyceride level or a combination thereof.

29. The method of claim 1, wherein said animal is suffering from a disease or condition associated with an increased lipid level.

30. The method of claim 29, wherein the increased lipid level is plasma triglyceride level.

31. The method of claim 29, wherein the increased lipid level is hepatic triglyceride level.

32. The method of claim 29, wherein the increased lipid level is plasma cholesterol level.

33. The method of claim 29, wherein the disease or condition is selected from the group consisting of hyperlipidemia, hypertriglyceridemia, obesity, liver steatosis, steatohepatitis, non-alcoholic steatohepatitis, metabolic syndrome, cardiovascular disease, coronary heart disease and a combination thereof.

34. The method of claim 29, wherein said lipid level of said animal is decreased, and said disease or condition is treated.

35. The method of claim 34, wherein said animal is a human.

36. A method of reducing PTPRU comprising:

identifying a human having an elevated lipid level; and administering to said human a compound comprising a modified oligonucleotide consisting of 13 to 80 linked nucleosides, wherein said modified oligonucleotide has a nucleobase sequence that is at least 90% complementary to a nucleic acid sequence encoding PTPRU having SEQ ID NO:1, as measured over the entirety of said modified oligonucleotide, wherein expression of said nucleic acid sequence encoding PTPRU is reduced, and wherein said lipid level of said human is reduced.

* * * * *